United States Patent
Brown et al.

(10) Patent No.: US 12,377,106 B2
(45) Date of Patent: Aug. 5, 2025

(54) PIPERIDINYLPYRAZINE-CARBOXAMIDE COMPOUNDS FOR TREATING AND PREVENTING CANCER AND FOR DEGRADING BTK

(71) Applicant: NURIX THERAPEUTICS, INC., San Francisco, CA (US)

(72) Inventors: Robert J. Brown, San Francisco, CA (US); Arthur T. Sands, San Francisco, CA (US)

(73) Assignee: NURIX THERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 18/049,547

(22) Filed: Oct. 25, 2022

(65) Prior Publication Data
US 2023/0149416 A1    May 18, 2023

Related U.S. Application Data

(60) Provisional application No. 63/391,671, filed on Jul. 22, 2022, provisional application No. 63/263,081, filed on Oct. 26, 2021.

(51) Int. Cl.
| | | |
|---|---|---|
| A61K 31/5377 | (2006.01) | |
| A61K 9/00 | (2006.01) | |
| A61K 31/497 | (2006.01) | |
| A61K 31/506 | (2006.01) | |
| A61P 35/02 | (2006.01) | |

(52) U.S. Cl.
CPC ........ *A61K 31/5377* (2013.01); *A61K 9/0053* (2013.01); *A61K 31/497* (2013.01); *A61K 31/506* (2013.01); *A61P 35/02* (2018.01)

(58) Field of Classification Search
CPC .............. A61K 31/5377; A61K 9/0053; A61K 31/497; A61K 31/506; A61P 35/02; A61P 35/00
See application file for complete search history.

(56) References Cited

U.S. PATENT DOCUMENTS

| | | |
|---|---|---|
| 8,586,751 B2 | 11/2013 | De Lucca et al. |
| 10,130,659 B2 | 11/2018 | Wardell et al. |
| (Continued) | | |

FOREIGN PATENT DOCUMENTS

| | | |
|---|---|---|
| WO | WO 2007/072225 A2 | 6/2007 |
| WO | WO 2008/033403 A2 | 3/2008 |
| (Continued) | | |

OTHER PUBLICATIONS

Golub et al. Molecular classification of cancer: class discovery and class prediction by gene expression monitoring. Science. Oct. 15, 1999;286(5439):531-7. doi: 10.1126/science.286.5439.531. PMID: 10521349.*

(Continued)

*Primary Examiner* — Jeffrey S Lundgren
*Assistant Examiner* — Anthony Joseph Seitz
(74) *Attorney, Agent, or Firm* — Squire Patton Boggs (US) LLP

(57) ABSTRACT

This disclosure relates to BTK inhibitor compounds for treating or preventing cancer by daily oral dosing in human subjects in need thereof. The description also provides BTK inhibitor compounds for degrading BTK in vivo by daily oral dosing in human subjects in need thereof.

34 Claims, 6 Drawing Sheets

(56) References Cited

U.S. PATENT DOCUMENTS

| | | | |
|---|---|---|---|
| 10,166,257 | B2 | 1/2019 | Wardell et al. |
| 10,272,113 | B2 | 4/2019 | Wardell et al. |
| 10,336,744 | B2 | 7/2019 | Harling et al. |
| 10,363,273 | B2 | 7/2019 | Wardell et al. |
| 10,398,734 | B2 | 9/2019 | Wardell et al. |
| 10,415,015 | B2 | 9/2019 | Veerapathran et al. |
| 10,420,799 | B2 | 9/2019 | Wardell et al. |
| 10,463,697 | B2 | 11/2019 | Wardell et al. |
| 10,517,894 | B2 | 12/2019 | Frank et al. |
| 10,537,595 | B2 | 1/2020 | Wardell et al. |
| 10,639,330 | B2 | 5/2020 | Wardell et al. |
| 10,646,517 | B2 | 5/2020 | Wardell et al. |
| 10,653,723 | B1 | 5/2020 | Wardell et al. |
| 10,695,372 | B2 | 6/2020 | Wardell et al. |
| 10,894,063 | B2 | 1/2021 | Wardell et al. |
| 10,918,666 | B2 | 2/2021 | Wardell et al. |
| 10,933,094 | B2 | 3/2021 | Wardell et al. |
| 10,946,044 | B2 | 3/2021 | Wardell et al. |
| 10,946,045 | B2 | 3/2021 | Wardell et al. |
| 10,953,046 | B2 | 3/2021 | Wardell et al. |
| 10,953,047 | B2 | 3/2021 | Wardell et al. |
| 11,007,226 | B2 | 5/2021 | Wardell et al. |
| 11,013,770 | B1 | 5/2021 | Wardell et al. |
| 11,026,974 | B2 | 6/2021 | Wardell et al. |
| 11,040,070 | B2 | 6/2021 | Wardell et al. |
| 11,052,115 | B2 | 7/2021 | Wardell et al. |
| 11,052,116 | B2 | 7/2021 | Wardell et al. |
| 11,058,728 | B1 | 7/2021 | Frank et al. |
| 11,083,752 | B2 | 8/2021 | Wardell et al. |
| 11,123,371 | B2 | 9/2021 | Wardell et al. |
| 11,479,556 | B1 * | 10/2022 | Robbins ................ A61P 37/00 |
| 11,541,051 | B2 | 1/2023 | Jin et al. |
| 11,820,781 | B2 * | 11/2023 | Kelly ................ C07D 471/04 |
| 11,866,442 | B2 * | 1/2024 | Robbins ............... C07D 471/10 |
| 2007/0054355 | A1 | 3/2007 | Reiss et al. |
| 2017/0015655 | A1 | 1/2017 | Kaieda et al. |
| 2020/0323904 | A1 | 10/2020 | Sands et al. |
| 2021/0053961 | A1 | 2/2021 | Sands et al. |
| 2021/0053986 | A1 | 2/2021 | Sands et al. |
| 2021/0085717 | A1 | 3/2021 | Gosling et al. |
| 2021/0087259 | A1 | 3/2021 | Gosling et al. |
| 2021/0198280 | A1 | 7/2021 | Kelly et al. |
| 2022/0143195 | A1 | 5/2022 | Kato et al. |
| 2023/0024442 | A1 | 1/2023 | Robbins et al. |
| 2023/0029378 | A1 | 1/2023 | Robbins et al. |
| 2023/0227471 | A1 * | 7/2023 | Kelly ................ C07D 471/04 514/210.16 |

FOREIGN PATENT DOCUMENTS

| | | | | |
|---|---|---|---|---|
| WO | WO 2009/073905 | A2 | 6/2009 | |
| WO | WO 2009/098144 | A1 | 8/2009 | |
| WO | WO 2011/140488 | A1 | 11/2011 | |
| WO | WO 2012/020008 | A1 | 2/2012 | |
| WO | WO 2012/089736 | A1 | 7/2012 | |
| WO | WO 2013/067264 | A1 | 5/2013 | |
| WO | WO 2013/067274 | A1 | 5/2013 | |
| WO | WO 2013/106643 | A2 | 7/2013 | |
| WO | WO 2014/040965 | A1 | 3/2014 | |
| WO | WO 2015/084998 | A1 | 6/2015 | |
| WO | WO 2016/196776 | A2 | 12/2016 | |
| WO | WO 2018/098275 | A1 | 5/2018 | |
| WO | WO 2019/148005 | A1 | 8/2019 | |
| WO | WO 2019/148150 | A1 | 8/2019 | |
| WO | WO-2019246315 | A1 * | 12/2019 | ........... A61K 31/343 |
| WO | WO-2020081450 | A1 * | 4/2020 | ........... A61K 31/497 |
| WO | WO 2020/167518 | A1 | 8/2020 | |
| WO | WO 2020/210508 | A1 | 10/2020 | |
| WO | WO 2020/236654 | A1 | 11/2020 | |
| WO | WO 2020/264398 | A1 | 12/2020 | |
| WO | WO 2021/021761 | A1 | 2/2021 | |
| WO | WO 2021/061853 | A1 | 4/2021 | |
| WO | WO 2021/061870 | A1 | 4/2021 | |
| WO | WO 2021/091575 | A1 | 5/2021 | |
| WO | WO 2021/113557 | A1 | 6/2021 | |
| WO | WO 2023/004163 | A1 | 1/2023 | |
| WO | WO 2023/287928 | | 1/2023 | |
| WO | WO 2023/076303 | A1 | 5/2023 | |

OTHER PUBLICATIONS

N. Rothman et al. | Biochimica et Biophysica Acta 1471 (2001).*
Sophie et al., Cancer Treatment Reviews, vol. 97, 2021, 102171 (Year: 2021).*
Liang et al., European Journal of Medicinal Chemistry, vol. 151, 2018, pp. 315-326 (Year: 2018).*
Advani et al., J Clin Oncol. Jan. 1, 2013;31(1):88-94 (Year: 2013).*
What to Expect When Having Chemotherapy. (Apr. 2021). Cancer.Net. (Year: 2021).*
Kim et al., A novel cereblon modulator for targeted protein degradation, European Journal of Medicinal Chemistry, vol. 166, 2019, pp. 65-74 (Year: 2019).*
International Search Report and Written Opinion for International Patent Application PCT/US2019/056112, 8 pages, Dec. 6, 2019.
International Search Report and Written Opinion for International Patent Application PCT/US2019/060584, 13 pages, Dec. 6, 2019.
International Search Report and Written Opinion for International Patent Application PCT/US2020/016489, 8 pages, May 27, 2020.
International Search Report and Written Opinion for International Patent Application PCT/US2020/033274, 19 pages, Oct. 23, 2020.
International Search Report and Written Opinion for International Patent Application PCT/US2020/027492, 21 pages, Aug. 11, 2020.
International Search Report and Written Opinion for International Patent Application PCT/US2020/039957, 16 pages, Oct. 5, 2020.
International Search Report and Written Opinion for International Patent Application PCT/US2020/043788, 16 pages, Oct. 23, 2020.
International Search Report and Written Opinion for International Patent Application PCT/US2020/063176, 12 pages, Mar. 5, 2021.
International Search Report and Written Opinion for International Patent Application PCT/US2020/052317, 12 pages, Apr. 1, 2021.
International Search Report and Written Opinion for International Patent Application PCT/US2020/052335, 12 pages, Apr. 1, 2021.
International Search Report and Written Opinion for International Patent Application PCT/US2022/037029, 11 pages, Oct. 10, 2022.
International Search Report and Written Opinion for International Patent Application PCT/US2022/038084, 10 pages, Oct. 11, 2022.
International Search Report and Written Opinion for International Patent Application PCT/US2022/047767, 12 pages, Feb. 6, 2023.
Bondeson et al., "Catalytic in vivo protein knockdown by small-molecule PROTACs", Nature Chemical Biology, published online Jun. 10, 2015; DOI: 10.1038/NCHEMBIO.1858.
Good et al., Proliferative tracing with single-cell mass cytometry optimizes generation of stem cell memory-like T cells, Nature Biotechnology Mar. 2019; 37(3): 259-266. DOI: 10.1038/s41587-019-0033-2.
Gosling et al.: "Abstract 2696: Genetic and pharmacologic evaluation of the ubiquitin ligase CBL-B as a small-molecule, tumor immunotherapy target I Cancer Research", Apr. 3, 2019 (Apr. 3, 2019), XP055701108, Retrieved from the Internet:U RL:https://cancerres.aacrjournals.org/content/79/13_Supplement/2696 [retrieved on Jun. 4, 2020].
Hines et al., "Posttranslational protein knockdown coupled to receptor tyrosine kinase activation with phophoPROTACs", 2013, PNAS, 110(22):8942-8947.
Howe et al, "Models of Energy in the Human Jurkat T Cell Line", Assay and Drug Development Technologies, vol. 1, No. 4, 2003, pp. 537-544.
Marshall et al., "Superior Activity of the Type C Class of ISS In Vitro and In Vivo Across Multiple Species", DNA and Cell Biology, vol. 24, No. 2, 2005, pp. 63-72.
Riling et al.: "Abstract A206: Small-molecule Cbl-b inhibitors as novel intracellular checkpoint inhibitors for cancer immunotherapy I Molecular Cancer Therapeutics", Jan. 1, 2018 (Jan. 1, 2018), XP055700949, Retrieved from the Internet:URL:https:// mct.aacrjournals.org/content/17/1_Supplement/A206 [retrieved on Jun. 4, 2020].

(56) References Cited

OTHER PUBLICATIONS

Stewart et al., "Efforts toward elucidating Thalidomide's molecular target: an expedient synthesis of the first Thalidomide biotin analogue", Org. Biomol. Chem., 2010, 8:4059-4062.

Tigno-Aranjuez et al., "Inhibition of RIP2's tyrosine kinase activity limits NOD2-driven cytokine responses", Genes & Development, 2010, 24:2666-2677; http://www.genesdev.org/cgi/doi/10.1101/gad.964410.

Yang et al., "Exploiting Synthetic Lethality for the Therapy of ABC Diffuse Large B Cell Lymphoma", Cancer Cell, 21, 2012, pp. 723-737, DOI 10.1016/j.ccr.2012.05.024.

Ye et al., "Engineered Artificial Antigen Presenting Cells Facilitate Direct and Efficient Expansion of Tumor Infiltrating Lymphocytes", Journal of Translation Medicine 2011, 9:131, 13 pages.

Gerritse et al., "High-dose administration of tyrosine kinase inhibitors to improve clinical benefit: A systematic review", Cancer Treatment Reviews, 97(2021) 102171.

Montoya et al., "Kinase-impaired BTK Mutations are susceptible to clinical-stage BTK and IKZF1/3 degrader NX-2127", Science, 383, 496 (2024) 1-13. Https://doi.org/10.1126/science.adi5798.

* cited by examiner

PIPERIDINYLPYRAZINE-CARBOXAMIDE COMPOUNDS FOR TREATING AND PREVENTING CANCER AND FOR DEGRADING BTK

CROSS-REFERENCE TO RELATED APPLICATIONS

This application claims priority to U.S. Provisional Application No. 63/263,081, filed Oct. 26, 2021, and U.S. Provisional Application No. 63/391,671, filed Jul. 22, 2022, the contents of which are hereby incorporated by reference in their entirety for all purposes.

FIELD

This disclosure provides novel bifunctional compounds for proteolytically degrading targeted Bruton's tyrosine kinases (BTK) and methods for treating diseases modulated by BTK.

BACKGROUND

B cell receptor (BCR) signaling controls B cell development, as well as mature B cell activation, signaling, and survival. Mis-regulation of the BCR signaling pathway is associated with numerous disease indications involving B cell function, and targeting B cells and BCR signaling has clear therapeutic potential (Woyach, et al.; *Blood*, 120(6); 1175-1184, 2012). For example, depletion of B cells with monoclonal antibodies targeting CD20 has significant effects in treatment of B cell malignancies and auto-immune and inflammatory diseases (Cang, et al.; *J Hematolo Oncol.* 5; 64, 2012.).

BTK is a member of the TEC family of kinases and is a crucial signaling hub in the BCR pathway. Mutations in BTK result in X-linked agammaglobulinaemia (XLA), in which B cell maturation is impaired, resulting in reduced immunoglobulin production (Hendriks, et al.; *Expert Opin Ther Targets* 15; 1002-1021, 2011). The central role of BTK in B cell signaling and function makes BTK an attractive therapeutic target for B cell malignancies as well as auto-immune and inflammatory diseases. Ibrutinib, a covalent inhibitor of BTK, has been approved to treat chronic lymphocytic leukemia (CLL), mantle cell lymphoma (MCL) and other B cell malignancies, as well as graft-versus-host disease (GvHD) (Miklos, et al.; *Blood*, 120(21); 2243-2250, 2017). Currently, ibrutinib and second-generation BTK inhibitors are being investigated for oncology and immune-related indications such as rheumatoid arthritis (Akinleye, et al.; *J of Hematolo Oncol.* 6: 59, 2013; Liu, et al.; *J Pharm and Exper Ther.* 338(1): 154-163. 2011; Di Paolo, et al.; *Nat Chem Biol.* 7(1): 41-50, 2011).

As an alternative to stoichiometric inhibition, proteolytic degradation of BTK could have dramatic consequences for B cell function by effectively blocking BCR signaling. Removal of BTK protein would eliminate BTK kinase activity as well as any protein interaction or scaffolding function of BTK. Specific degradation of BTK could be accomplished using heterobifunctional small molecules to recruit BTK to a ubiquitin ligase and thus promoting ubiquitylation and proteasomal degradation of BTK. Thalidomide derivatives, such as lenalidomide or pomalidomide, can be used to recruit potential substrates to cereblon (CRBN), a component of a ubiquitin ligase complex. This unique therapeutic approach could present a mechanism of action for interfering with BTK activity and BCR signaling that is distinct from the mechanism of stoichiometric BTK inhibition. Furthermore, this degradative approach could effectively target the C481S mutated form of BTK, which mutation has been clinically observed and confers resistance to inhibition by ibrutinib (Woyach, et al.; *Blood*, 120(6): 1175-1184, 2012.).

Presently, there remains a need for bifunctional molecules that can induce the in vivo proteolytic degradation of BTK via a ubiquitin proteolytic pathway.

SUMMARY

Provided herein are methods of using bifunctional compounds that induce the proteolytic degradation of BTK via a ubiquitin proteolysis pathway.

In one aspect, provided herein are methods of treating or preventing cancer in a human subject in need thereof. The methods comprise the step of orally administering to the human subject an amount of a bifunctional compound capable of inducing proteolytic degradation of Bruton's tyrosine kinase. In certain embodiments, the amount is effective to treat or prevent the cancer. In certain embodiments, the cancer is a hematologic malignancy. In certain embodiments, the cancer is selected from the group consisting of the cancer is selected from the group consisting of chronic lymphocytic leukemia (CLL), diffuse large B cell lymphoma (DLBCL), follicular lymphoma, mantle cell lymphoma, marginal zone lymphoma, primary central nervous system lymphoma, Waldenstrom's macroglobulinemia, and combinations thereof. In certain embodiments, the cancer is CLL. In certain embodiments, the cancer is diffuse large B-cell lymphoma. In certain embodiments, the cancer is follicular lymphoma. In certain embodiments, the cancer is mantle cell lymphoma. In certain embodiments, the cancer is marginal zone lymphoma. In certain embodiments, the cancer is primary central nervous system lymphoma. In certain embodiments, the cancer is Waldenstrom's macroglobulinemia. In certain embodiments, the bifunctional compound is a compound described herein, for instance according to Formula (I). In certain embodiments, the compound is administered at a dose of about 50 mg to about 500 mg orally. In certain embodiments, the compound is administered at a dose from about 200 mg to about 400 mg orally. In certain embodiments, the compound is administered at a dose from about 150 mg to about 350 mg orally. In certain embodiments, the compound is administered at a dose of about 50 mg, about 100 mg, about 200 mg, about 300 mg, about 400 mg, or about 500 mg orally. In certain embodiments, the dose is daily. In certain embodiments, the human subject was previously treated with a Bruton's tyrosine kinase inhibitor. In certain embodiments, the prior treatment was with ibrutinib, acalabrutinib, pirtobrutinib, or any combination thereof.

In certain embodiments, the methods comprise treatment or prevention of cancer by administration of the bifunctional compound at a dose of about 50 mg. In certain embodiments, the methods comprise treatment or prevention of cancer by administration of the bifunctional compound at a dose of about 100 mg. In certain embodiments, the methods comprise treatment or prevention of cancer by administration of the bifunctional compound at a dose of about 200 mg. In certain embodiments, the methods comprise treatment or prevention of cancer by administration of the bifunctional compound at a dose of about 300 mg. In certain embodiments, the methods comprise treatment of CLL by administration of the bifunctional compound at a dose of about 100 mg. In certain embodiments, the methods comprise treat of a non CLL cancer by administration of the bifunctional compound at a dose of about 300 mg.

In certain embodiments, the compound of formula I is administered in a form of intermittent dosing which comprises an administration period and a break period. In certain embodiments, the intermittent dosing is repeated throughout the duration of treatment or prevention of cancer. In certain embodiments, the intermittent dosing is preceded by a loading dose. In certain embodiments, the administration period is about 2 weeks, or about 3 weeks. In certain embodiments, the break period is about 1 week, or about 2 weeks. In certain embodiments, the intermittent dosing comprises of an administration period of about 2 weeks and a break period of about 2 weeks, or an administration period of about 3 weeks and a break period of about 1 week. In certain embodiments, the loading dose preceding the intermittent dosing is administered for about 4 weeks.

In another aspect, provided herein are methods of degrading Bruton's tyrosine kinase in a human subject in need thereof. The methods comprise the step of orally administering to the human subject an amount of a bifunctional compound capable of inducing proteolytic degradation of Bruton's tyrosine kinase. In certain embodiments, the amount is effective to degrade Bruton's tyrosine kinase in the subject. In certain embodiments, Bruton's tyrosine kinase is degraded by at least 80%, 85%, 90%, or 95% in the human subject In the methods, the bifunctional compounds comprise a moiety capable of specifically binding BTK and further comprise a moiety capable of recruiting an ubiquitin ligase to degrade the BTK. Particular compounds are described herein. The compounds can be administered in any form, including pharmaceutically acceptable salts and pharmaceutical compositions.

DETAILED DESCRIPTION

Figure 1:
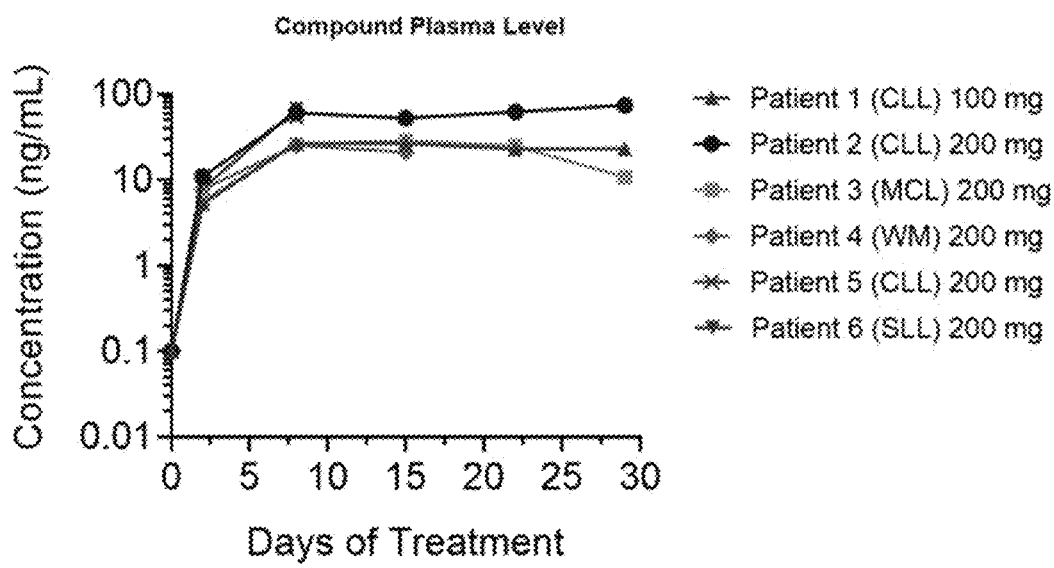
FIG. 1 provides compound plasma level following daily orally dosing at the indicated levels.

Provided herein are methods of using bifunctional compounds that induce the proteolytic degradation of Bruton's tyrosine kinase (BTK) via a ubiquitin proteolysis pathway.

As used herein, the following definitions shall apply unless otherwise indicated.

Definitions

For purposes herein, the chemical elements are identified in accordance with the Periodic Table of the Elements, CAS version, Handbook of Chemistry and Physics, 75th Ed. Additionally, general principles of organic chemistry are described in "Organic Chemistry," Thomas Sorrell, University Science Books, Sausalito: 1999, and "March's Advanced Organic Chemistry," 5th Ed., Ed.: Smith, M. B. and March, J., John Wiley & Sons, New York: 2001, the entire contents of which are hereby incorporated by reference.

As described herein, "protecting group" refers to a moiety or functionality that is introduced into a molecule by chemical modification of a functional group in order to obtain chemoselectivity in a subsequent chemical reaction. Standard protecting groups are provided in Wuts and Greene: "Greene's Protective Groups in Organic Synthesis," 4th Ed, Wuts, P. G. M. and Greene, T. W., Wiley-Interscience, New York: 2006.

As used herein, a "heterocycloalkyl" group refers to a 3-10 membered mono- or bicyclic (fused, bridged, or spiro) (e.g., 5- to 10-membered mono- or bicyclic) saturated ring structure, in which one or more of the ring atoms is a heteroatom (e.g., nitrogen (N), oxygen (O), sulfur (S), or combinations thereof). Non-limiting examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholinyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, decahydro-2,7-naphthyridine, 2,8-diazaspiro[4.5]decane, 2,7-diazaspiro[3.5]nonane, octahydropyrrolo[3,4-c]pyrrole, octahydro-1H-pyrrolo[3,4-b]pyridine, and 2,6-dioxa-tricyclo[3.3.1.0$^{3,7}$]nonyl. A monocyclic heterocycloalkyl group can be fused with a phenyl moiety to form structures, such as tetrahydroisoquinoline, that would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phospho, aliphatic (e.g., alkyl, alkenyl, or alkynyl), cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido (e.g., (aliphatic)carbonylamino, (cycloaliphatic)carbonylamino, ((cycloaliphatic) aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy (e.g., HOOC-alkoxycarbonyl, or alkylcarbonyloxy), acyl (e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl), nitro, cyano, halo, hydroxy, mercapto, sulfonyl (e.g., alkylsulfonyl or arylsulfonyl), sulfinyl (e.g., alkylsulfinyl), sulfanyl (e.g., alkylsulfanyl), sulfoxy, urea, thiourea, sulfamoyl, sulfamide, oxo, or carbamoyl.

As described herein, compounds herein optionally may be substituted with one or more substituents, such as those illustrated generally herein, or as exemplified by particular classes, subclasses, and species of the description.

As used herein, the phrase "stable or chemically feasible" refers to compounds that are not substantially altered when subjected to conditions to allow for their production, detection, and their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, New York, 537 (1970). As used herein, "patient" refers to a mammal, including a human.

As used herein, the term "about" means within +10% of a value. For example, a dose that is about 100 mg/kg provides that the dose can be 90 mg/kg to 110 mg/kg. By way of further example, an amount of an additional therapeutic agent ranging from about 50% to about 100% provides that the amount of additional therapeutic agent ranges from 45-55% to 90-110%. A person of skill in the art will appreciate the scope and application of the term "about" when used to describe other values disclosed herein.

Unless otherwise stated, structures depicted herein also are meant to include all isomeric (e.g., enantiomeric, diastereomeric, and geometric (or conformational)) forms of the structure; for example, the (R)- and (S)-configurations for each asymmetric center, (Z)- and (E)-double bond isomers, and (Z)- and (E)-conformational isomers. Therefore, single stereochemical isomers as well as enantiomeric, diastereomeric, and geometric (or conformational) mixtures of the present compounds are within the scope of the description. Alternatively, as used herein, "enantiomeric excess (ee)" refers to a dimensionless mol ratio describing the purity of chiral substances that contain, for example, a single stereogenic center. For instance, an enantiomeric excess of zero would indicate a racemic (e.g., 50:50 mixture of enantiomers, or no excess of one enantiomer over the other). By way of further example, an enantiomeric excess of ninety-nine would indicate a nearly stereopure enantiomeric compound (i.e., large excess of one enantiomer over the other). The percentage enantiomeric excess, % ee=([(R)-compound]−[(S)-compound])/([(R)-compound]+[(S)-compound])×100, where the (R)-compound>(S)-compound; or % ee=([(S)-compound]−[(R)-compound])/([(S)-compound]++[(R)-compound])×100, where the (S)-compound>(R)-compound. Moreover, as used herein, "diastereomeric excess (de)" refers to a dimensionless mol ratio describing the purity of chiral substances that contain more than one stereogenic center. For example, a diastereomeric excess of zero would indicate an equimolar mixture of diastereoisomers. By way of further example, diastereomeric excess of ninety-nine would indicate a nearly stereopure diastereomeric compound (i.e., large excess of one diastereomer over the other). Diastereomeric excess may be calculated via a similar method to ee. As would be appreciated by a person of skill, de is usually reported as percent de (% de). % de may be calculated in a similar manner to % ee.

In certain embodiments, the compounds or inhibitors described herein have an ee, de, % ee, or % de greater than zero. For example, in certain embodiments, the compounds or inhibitors described herein have an ee, de, % ee, or % de of ten. In certain embodiments, the compounds or inhibitors described herein have an ee, de, % ee, or % de of twenty-five. In certain embodiments, the compounds or inhibitors described herein have an ee, de, % ee, or % de of fifty. In certain embodiments, the compounds or inhibitors described herein have an ee, de, % ee, or % de of seventy-five.

In certain embodiments, the compounds or inhibitors described herein have an ee, de, % ee, or % de range from ninety to one hundred. In certain embodiments, the compounds or inhibitors described herein have an ee, de, % ee, or % de range from ninety-five to one hundred.

In certain embodiments, the compounds or inhibitors described herein have an ee, de, % ee, or % de range from ninety-seven to one hundred. In certain embodiments, the compounds or inhibitors described herein have an ee, de, % ee, or % de range from ninety-eight to one hundred. In certain embodiments, the compounds or inhibitors described herein have an ee, de, % ee, or % de range from ninety-nine to one hundred.

In one embodiment of a compound or inhibitor described herein, the ee, de, % ee, or % de is one. In one embodiment of a compound or inhibitor described herein, the ee, de, % ee, or % de is two. In one embodiment of a compound or inhibitor described herein, the ee, de, % ee, or % de is three. In one embodiment of a compound or inhibitor described herein, the ee, de, % ee, or % de is four. In one embodiment of a compound or inhibitor described herein, the ee, de, % ee, or % de is five. In one embodiment of a compound or inhibitor described herein, the ee, de, % ee, or % de is six. In one embodiment of a compound or inhibitor described herein, the ee, de, % ee, or % de is seven. In one embodiment of a compound or inhibitor described herein, the ee, de, % ee, or % de is eight. In one embodiment of a compound or inhibitor described herein, the ee, de, % ee, or % de is nine. In one embodiment of a compound or inhibitor described herein, the ee, de, % ee, or % de is ten. In one embodiment of a compound or inhibitor described herein, the ee, de, % ee, or % de is eleven. In one embodiment of a compound or inhibitor described herein, the ee, de, % ee, or % de is twelve. In one embodiment of a compound or inhibitor described herein, the ee, de, % ee, or % de is thirteen. In one embodiment of a compound or inhibitor described herein, the ee, de, % ee, or % de is fourteen. In one embodiment of a compound or inhibitor described herein, the ee, de, % ee, or % de is fifteen. In one embodiment of a compound or inhibitor described herein, the ee, de, % ee, or % de is sixteen. In one embodiment of a compound or inhibitor described herein, the ee, de, % ee, or % de is seventeen. In one embodiment of a compound or inhibitor described herein, the ee, de, % ee, or % de is eighteen. In one embodiment of a compound or inhibitor described herein, the ee, de, % ee, or % de is nineteen. In one embodiment of a compound or inhibitor described herein, the ee, de, % ee, or % de is twenty. In one embodiment of a compound or inhibitor described herein, the ee, de, % ee, or % de is twenty-one. In one embodiment of a compound or inhibitor described herein, the ee, de, % ee, or % de is twenty-two. In one embodiment of a compound or inhibitor described herein, the ee, de, % ee, or % de is twenty-three. In one embodiment of a compound or inhibitor described herein, the ee, de, % ee, or % de is twenty-four. In one embodiment of a compound or inhibitor described herein, the ee, de, % ee, or % de is twenty-five. In one embodiment of a compound or inhibitor described herein, the ee, de, % ee, or % de is twenty-six. In one embodiment of a compound or inhibitor described herein, the ee, de, % ee, or % de is twenty-seven. In one embodiment of a compound or inhibitor described herein, the ee, de, % ee, or % de is twenty-eight. In one embodiment of a compound or inhibitor described herein, the ee, de, % ee, or % de is twenty-nine. In one embodiment of a compound or inhibitor described herein, the ee, de, % ee, or % de is thirty. In one embodiment of a compound or inhibitor described herein, the ee, de, % ee, or % de is thirty-one. In one embodiment of a compound or inhibitor described herein, the ee, de, % ee, or % de is thirty-two. In one embodiment of a compound or inhibitor described herein, the ee, de, % ee, or % de is thirty-three. In one embodiment of a compound or inhibitor described herein, the ee, de, % ee, or % de is thirty-four. In one embodiment of a compound or inhibitor described herein, the ee, de, % ee, or % de is thirty-five. In one embodiment of a compound or inhibitor described herein, the ee, de, % ee, or % de is thirty-six. In one embodiment of a compound or inhibitor described herein, the ee, de, % ee, or % de is thirty-seven. In one embodiment of a compound or inhibitor described herein, the ee, de, % ee, or % de is thirty-eight. In one embodiment of a compound or inhibitor described herein, the ee, de, % ee, or % de is thirty-nine. In one embodiment of a compound or inhibitor described herein, the ee, de, % ee, or % de is forty. In one embodiment of a compound or inhibitor described herein, the ee, de, % ee, or % de is forty-one. In one embodiment of a compound or inhibitor described herein, the ee, de, % ee, or % de is forty-two. In one embodiment of a compound or inhibitor described herein, the ee, de, % ee, or % de is forty-three. In one embodiment of a compound or inhibitor described herein, the ee, de, % ee, or % de is forty-four. In one embodiment of a compound or inhibitor described herein, the ee, de, % ee, or % de is forty-five. In one embodiment of a compound or inhibitor described herein, the ee, de, % ee, or % de is forty-six. In one embodiment of a compound or inhibitor described herein, the ee, de, % ee, or % de is forty-seven. In one embodiment of a compound or inhibitor described herein, the ee, de, % ee, or % de is forty-eight. In one embodiment of a compound or inhibitor described herein, the ee, de, % ee, or % de is forty-nine. In one embodiment of a compound or inhibitor described herein, the ee, de, % ee, or % de is fifty. In one embodiment of a compound or inhibitor described herein, the ee, de, % ee, or % de is fifty-one. In one embodiment of a compound or inhibitor described herein, the ee, de, % ee, or % de is fifty-two. In one embodiment of a compound or inhibitor described herein, the ee, de, % ee, or % de is fifty-three. In one embodiment of a compound or inhibitor described herein, the ee, de, % ee, or % de is fifty-four. In one embodiment of a compound or inhibitor described herein, the ee, de, % ee, or % de is fifty-five. In one embodiment of a compound or inhibitor described herein, the ee, de, % ee, or % de is fifty-six. In one embodiment of a compound or inhibitor described herein, the ee, de, % ee, or % de is fifty-seven. In one embodiment of a compound or inhibitor described herein, the ee, de, % ee, or % de is fifty-eight. In one embodiment of a compound or inhibitor described herein, the ee, de, % ee, or % de is fifty-nine. In one embodiment of a compound or inhibitor described herein, the ee, de, % ee, or % de is sixty. In one embodiment of a compound or inhibitor described herein, the ee, de, % ee, or % de is sixty-one. In one embodiment of a compound or inhibitor described herein, the ee, de, % ee, or % de is sixty-two. In one embodiment of a compound or inhibitor described herein, the ee, de, % ee, or % de is sixty-three. In one embodiment of a compound or inhibitor described herein, the ee, de, % ee, or % de is sixty-four. In one embodiment of a compound or inhibitor described herein, the ee, de, % ee, or % de is sixty-five. In one embodiment of a compound or inhibitor described herein, the ee, de, % ee, or % de is sixty-six. In one embodiment of a compound or inhibitor described herein, the ee, de, % ee, or % de is sixty-seven. In one embodiment of a compound or inhibitor described herein, the ee, de, % ee, or % de is sixty-eight. In one embodiment of a compound or inhibitor described herein, the ee, de, % ee, or % de is sixty-nine. In one embodiment of a compound or inhibitor described herein, the ee, de, % ee, or % de is seventy. In one embodiment of a compound or inhibitor described herein, the ee, de, % ee, or % de is seventy-one. In one embodiment of a compound or inhibitor described herein, the ee, de, % ee, or % de is seventy-two. In one embodiment of a compound or inhibitor described herein, the ee, de, % ee, or % de is seventy-three. In one embodiment of a compound or inhibitor described herein, the ee, de, % ee, or % de is seventy-four. In one embodiment of a compound or inhibitor described herein, the ee, de, % ee, or % de is seventy-five. In one embodiment of a compound or inhibitor described herein, the ee, de, % ee, or % de is seventy-six. In one embodiment of a compound or inhibitor described herein, the ee, de, % ee, or % de is seventy-seven. In one embodiment of a compound or inhibitor described herein, the ee, de, % ee, or % de is seventy-eight. In one embodiment of a compound or inhibitor described herein, the ee, de, % ee, or % de is seventy-nine. In one embodiment of a compound or inhibitor described herein, the ee, de, % ee, or % de is eighty. In one embodiment of a compound or inhibitor described herein, the ee, de, % ee, or % de is eighty-one. In one embodiment of a compound or inhibitor described herein, the ee, de, % ee, or % de is eighty-two. In one embodiment of a compound or inhibitor described herein, the ee, de, % ee, or % de is eighty-three. In one embodiment of a compound or inhibitor described herein, the ee, de, % ee, or % de is eighty-four. In one embodiment of a compound or inhibitor described herein, the ee, de, % ee, or % de is eighty-five. In one embodiment of a compound or inhibitor described herein, the ee, de, % ee, or % de is eighty-six. In one embodiment of a compound or inhibitor described herein, the ee, de, % ee, or % de is eighty-seven. In one embodiment of a compound or inhibitor described herein, the ee, de, % ee, or % de is eighty-eight. In one embodiment of a compound or inhibitor described herein, the ee, de, % ee, or % de is eighty-nine. In one embodiment of a compound or inhibitor described herein, the ee, de, % ee, or % de is ninety. In one embodiment of a compound or inhibitor described herein, the ee, de, % ee, or % de is ninety-one. In one embodiment of a compound or inhibitor described herein, the ee, de, % ee, or % de is ninety-two. In one embodiment of a compound or inhibitor described herein, the ee, de, % ee, or % de is ninety-three. In one embodiment of a compound or inhibitor described herein, the ee, de, % ee, or % de is ninety-four. In one embodiment of a compound or inhibitor described herein, the ee, de, % ee, or % de is ninety-five. In one embodiment of a compound or inhibitor described herein, the ee, de, % ee, or % de is ninety-six. In one embodiment of a compound or inhibitor described herein, the ee, de, % ee, or % de is ninety-seven. In one embodiment of a compound or inhibitor described herein, the ee, de, % ee, or % de is ninety-eight. In one embodiment of a compound or inhibitor described herein, the ee, de, % ee, or % de is ninety-nine In one embodiment of a compound or inhibitor described herein, the ee, de, % ee, or % de is one hundred. In certain embodiments, compounds or inhibitors described herein have an ee, de, % ee, or % de as described within this paragraph. In certain embodiments, a compound according to Formula (I) or Table 1, as described in the Examples and/or Biological Examples, has an ee, de, % ee, or % de as described within this paragraph. Unless otherwise stated, all tautomeric forms of the compounds of the description are within the scope of the description. Additionally, unless otherwise stated, structures depicted herein also are meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this description. Such compounds are useful, for example, as analytical tools or probes in biological assays, or as therapeutic agents.

As used herein, the term "&1" means that a compound including the "&1" notation at a particular chemical element or atom (e.g., carbon) within the compound was prepared as a mixture of two stereoisomers at the noted chemical element or atom (e.g., a diastereomeric mixture having a de or % de as described above).

Chemical structures and nomenclature are derived from ChemDraw, version 11.0.1, Cambridge, MA.

It is noted that the use of the descriptors "first," "second," "third," or the like is used to differentiate separate elements (e.g., solvents, reaction steps, processes, reagents, or the like) and may or may not refer to the relative order or relative chronology of the elements described.

Uses of the Compounds and Compositions

The bifunctional compounds described herein are useful for degrading BTK in biological samples or in patients via an ubiquitin proteolytic pathway. Thus, an embodiment of this disclosure provides a method of treating a BTK-mediated disease or disorder. As used herein, the term "BTK-mediated disease or disorder" means any disease, disorder, or other deleterious condition in which a BTK is known to play a role. In some instances, a BTK-mediated disease or disorder is a proliferative disorder or an autoimmune disorder. Examples of proliferative disorders include cancer.

In one aspect, provided herein are methods of treating or preventing cancer in a subject in need thereof. In certain embodiments, the methods comprise the step of orally administering to the subject an amount of a bifunctional compound capable of inducing proteolytic degradation of Bruton's tyrosine kinase. In certain embodiments, the amount is effective to treat or prevent the cancer. In certain embodiments, the bifunctional compound is compound 149. In certain embodiments, the bifunctional compound is compound 195.

In certain embodiments, provided herein are methods of treating or preventing cancer in a human subject in need thereof. The methods comprise the step of orally administering to the human subject an amount of a bifunctional compound capable of inducing proteolytic degradation of Bruton's tyrosine kinase. In certain embodiments, the amount is effective to treat or prevent the cancer. In certain embodiments, the BTK mutant is C481S. In certain embodiments, the dose is daily. In certain embodiments, the human subject was previously treated with a Bruton's tyrosine kinase inhibitor. In certain embodiments, the prior treatment was with ibrutinib, acalabrutinib, pirtobrutinib, or any combination thereof.

In certain embodiments, the cancer is any cancer deemed appropriate for treatment by the practitioner of skill. In particular embodiments, the cancer comprises a solid tumor. In certain embodiments, the cancer is a hematologic malignancy. In certain embodiments, the cancer is a B cell malignancy. In certain embodiments, the cancer is selected from the group consisting of the cancer is selected from the group consisting of chronic lymphocytic leukemia (CLL), diffuse large B cell lymphoma (DLBCL), follicular lymphoma, mantle cell lymphoma, marginal zone lymphoma, primary central nervous system lymphoma, Waldenstrom's macroglobulinemia, and combinations thereof. In certain embodiments, the cancer is CLL. In certain embodiments, the cancer is diffuse large B-cell lymphoma. In certain embodiments, the cancer is follicular lymphoma. In certain embodiments, the cancer is mantle cell lymphoma. In certain embodiments, the cancer is marginal zone lymphoma. In certain embodiments, the cancer is primary central nervous system lymphoma. In certain embodiments, the cancer is Waldenstrom's macroglobulinemia.

In certain embodiments, the subject has a mutant Bruton's tyrosine kinase. In certain embodiments, the subject has a C481S, L528W, M437R, or V416L mutant Bruton's tyrosine kinase, or a combination thereof. In certain embodiments, the subject has a C481S mutant Bruton's tyrosine kinase. In certain embodiments, the subject has a L528W mutant Bruton's tyrosine kinase. In certain embodiments, the subject has a M437R mutant Bruton's tyrosine kinase. In certain embodiments, the subject has a V416L mutant Bruton's tyrosine kinase. In certain embodiments, the subject has a mutation that renders the resulting Bruton's tyrosine kinase to lack appreciable kinase activity. In certain embodiments, the subject has a mutation that renders the resulting Bruton's tyrosine kinase to lack measurable kinase activity.

In certain embodiments, the cancer is resistant to a BTK inhibitor. In certain embodiments, the cancer is resistant to ibrutinib, acalabrutinib, pirtobrutinib, or any combination thereof. In certain embodiments, the cancer is relapsed/refractory leukemia. In certain embodiments the cancer is relapse CLL. Those of skill will recognize that certain resistant cancers express a C481 mutant Bruton's tyrosine kinase, for instance C481S Bruton's tyrosine kinase. For example, in certain embodiments, the subject has a C481 mutant Bruton's tyrosine kinase and the cancer is chronic lymphocytic leukemia (CLL). In addition, certain resistant cancers express a mutant Bruton's tyrosine kinase such as L528W wherein the mutant BTK lacks measurable kinase activity. In certain embodiments, the human subject was previously treated with a BTK inhibitor. In certain embodiments, the prior treatment was with ibrutinib, acalabrutinib, pirtobrutinib, or any combination thereof. In certain embodiments, the prior treatment was with ibrutinib. In certain embodiments, the prior treatment was with acalabrutinib. In certain embodiments, the prior treatment was with pirtobrutinib. In certain embodiments, the prior treatment was with ibrutinib, acalabrutinib, and pirtobrutinib.

In certain embodiments, compounds described herein are capable of treating patients with a disease selected from the group consisting of Waldenstrom's macroglobulinemia, primary central nervous system lymphoma (PCNSL), marginal zone lymphoma (MZL), mantle cell lymphoma (MCL), DLBCL, follicular lymphoma, and CLL. In certain embodiments, the disease is Waldenstrom's macroglobulinemia. In certain embodiments, the disease is PCNSL. In certain embodiments, the disease is MZL. In certain embodiments, the disease is MCL. In certain embodiments, the disease is DLBCL. In certain embodiments, the disease is follicular lymphoma. In certain embodiments, the disease is CLL.

In certain embodiments, the compound of formula I is administered for the treatment or prevention of cancer such as diffuse large B cell lymphoma. In certain embodiments, the cancer being treated or prevented is germinal center B-cell-like (GCB) DLBCL. In certain embodiments, the cancer being treated or prevented is non-GCB DLBCL. In certain embodiments, the cancer being treated or prevented is activated B-cell-like (ABC) DLBCL, a subtupe of non-GCB DLBCL.

In another aspect, provided herein are methods of degrading Bruton's tyrosine kinase in a subject in need thereof. The methods comprise the step of orally administering to the subject an amount of a bifunctional compound capable of inducing proteolytic degradation of Bruton's tyrosine kinase. In certain embodiments, the amount is effective to degrade Bruton's tyrosine kinase in the subject. The Bruton's tyrosine kinase can be expressed in any cells or tissues of the subject. In certain embodiments, the Bruton's tyrosine kinase is expressed in splenocytes. In certain embodiments, the Bruton's tyrosine kinase is expressed in peripheral blood mononuclear cells. In certain embodiments, the Bruton's tyrosine kinase is expressed in circulating B cells. In certain embodiments, the amount is effective to degrade Bruton's tyrosine kinase in the subject. In certain embodiments, Bruton's tyrosine kinase is degraded by at least 80%, 85%, 90%, or 95% in the human subject. In certain embodiments, the degradation is relative to baseline levels in the subject. In certain embodiments, levels are measured in splenocytes, plasma, peripheral mononuclear cells, or circulating B cells. Levels can be measured by standard techniques including immunoassays, ELISA, and FRET-immunoassays. Exemplary techniques are described herein. In certain embodiments, the bifunctional compound is compound 149. In certain embodiments, the bifunctional compound is compound 195.

The bifunctional compound can be administered in any dose deemed suitable by the practitioner of skill. In certain embodiments, the dose is 0.1-1000 mg/kg. In certain embodiments, the dose is 0.1-900 mg/kg. In certain embodiments, the dose is 0.1-800 mg/kg. In certain embodiments, the dose is 0.1-700 mg/kg. In certain embodiments, the dose is 0.1-600 mg/kg. In certain embodiments, the dose is 0.1-500 mg/kg. In certain embodiments, the dose is 0.1-400 mg/kg. In certain embodiments, the dose is 0.1-300 mg/kg. In certain embodiments, the dose is 0.1-200 mg/kg. In certain embodiments, the dose is 0.1-100 mg/kg. In certain embodiments, the dose is selected from the group consisting of 100 mg/kg, 200 mg/kg, 300 mg/kg, 450 mg/kg, 600 mg/kg, 800 mg/kg, and 1000 mg/kg. In certain embodiments, the dose is about 25 mg/kg. In certain embodiments, the dose is about 50 mg/kg. In certain embodiments, the dose is about 75 mg/kg. In certain embodiments, the dose is about 100 mg/kg. In certain embodiments, the dose is about 150 mg/kg. In certain embodiments, the dose is about 200 mg/kg. In certain embodiments, the dose is about 250 mg/kg. In certain embodiments, the dose is about 300 mg/kg. In certain embodiments, the dose is about 400 mg/kg. In certain embodiments, the dose is about 450 mg/kg. In certain embodiments, the dose is about 500 mg/kg. In certain embodiments, the dose is about 600 mg/kg. In certain embodiments, the dose is about 700 mg/kg. In certain embodiments, the dose is about 750 mg/kg. In certain embodiments, the dose is about 800 mg/kg. In certain embodiments, the dose is about 900 mg/kg. In certain embodiments, the dose is about 1000 mg/kg.

In certain embodiments, the compound is administered at a dose of about 50 mg to about 500 mg orally. In certain embodiments, the compound is administered at a dose from about 200 mg to about 400 mg orally. In certain embodiments, the compound is administered at a dose from about 150 mg to about 350 mg orally. In certain embodiments, the compound is administered at a dose of about 50 mg orally. In certain embodiments, the compound is administered at a dose of about 100 mg orally. In certain embodiments, the compound is administered at a dose of about 200 mg orally. In certain embodiments, the compound is administered at a dose of about 300 mg orally. In certain embodiments, the compound is administered at a dose of about 400 mg orally. In certain embodiments, the compound is administered at a dose of about 500 mg orally.

In certain embodiments, the methods comprise treatment of CLL by administration of the bifunctional compound at a dose of about 100 mg. In certain embodiments, the methods comprise treat of a non CLL cancer by administration of the bifunctional compound at a dose of about 300 mg. In certain embodiments, the bifunctional compound is compound number 149. In certain embodiments, the bifunctional compound is compound 195.

In certain embodiments, the methods comprise treatment or prevention of cancer by administration of compound number 149. In certain embodiments, compound 149 is administered at a dose of about 50 mg to about 500 mg orally. In certain embodiments, compound 149 is administered at a dose from about 200 mg to about 400 mg orally. In certain embodiments, compound 149 is administered at a dose from about 150 mg to about 350 mg orally. In certain embodiments, compound 149 is administered at a dose of about 50 mg, about 100 mg, about 200 mg, about 300 mg, about 400 mg, or about 500 mg orally. In certain embodiments, compound 149 is administered at a dose of about 300 mg for the treatment or prevention of cancer. In certain embodiments, the dose is daily. In certain embodiments, compound 149 is administered for the treatment or prevention of cancer such as chronic lymphocytic leukemia (CLL). In certain embodiments, compound 149 is administered at a dose of about 100 mg for the treatment or prevention of CLL.

In certain embodiments, the methods comprise treatment or prevention of cancer by administration of compound number 195. In certain embodiments, compound 195 is administered at a dose of about 50 mg to about 500 mg orally. In certain embodiments, compound 195 is administered at a dose from about 200 mg to about 400 mg orally. In certain embodiments, compound 195 is administered at a dose from about 150 mg to about 350 mg orally. In certain embodiments, compound 195 is administered at a dose of about 50 mg, about 100 mg, about 200 mg, about 300 mg, about 400 mg, or about 500 mg orally. In certain embodiments, compound 195 is administered at a dose of about 100 mg for the treatment or prevention of cancer. In certain embodiments, the dose is daily. In certain embodiments, compound 195 is administered for the treatment or prevention of cancer such as chronic lymphocytic leukemia (CLL). In certain embodiments, compound 195 is administered at a dose of about 50 mg for the treatment or prevention of CLL. In certain embodiments, compound 195 is administered at a dose of about 100 mg for the treatment or prevention of CLL.

The dose can be administered on a schedule deemed suitable by the person of skill in the art. In certain embodiments, the dose is administered once per day. In certain embodiments, the dose is administered twice per day. In certain embodiments, the dose is administered three times per day. In certain embodiments, the dose is administered four times per day. In certain embodiments, the dose is administered in divided doses. In certain embodiments, the dose is administered in two divided doses per day. In certain embodiments, the dose is administered in three divided doses per day. In certain embodiments, the dose is administered in four divided doses per day.

Dosing can continue for any length of time deemed suitable by the person of skill in the art. In certain embodiments, the dose is administered daily for thirty days or more. In certain embodiments, the dose is administered daily for fifteen days. In certain embodiments, the dose is administered daily for fourteen days. In certain embodiments, the dose is administered daily for thirteen days. In certain embodiments, the dose is administered daily for twelve days. In certain embodiments, the dose is administered daily for eleven days. In certain embodiments, the dose is administered daily for ten days. In certain embodiments, the dose is administered daily for nine days. In certain embodiments, the dose is administered daily for eight days. In certain embodiments, the dose is administered daily for seven days. In certain embodiments, the dose is administered daily for six days. In certain embodiments, the dose is administered daily for five days. In certain embodiments, the dose is administered daily for four days. In certain embodiments, the dose is administered daily for three days. In certain embodiments, the dose is administered daily for two days. In certain embodiments, the dose is administered for one day.

In the dosing schedule, the doses can be administered on consecutive days or cyclicly, according to the judgment of the practitioner of skill. In certain embodiments, the doses are administered on consecutive days. In certain embodiments, the doses are administered with an interval between doses. In certain embodiments, the interval is one day. In certain embodiments, the interval is two days. In certain embodiments, the interval is three days. In certain embodiments, the interval is four days. In certain embodiments, the interval is five days. In certain embodiments, the interval is six days.

In certain embodiments, the dose is administered weekly. In certain embodiments, the dose is administered twice per week. In certain embodiments, the dose is administered three times per week.

In certain embodiments, the dose(s) are administered for a period of time with a first interval between dose(s), and then the dose(s) are re-administered for a period of time following the first interval between dose(s), wherein this dosing regimen can be repeated (i.e., cyclicly or cyclically, for example, after a second, third, etc. interval between subsequent administrations of dose(s)) according to the judgment of the practitioner of skill. For example, in one embodiment, a first dose is administered for one week, followed by a first interval of one week without the first dose administration; then, a second dose is re-administered for another week, followed by a second interval of one week without the first or second dose administration, and so on cyclically. Other perturbations for first, second, third, etc. dose(s) followed by perturbations for first, second, third, etc. interval(s), and combinations thereof, are contemplated herein as would be appreciated by the practitioner of skill and the need of the patient. For example, in one embodiment, a first dose is administered daily for one week, followed by a first interval of three weeks without the first daily dose administration; then, a second dose is re-administered biweekly for another week, followed by a second interval of four weeks without the first daily or second biweekly dose administration, and so on cyclically.

In certain embodiments, the compound of formula I is administered in a form of intermittent dosing which comprises an administration period and a break period. In certain embodiments, administration period is a period of time wherein the compound of formula I is administered daily to the human subject. In certain embodiments, the break period is a period of time wherein the compound of formula I is not administered to the human subject for the entire duration of the break period. In certain embodiments, the intermittent dosing is repeated throughout the duration of treatment or prevention of cancer. In certain embodiments, the intermittent dosing is preceded by a loading dose. In certain embodiments, the administration period is about 0.5 to about 6 weeks. In certain embodiments, the administration period is about 1 to about 5 weeks. In certain embodiments, the administration period is about 2 to about 4 weeks. In certain embodiments, the administration period is about 0.5 week, about 1 week, about 2 weeks, about 3 weeks, about 4 weeks, about 5 weeks, or about 6 weeks. In certain embodiments, the administration period is about 2 weeks. In certain embodiments, the administration period is about 3 weeks. In certain embodiments, the break period is about 0.5 to about 6 weeks. In certain embodiments, the break period is about 1 to about 5 weeks. In certain embodiments, the break period is about 2 to about 4 weeks. In certain embodiments, the break period is about 0.5 week, about 1 week, about 2 weeks, about 3 weeks, about 4 weeks, about 5 weeks, or about 6 weeks. In certain embodiments, the break period is about 2 weeks. In certain embodiments, the break period is about 1 week. In certain embodiments, the intermittent dosing comprises of an administration period of about 2 weeks and a break period of about 2 weeks. In certain embodiments, the intermittent dosing comprises of an administration period of about 3 weeks and a break period of about 1 week. In certain embodiments, the loading dose preceding the intermittent dosing is administered for about 1 to about 7 weeks. In certain embodiments, the loading dose is administered for about 2 to about 6 weeks. In certain embodiments, the loading dose is administered for about 3 to about 5 weeks. In certain embodiments, the loading dose is administered for about 1 week, about 2 weeks, about 3 weeks, about 4 weeks, about 5 weeks, about 6 weeks, or about 7 weeks. In certain embodiments, the loading dose is administered for about 4 weeks.

The compound can be administered by any route of administration deemed suitable by the practitioner of skill. In certain embodiments, the dose is administered orally. Formulations and techniques for administration are described in detail below.

In certain embodiments, term "cancer" includes, but is not limited to, the following cancers: epidermoid Oral: buccal cavity, lip, tongue, mouth, pharynx, squamous cell carcinoma of the head and neck (HNSCC); Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell lung cancer (NSCLC); Gastrointestinal: gastric cancer, esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, microsatellite stable colorectal cancer (MSS CRC), rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma), metastatic castrate-resistant prostate cancer (mCRPC), muscle-invasive urothelial cancer; Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma (MM), malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical cancer, cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast, triple-negative breast cancer (TNBC), platinum-resistant epithelial ovarian cancer (EOC); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders (e.g., mantle cell lymphoma, Waldenström's macroglobulinemia, Marginal zone lymphoma, and Follicular lymphoma); Skin: malilymphgnant melanoma, basal cell carcinoma, squamous cell carcinoma, Karposi's sarcoma, keratoacanthoma, moles dysplastic nevi, lipoma, angioma, dermatofibroma, keloids, psoriasis; Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; Adrenal glands: neuroblastoma; and metatstaic melanoma.

Examples of autoimmune disorders include uticaria, graft-versus-host disease (GVHD), acute graft-versus-host disease, pemphigus vulgaris, achalasia, Addison's disease, Adult Still's disease, agammaglobulinemia, alopecia areata, amyloidosis, ankylosing spondylitis, anti-GBM/anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, axonal and neuronal neuropathy (AMAN), Baló disease, Behcet's disease, benign mucosal pemphigoid, bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss Syndrome (CSS) or Eosinophilic Granulomatosis (EGPA), cicatricial pemphigoid, Cogan's syndrome, cold agglutinin disease, congenital heart block, coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hidradenitis suppurativa (HS) (Acne Inversa), hypogammalglobulinemia, IgA nephropathy, IgG4-related sclerosing disease, immune thrombocytopenic purpura (ITP), inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, lichen planus, lichen sclerosus, ligneous conjunctivitis, linear IgA disease (LAD), lupus, lyme disease chronic, Meniere's disease, microscopic polyangiitis (MPA), mixed connective tissue disease (MCTD), Mooren's ulcer, Mucha-Habermann disease, Multifocal Motor Neuropathy (MMN) or MMNCB, multiple sclerosis, myasthenia gravis, myositis, narcolepsy, neonatal lupus, neuromyelitis optica, neutropenia, ocular cicatricial pemphigoid, optic neuritis, palindromic rheumatism (PR), PANDAS, paraneoplastic cerebellar degeneration (PCD), paroxysmal nocturnal hemoglobinuria (PNH), Parry Romberg syndrome, pars planitis (peripheral uveitis), Parsonnage-Turner syndrome, pemphigus, peripheral neuropathy, perivenous encephalomyelitis, pernicious anemia (PA), POEMS syndrome, polyarteritis nodosa, polyglandular syndromes type I, II, III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive Arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjögren's syndrome, sperm and testicular autoimmunity, stiff person syndrome (SPS), subacute bacterial endocarditis (SBE), Susac's syndrome, sympathetic ophthalmia (SO), Takayasu's arteritis, temporal arteritis (giant cell arteritis), thrombocytopenic purpura (TTP), Tolosa-Hunt syndrome (THS), transverse myelitis, Type 1 diabetes, ulcerative colitis (UC), undifferentiated connective tissue disease (UCTD), uveitis, vasculitis, vitiligo, Vogt-Koyanagi-Harada Disease, and Wegener's granulomatosis (or Granulomatosis with Polyangiitis (GPA)).

The bifunctional compound can be any bifunctional compound described herein. In certain embodiments, the compound is according to Formula I:

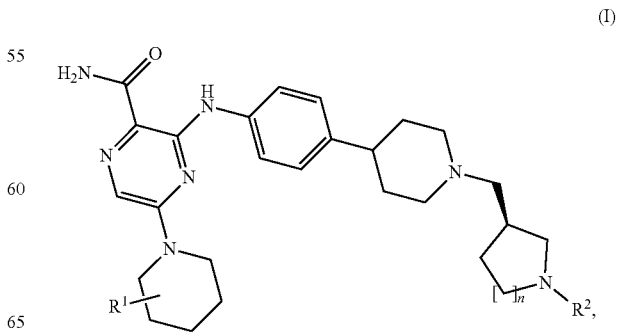

wherein R¹ is selected from hydrogen and substituted or unsubstituted heterocycle;

R² is selected from

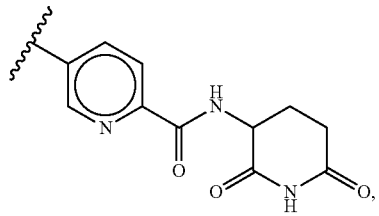

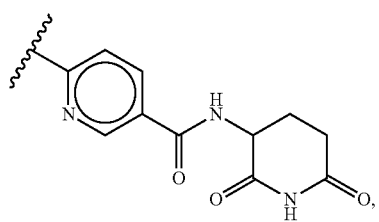

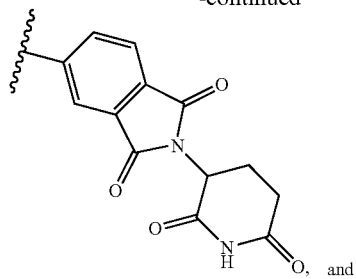

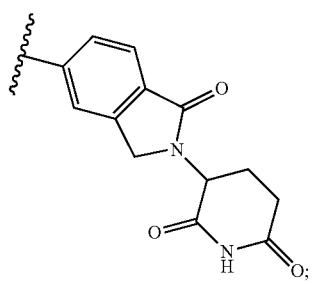

and n is 1 or 2; or
or a pharmaceutically acceptable salt thereof.

In particular embodiments, the bifunctional compound is compound 149. In particular embodiments, the bifunctional compound is compound 195.

TABLE 1

Example compounds and/or pharmaceutically acceptable salts thereof for use in the methods described herein.

| Compound Number | Structure |
|---|---|
| 32 | 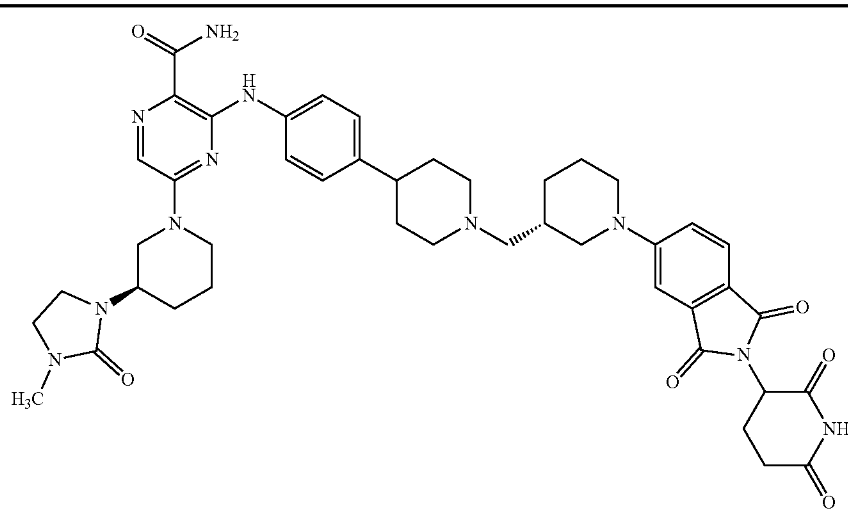 |

TABLE 1-continued

Example compounds and/or pharmaceutically acceptable salts thereof for use in the methods described herein.

| Compound Number | Structure |
|---|---|
| 87 | 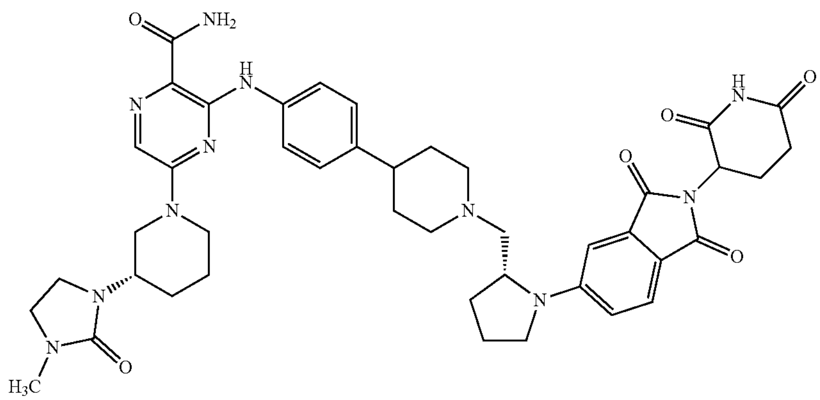 [SMILES: CN1CCN([C@H]2CCCN(c3cnc(C(N)=O)c(Nc4ccc(C5CCN(C[C@H]6CCCN6c6ccc7c(c6)C(=O)N(C6CCC(=O)NC6=O)C7=O)CC5)cc4)n3)C2)C1=O] |
| 89 | 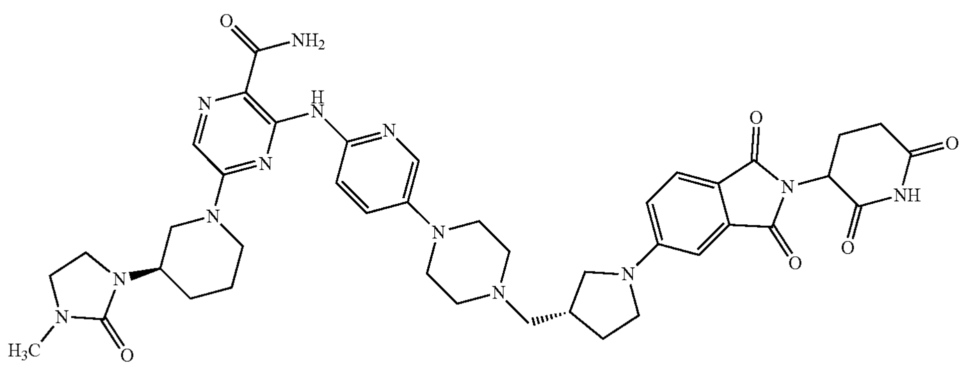 [SMILES: CN1CCN([C@@H]2CCCN(c3cnc(C(N)=O)c(Nc4ccc(N5CCN(C[C@H]6CCN(c7ccc8c(c7)C(=O)N(C7CCC(=O)NC7=O)C8=O)C6)CC5)cn4)n3)C2)C1=O] |
| 125 | 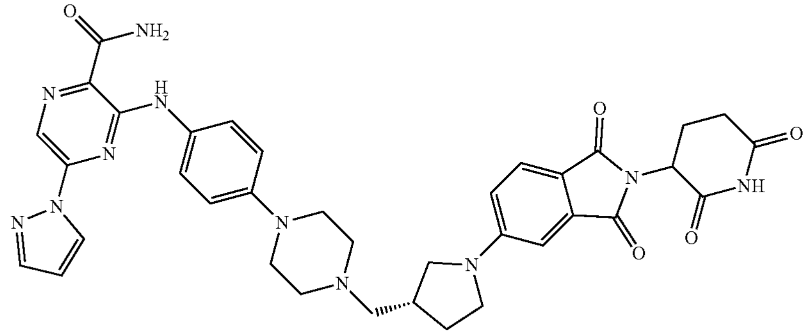 [SMILES: NC(=O)c1ncc(-n2cccn2)nc1Nc1ccc(N2CCN(C[C@H]3CCN(c4ccc5c(c4)C(=O)N(C4CCC(=O)NC4=O)C5=O)C3)CC2)cc1] |
| 126 | 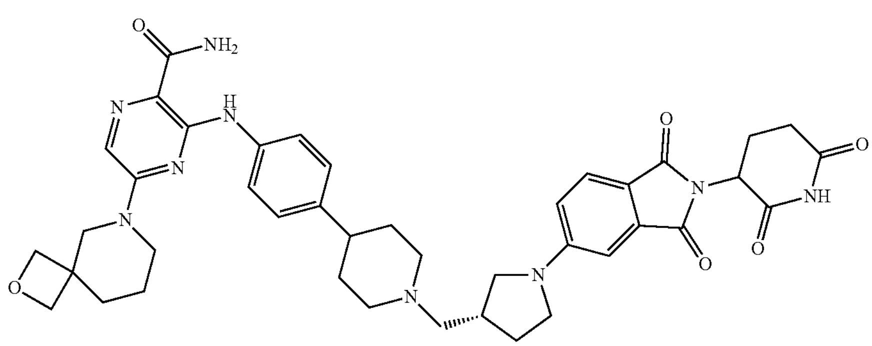 [SMILES: NC(=O)c1ncc(N2CCCC3(COC3)C2)nc1Nc1ccc(C2CCN(C[C@H]3CCN(c4ccc5c(c4)C(=O)N(C4CCC(=O)NC4=O)C5=O)C3)CC2)cc1] |

TABLE 1-continued

Example compounds and/or pharmaceutically acceptable salts thereof for use
in the methods described herein.

| Compound Number | Structure |
|---|---|
| 128 | 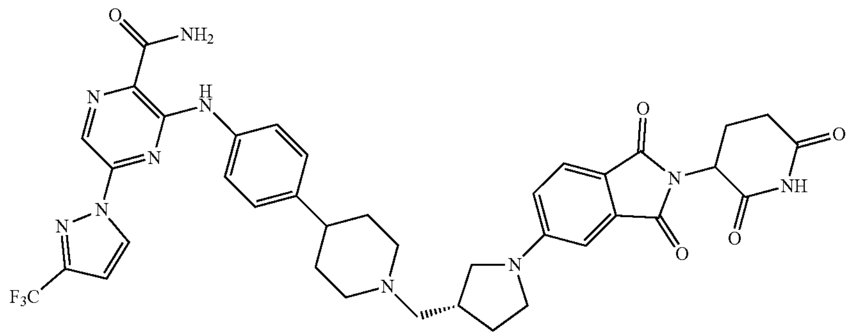 [SMILES: NC(=O)c1ncc(-n2ccc(C(F)(F)F)n2)nc1Nc1ccc(C2CCN(C[C@H]3CCN(c4ccc5c(c4)C(=O)N(C4CCC(=O)NC4=O)C5=O)C3)CC2)cc1] |
| 130 | 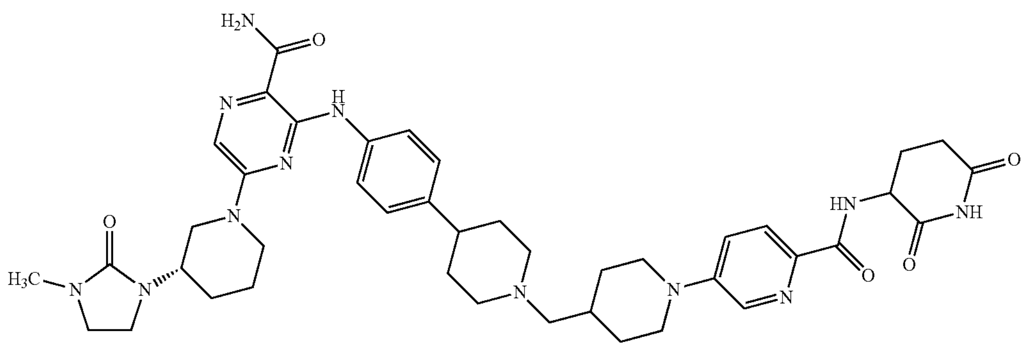 [SMILES: CN1CCN([C@H]2CCCN(c3cnc(C(N)=O)c(Nc4ccc(C5CCN(CC6CCN(c7ccc(C(=O)NC8CCC(=O)NC8=O)nc7)CC6)CC5)cc4)n3)C2)C1=O] |
| 146 | 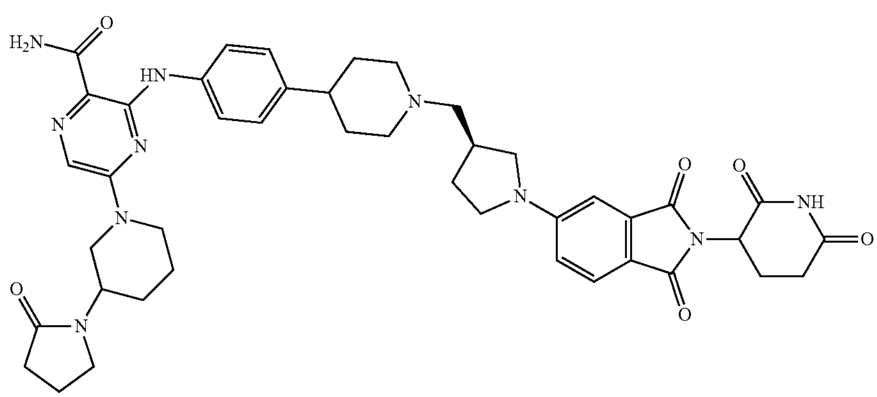 [SMILES: NC(=O)c1ncc(N2CCCC(N3CCCC3=O)C2)nc1Nc1ccc(C2CCN(C[C@@H]3CCN(c4ccc5c(c4)C(=O)N(C4CCC(=O)NC4=O)C5=O)C3)CC2)cc1] |
| 148 | 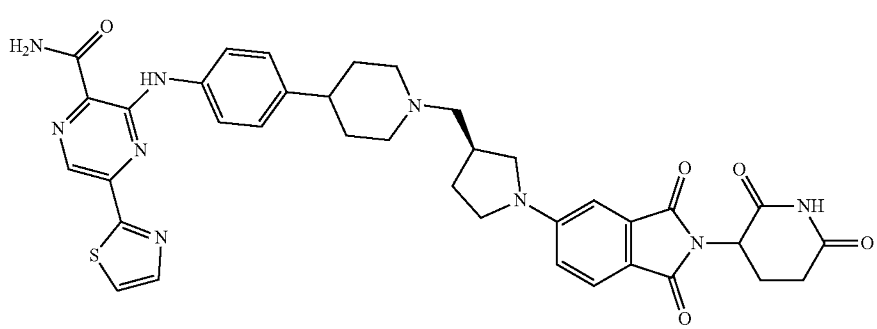 [SMILES: NC(=O)c1ncc(-c2nccs2)nc1Nc1ccc(C2CCN(C[C@@H]3CCN(c4ccc5c(c4)C(=O)N(C4CCC(=O)NC4=O)C5=O)C3)CC2)cc1] |

TABLE 1-continued

Example compounds and/or pharmaceutically acceptable salts thereof for use in the methods described herein.

| Compound Number | Structure |
|---|---|
| 149 | 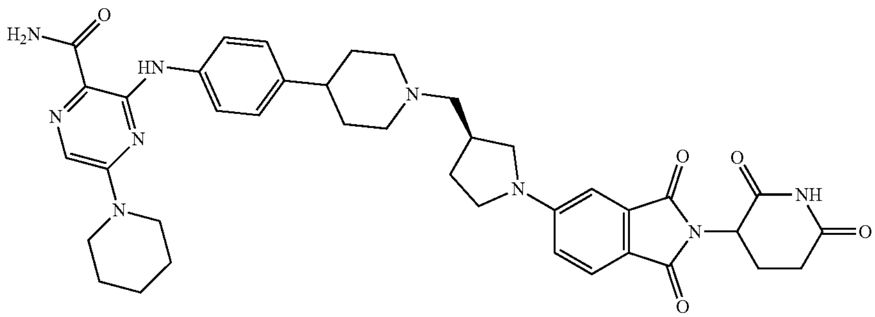 [SMILES: NC(=O)c1ncc(N2CCCCC2)nc1Nc1ccc(C2CCN(C[C@@H]3CCN(c4ccc5c(c4)C(=O)N(C4CCC(=O)NC4=O)C5=O)C3)CC2)cc1] |
| 152 | 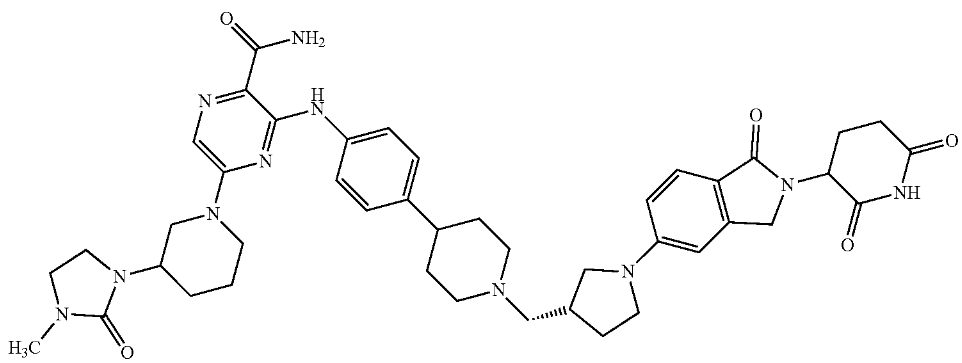 |
| 156 | 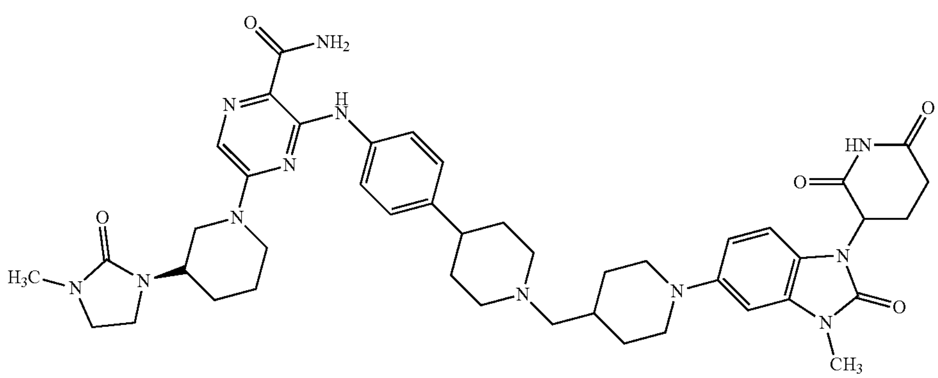 |
| 157 | 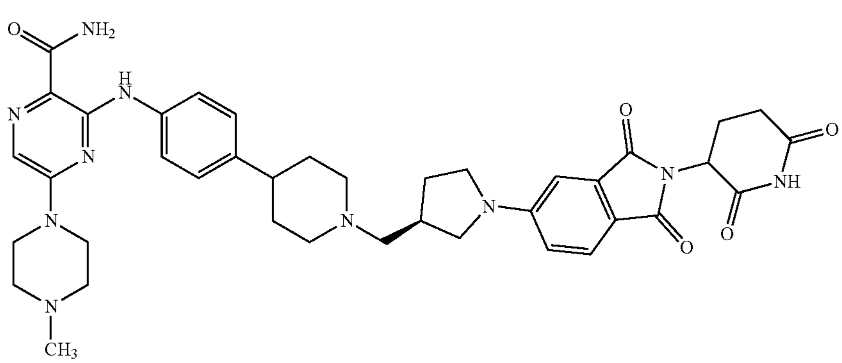 [SMILES: CN1CCN(c2cnc(C(N)=O)c(Nc3ccc(C4CCN(C[C@H]5CCN(c6ccc7c(c6)C(=O)N(C6CCC(=O)NC6=O)C7=O)C5)CC4)cc3)n2)CC1] |

TABLE 1-continued

Example compounds and/or pharmaceutically acceptable salts thereof for use in the methods described herein.

| Compound Number | Structure |
|---|---|
| 159 | 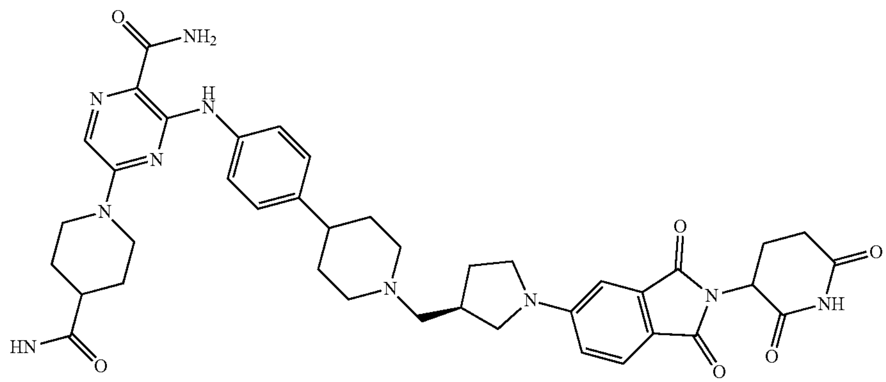 [SMILES: NC(=O)c1ncc(N2CCC(C(N)=O)CC2)nc1Nc1ccc(C2CCN(C[C@H]3CCN(c4ccc5c(c4)C(=O)N(C4CCC(=O)NC4=O)C5=O)C3)CC2)cc1] |
| 160 | 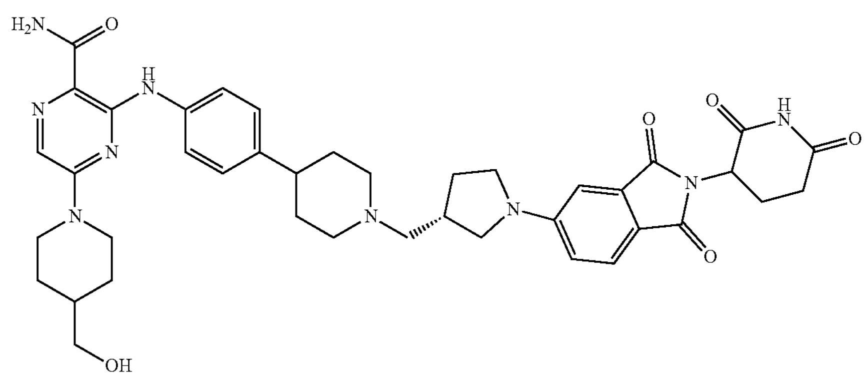 [SMILES: NC(=O)c1ncc(N2CCC(CO)CC2)nc1Nc1ccc(C2CCN(C[C@@H]3CCN(c4ccc5c(c4)C(=O)N(C4CCC(=O)NC4=O)C5=O)C3)CC2)cc1] |
| 161 | 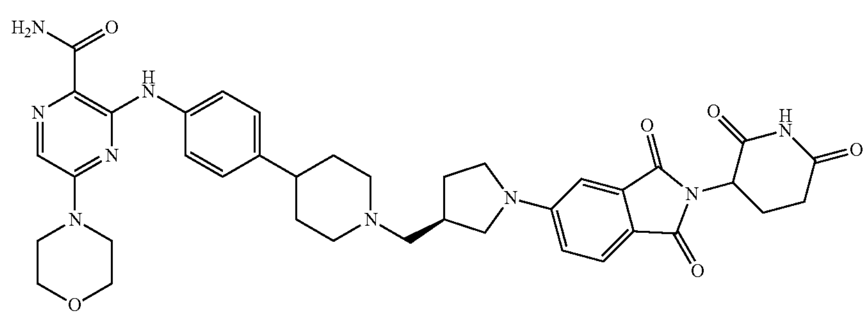 [SMILES: NC(=O)c1ncc(N2CCOCC2)nc1Nc1ccc(C2CCN(C[C@H]3CCN(c4ccc5c(c4)C(=O)N(C4CCC(=O)NC4=O)C5=O)C3)CC2)cc1] |
| 173 | 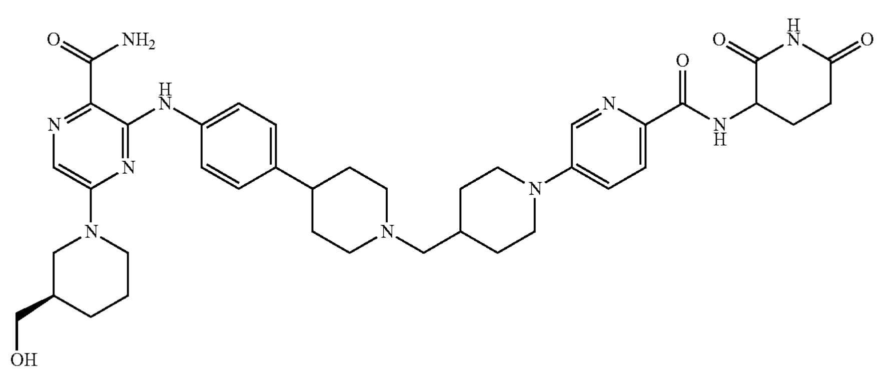 [SMILES: NC(=O)c1ncc(N2CCC[C@@H](CO)C2)nc1Nc1ccc(C2CCN(CC3CCN(c4ccc(C(=O)NC5CCC(=O)NC5=O)nc4)CC3)CC2)cc1] |

TABLE 1-continued

Example compounds and/or pharmaceutically acceptable salts thereof for use in the methods described herein.

| Compound Number | Structure |
| --- | --- |
| 174 | 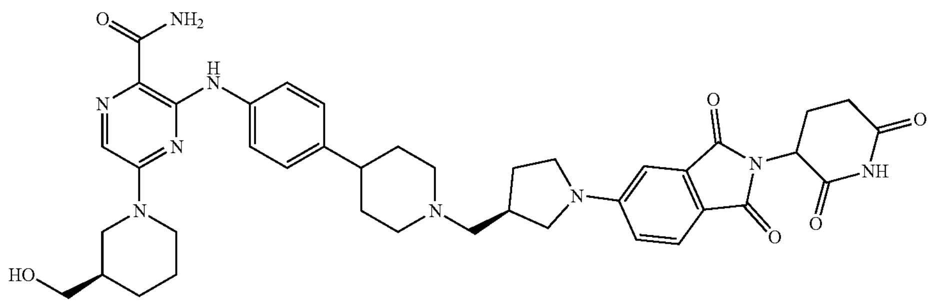 [SMILES: NC(=O)c1ncc(N2CCC[C@@H](CO)C2)nc1Nc1ccc(C2CCN(C[C@H]3CCN(c4ccc5c(c4)C(=O)N(C4CCC(=O)NC4=O)C5=O)C3)CC2)cc1] |
| 175 | 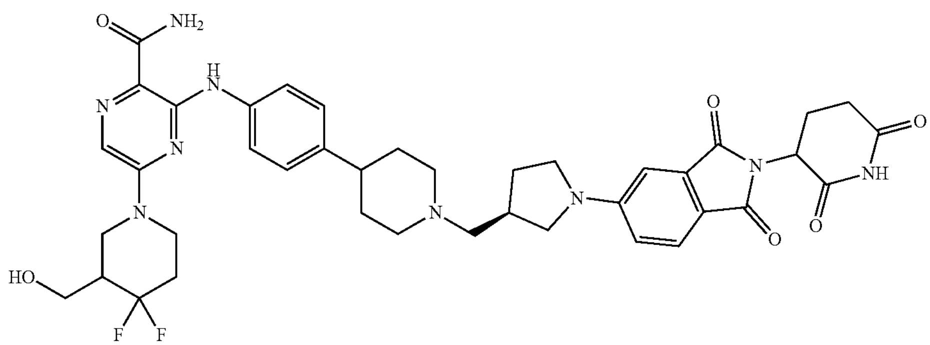 [SMILES: NC(=O)c1ncc(N2CCC(F)(F)C(CO)C2)nc1Nc1ccc(C2CCN(C[C@H]3CCN(c4ccc5c(c4)C(=O)N(C4CCC(=O)NC4=O)C5=O)C3)CC2)cc1] |
| 176 | 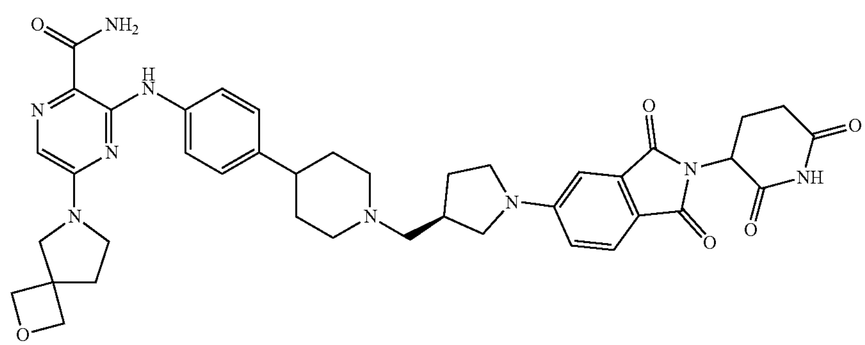 [SMILES: NC(=O)c1ncc(N2CCC3(COC3)C2)nc1Nc1ccc(C2CCN(C[C@H]3CCN(c4ccc5c(c4)C(=O)N(C4CCC(=O)NC4=O)C5=O)C3)CC2)cc1] |
| 193 | 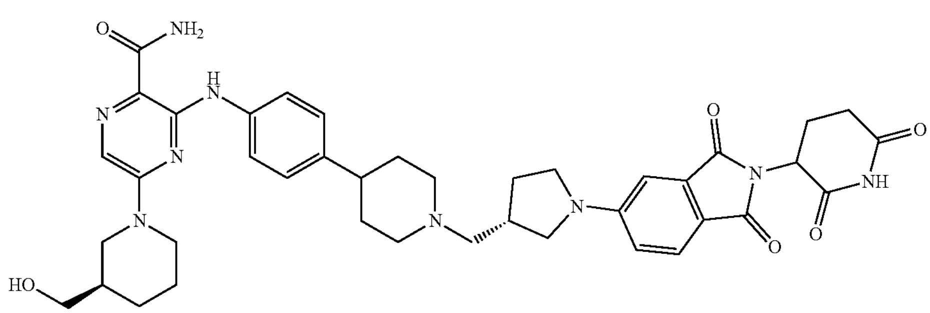 [SMILES: NC(=O)c1ncc(N2CCC[C@@H](CO)C2)nc1Nc1ccc(C2CCN(C[C@@H]3CCN(c4ccc5c(c4)C(=O)N(C4CCC(=O)NC4=O)C5=O)C3)CC2)cc1] |

TABLE 1-continued

Example compounds and/or pharmaceutically acceptable salts thereof for use in the methods described herein.

| Compound Number | Structure |
|---|---|
| 194 | 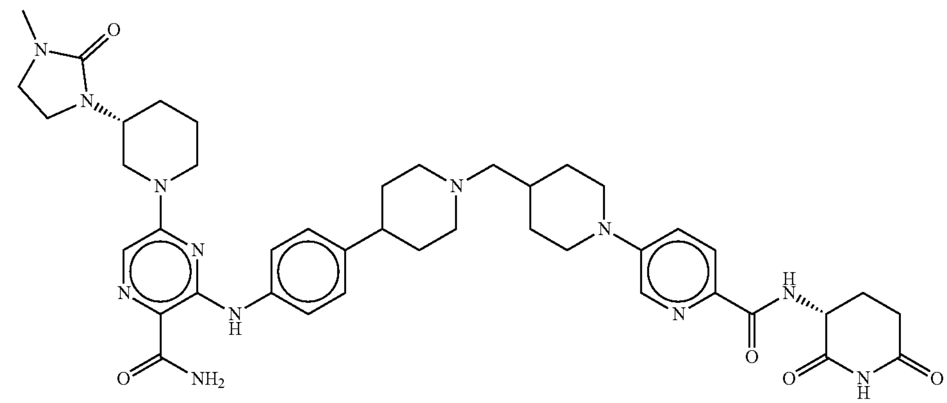 |
| 195 | 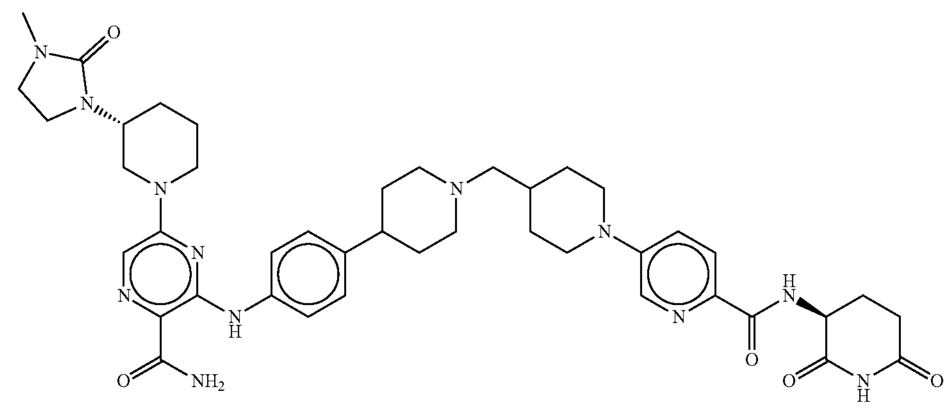 |
| 196 | 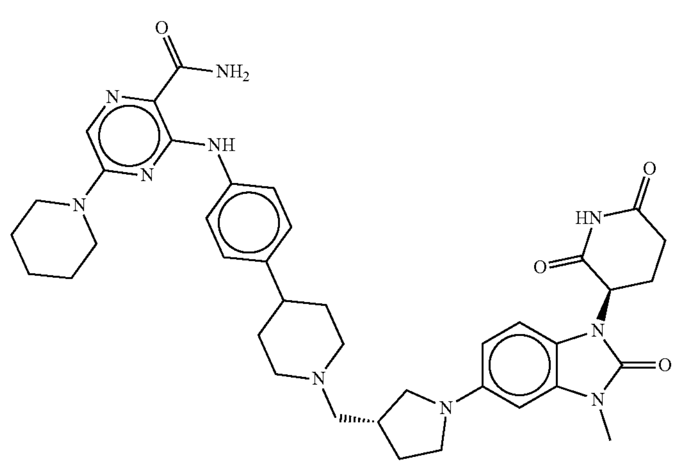 |

TABLE 1-continued

Example compounds and/or pharmaceutically acceptable salts thereof for use
in the methods described herein.

| Compound Number | Structure |
| --- | --- |
| 197 | 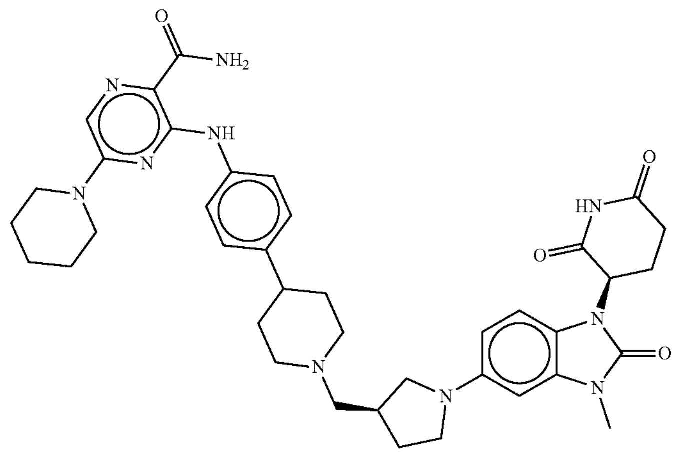 |
| 198 | 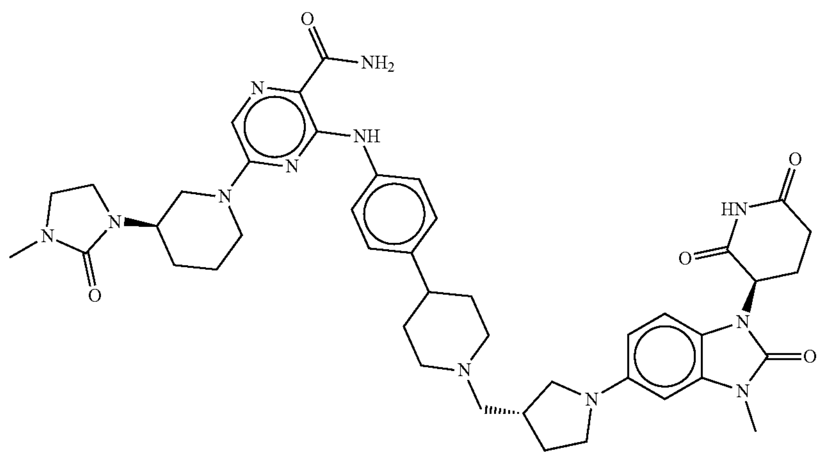 |
| 199 | 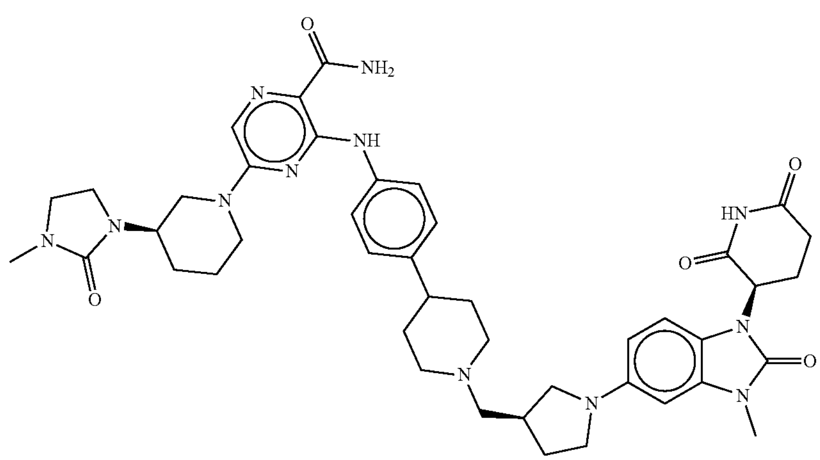 |

TABLE 1-continued

Example compounds and/or pharmaceutically acceptable salts thereof for use in the methods described herein.

| Compound Number | Structure |
| --- | --- |
| 204 | [Chemical structure] | and pharmaceutically acceptable salts thereof.

Formulations and Administration
Pharmaceutical Compositions

The compounds described herein can be formulated into pharmaceutical compositions that further comprise a pharmaceutically acceptable carrier, diluent, adjuvant, or vehicle. In one embodiment, this disclosure provides a pharmaceutical composition comprising a compound described above, and a pharmaceutically acceptable carrier, diluent, adjuvant, or vehicle. In one embodiment, this disclosure is a pharmaceutical composition comprising an effective amount of a compound of this disclosure or a pharmaceutically acceptable salt thereof and a pharmaceutically acceptable carrier, diluent, adjuvant, or vehicle. Pharmaceutically acceptable carriers include, for example, pharmaceutical diluents, excipients, or carriers suitably selected with respect to the intended form of administration, and consistent with conventional pharmaceutical practices.

According to another embodiment, the description provides a composition comprising a compound herein or a pharmaceutically acceptable salt thereof and a pharmaceutically acceptable carrier, adjuvant, or vehicle. Pharmaceutical compositions of this description comprise a therapeutically effective amount of a compound of described herein wherein a "therapeutically effective amount" is an amount that is (a) effective to measurably degrade BTK (or reduce the amount of BTK) in a biological sample or in a patient; or (b) effective in treating and/or ameliorating a disease or disorder that is mediated by BTK.

The term "patient," as used herein, means an animal, alternatively a mammal, and alternatively a human.

It also will be appreciated that certain compounds of this disclosure can exist in free form for treatment, or where appropriate, as a pharmaceutically acceptable derivative (e.g., a salt) thereof. According to this disclosure, a pharmaceutically acceptable derivative includes, but is not limited to, pharmaceutically acceptable prodrugs, salts, esters, salts of such esters, or any other adduct/educt or derivative that upon administration to a patient in need is capable of providing, directly or indirectly, a compound as otherwise described herein, or a metabolite or residue thereof.

As used herein, the term "pharmaceutically acceptable salt" refers to those salts that are, within the scope of sound medical judgement, suitable for use in contact with the tissues of humans and lower animals without undue toxicity, irritation, allergic response, and the like.

Pharmaceutically acceptable salts are well known in the art. For example, S. M. Berge et al., describe pharmaceutically acceptable salts in detail in *J. Pharmaceutical Sciences* 1977, 66, 1-19, incorporated herein by reference. Pharmaceutically acceptable salts of the compounds of this description include those derived from suitable inorganic and organic acids and bases. Examples of pharmaceutically acceptable, nontoxic acid addition salts include salts of an amino group formed with inorganic acids such as hydrochloric acid, hydrobromic acid, phosphoric acid, sulfuric acid, and perchloric acid; or with organic acids such as acetic acid, oxalic acid, maleic acid, tartaric acid, citric acid, succinic acid, or malonic acid; or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_1\text{-}4 \text{ alkyl})_4$ salts. This description also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A pharmaceutically acceptable carrier may contain inert ingredients that do not unduly inhibit the biological activity of the compounds. The pharmaceutically acceptable carriers should be biocompatible, for example, non-toxic, non-inflammatory, non-immunogenic, or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants, and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, the use of such conventional carrier medium is contemplated to be within the scope of this description. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful, uncomfortable, or risky. Side effects include, but are not limited to, fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain, and headache), hair loss, asthenia, dizziness, extra-pyramidal symptoms, akathisia, cardiovascular disturbances, and sexual dysfunction.

Some examples of materials that can serve as pharmaceutically acceptable carriers include, but are not limited to, ion exchangers, alumina, aluminum stearate, lecithin, serum proteins (such as human serum albumin), buffer substances (such as tween 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring, and perfuming agents. Preservatives and antioxidants can also be present in the composition, according to the judgment of the formulator.

As used herein, the term "measurably degrade," means a measurable reduction in (a) BTK activity, between a sample comprising a compound of this description and a BTK and an equivalent sample comprising a BTK in the absence of said compound; or (b) the concentration of the BTK in a sample over time.

Administration

The compositions of this disclosure are administered orally. The pharmaceutically acceptable compositions of this description may be orally administered in any orally acceptable dosage form including, but not limited to, capsules, tablets, aqueous suspensions, or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring, or coloring agents also may be added.

Liquid dosage forms for oral administration include, but are not limited to, pharmaceutically acceptable emulsions, microemulsions, solutions, suspensions, syrups, and elixirs. In addition to the active compounds herein, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions also can include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound herein is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets, and pills, the dosage form also may comprise buffering agents.

Solid compositions of a similar type also may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Solid dosage forms optionally may contain opacifying agents. These solid dosage forms also can be of a composition such that they release the active ingredient(s) only, for example, in a certain part of the intestinal tract, optionally, in a delayed manner. Examples of embedding compositions that can be used include polymeric substances and waxes. Solid compositions of a similar type also may be employed as fillers in soft and hard-filled gelatin capsules using such excipients as lactose or milk sugar as well as high molecular weight polethylene glycols and the like.

The active compounds herein also can be in microencapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose, or starch. Such dosage forms also may comprise, as is normal practice, additional substances other than inert diluents, for example, tableting lubricants and other tableting aids such a magnesium stearate and microcrystalline cellulose. In the case of capsules, tablets and pills, the dosage forms also may comprise buffering agents. They may optionally contain opacifying agents and also can be of a composition such that they release the active ingredient(s) only, for example, in a certain part of the intestinal tract, optionally, in a delayed manner. Examples of embedding compositions that can be used include polymeric substances and waxes.

The compounds of the description are formulated in dosage unit form for ease of administration and uniformity of dosage. As used herein, the phrase "dosage unit form" refers to a physically discrete unit of agent appropriate for the patient to be treated. It will be understood, however, that the total daily usage of the compounds and compositions of this disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex, and diet of the patient; the time of administration, route of administration, and rate of excretion of the specific compound employed; the duration of the treatment; drugs used in combination or coincidental with the specific compound employed, and like factors well known in the medical arts.

The amount of the compounds of this disclosure that may be combined with the carrier materials to produce a composition in a single dosage form will vary depending upon the host treated, the particular mode of administration, and other factors. The compositions should be formulated so that a dosage of between 0.01-100 mg/kg body weight/day of the compound or inhibitor can be administered to a patient receiving these compositions.

Depending upon the particular condition, or disease, to be treated or prevented, additional therapeutic agents, which are normally administered to treat or prevent that condition, also may be present in the compositions of this disclosure. As used herein, additional therapeutic agents that are normally administered to treat or prevent a particular disease, or condition, are known as "appropriate for the disease, or condition, being treated."

For example, chemotherapeutic agents or other anti-proliferative agents may be combined with the compounds of this disclosure to treat proliferative diseases and cancer. Examples of known chemotherapeutic agents include, but are not limited to, PI3K inhibitors (e.g., idelalisib and copanlisib), BCL-2 inhibitors (e.g., venetoclax), BTK inhibitors (e.g., ibrutinib and acalabrutinib), etoposide, CD20 antibodies (e.g., rituximab, ocrelizumab, obinutuzumab, ofatumumab, ibritumomab tiuxetan, tositumomab, and ublituximab), aletuzumab, bendamustine, cladribine, doxorubicin, chlorambucil, prednisone, midostaurin, lenalidomide, pomalidomide, checkpoint inhibitors (e.g., ipilimumab, nivolumab, pembolizumab, atezolizumab, avelumab, durvalumab), engineered cell therapy (e.g., CAR-T therapy-Kymriah®, Yescarta®), Gleevec™, adriamycin, dexamethasone, vincristine, cyclophosphamide, fluorouracil, topotecan, taxol, interferons, and platinum derivatives.

And, in some instances, radiation therapy is administered during the treatment course wherein a compound of this disclosure (or a pharmaceutically acceptable salt thereof) is administered to a patient in need thereof.

Other examples of agents with which the compounds or inhibitors of this disclosure also may be combined include, without limitation, treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this disclosure will be no more than the amount that would normally be administered in a composition comprising that therapeutic agent as the only active agent. The amount of additional therapeutic agent in the presently disclosed compositions will range from about 50% to 100% of the amount normally present in a composition comprising that agent as the only therapeutically active agent.

EXAMPLES

Additional embodiments are disclosed in further detail in the following examples, which are not in any way intended to limit the scope of the claims The compounds described herein are synthesized according to PCT/US2019/56112, filed Oct. 14, 2019, PCT/US2020/063176, filed Dec. 30, 2020, US2021/0198280 A1, filed Dec. 30, 2020, or consistent with the Examples below. The contents of each of these references are incorporated herein in their entireties.

Example 1: General Procedure B

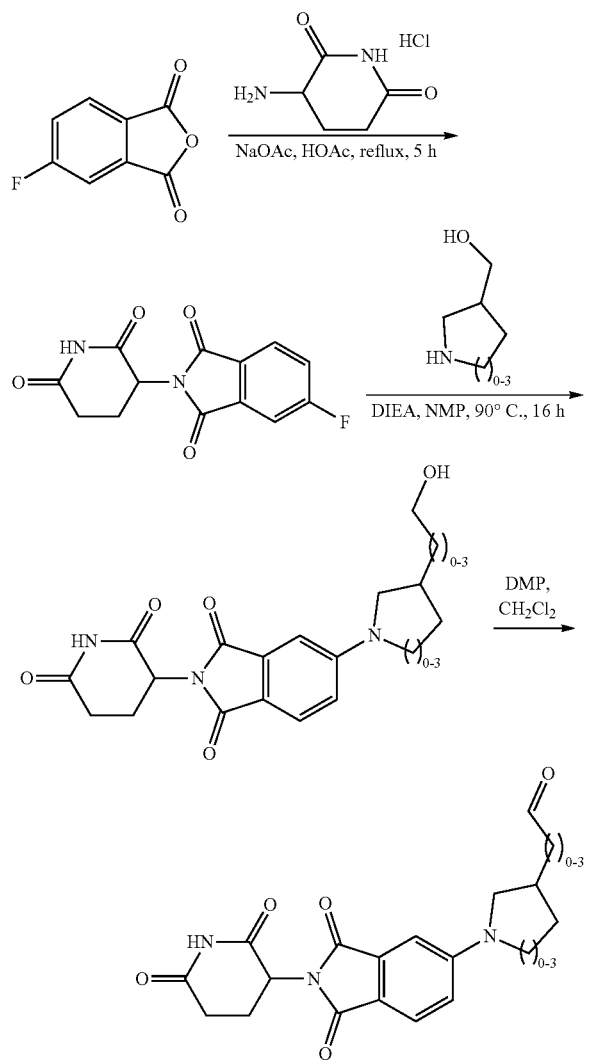

Step 1: 2-(2,6-dioxopiperidin-3-yl)-5-fluoroisoindoline-1,3-dione.

A mixture of 5-fluoro-1,3-dihydro-2-benzofuran-1,3-dione (5.0 g, 30.10 mmol), 3-aminopiperidine-2,6-dione hydrochloride (6.9 g, 42.14 mmol) and NaOAc (4.2 g, 51.17 mmol) in HOAc (50 mL) was stirred at 120° C. for 5 h before concentrated under vacuum. The residue was washed with water and the solid was collected by filtration. The crude product was washed with water twice and ethyl acetate twice and dried under oven to afford 2-(2,6-dioxopiperidin-3-yl)-5-fluoroisoindoline-1,3-dione (7.7 g, 92%) as a light brown solid. $^1$H NMR (300 MHz, DMSO-$d_6$) δ 11.16 (s, 1H), 8.03-8.00 (m, 1H), 7.87-7.85 (m, 1H), 7.75-7.70 (m, 1H), 5.19-5.15 (m, 1H), 2.94-2.86 (m, 1H), 2.63-2.48 (m, 2H), 2.12-2.06 (m, 1H). F NMR (300 MHz, DMSO-$d_6$) δ −102.078.

Step 2: Amine Displacement of Aryl Fluoride.

To a solution of 2-(2,6-dioxopiperidin-3-yl)-5-fluoro-2,3-dihydro-1H-isoindole-1,3-dione (1.0 g, 3.62 mmol) in N-Methyl pyrrolidone (10 mL) were added the amine (3.60 mmol) and DIEA (1.4 g, 10.83 mmol). The resulting solution was stirred at 80° C. for 16 h. The reaction mixture was cooled down to room temperature and purified by reverse phase flash chromatography to afford the corresponding final product.

Step 3: Alcohol Oxidation to the Aldehyde.

To a mixture of the alcohol (1.06 mmol) in $CH_2Cl_2$ (10 mL) was added Dess-Martin periodinane (2.12 mmol). The mixture was allowed to stir at room temperature for 1 h. The mixture was purified by column chromatography to afford the desired aldehyde.

Example 1A: Synthesis of 2-(1-(2-(2,6-dioxopiperidin-3-yl)-1,3-dioxoisoindolin-5-yl)piperidin-4-yl)acetaldehyde

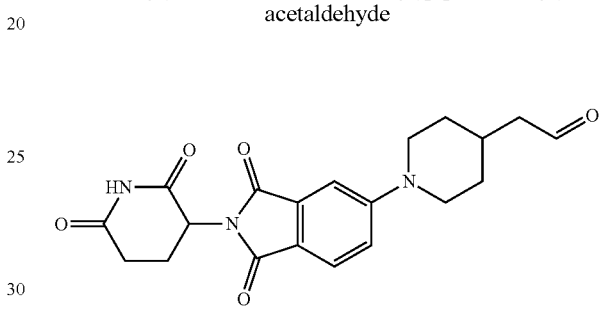

Step 2: Followed General Procedure B with 2-(piperidin-4-yl)ethan-1-ol to afford 2-(2,6-dioxopiperidin-3-yl)-5-(4-(2-hydroxyethyl)piperidin-1-yl)isoindoline-1,3-dione (822.8 mg, 59%) as a yellow solid. $^1$H NMR (300 MHz, DMSO-$d_6$) δ 11.09 (s, 1H), 7.65 (d, J=8.4 Hz, 1H), 7.30 (d, J=2.4 Hz, 1H), 7.23 (dd, J=8.4, 2.4 Hz, 1H), 5.07 (dd, J=12.6, 5.4 Hz, 1H), 4.40 (t, J=5.1 Hz, 1H), 4.04 (d, J=13.2 Hz, 2H), 3.64-3.40 (m, 2H), 3.09-2.79 (m, 3H), 2.70-2.51 (m, 2H), 2.07-1.94 (m, 1H), 1.77-1.66 (m, 3H), 1.41-1.34 (m, 2H), 1.24-1.12 (m, 2H). MS (ESI) calc'd for ($C_{20}H_{23}N_3O_5$) [M+H]$^+$, 386.2; found 386.1.

Step 3: 2-(1-(2-(2,6-dioxopiperidin-3-yl)-1,3-dioxoisoindolin-5-yl)piperidin-4-yl)acetaldehyde LCMS $C_{20}H_{21}N_3O_5$ requires: 383, found: m/z=384 [M+H]$^+$.

Example 1B: Synthesis of 1-(2-(2,6-dioxopiperidin-3-yl)-1,3-dioxoisoindolin-5-yl)azetidine-3-carbaldehyde

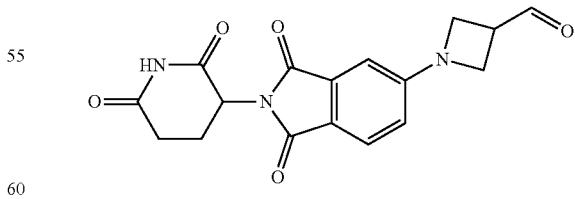

Step 2: Followed General Procedure B with azetidin-3-ylmethanol hydrochloride to afford 2-(2,6-dioxopiperidin-3-yl)-5-(3-(hydroxymethyl)azetidin-1-yl)isoindoline-1,3-dione (1.85 g, 68%) as a yellow solid. $^1$H NMR (400 MHz, DMSO-$d_6$) δ 11.09 (s, 1H), 7.63 (d, J=8.4 Hz, 1H), 6.76 (d, J=2.0 Hz, 1H), 6.62 (dd, J=8.4, 2.0 Hz, 1H), 5.06 (dd, J=12.4, 5.2 Hz, 1H), 4.86 (t, J=5.2 Hz, 1H), 4.05 (t, J=8.4 Hz, 2H), 3.77 (dd, J=8.4, 5.2 Hz, 2H), 3.60 (t, J=5.2 Hz, 2H), 3.00-2.81 (m, 2H), 2.65-2.53 (m, 2H), 2.06-1.96 (m, 1H). MS (ESI) calc'd for ($C_{17}H_{17}N_3O_5$) [M+H]$^+$, 344.1; found 344.4.

Step 3: 1-(2-(2,6-dioxopiperidin-3-yl)-1,3-dioxoisoindolin-5-yl)azetidine-3-carbaldehyde LCMS $C_{17}H_{15}N_3O_5$ requires: 341, found: m/z=343 [M+H]$^+$.

Example 1C: Synthesis of 2-(1-(2-(2,6-dioxopiperidin-3-yl)-1,3-dioxoisoindolin-5-yl)azetidin-3-yl)acetaldehyde

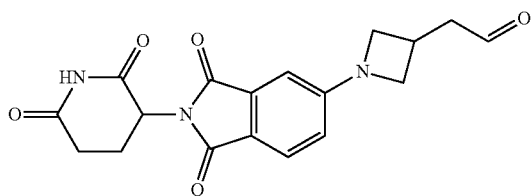 [SMILES: O=CCC1CN(c2ccc3c(c2)C(=O)N(C2CCC(=O)NC2=O)C3=O)C1]

Step 2: Followed General Procedure B with 2-(azetidin-3-yl)ethan-1-ol hydrochloride to afford 2-(2,6-dioxopiperidin-3-yl)-5-(3-(2-hydroxyethyl)azetidin-1-yl)isoindoline-1,3-dione (584.5 mg, 30%) as a yellow solid. $^1$H NMR (300 MHz, DMSO-d$_6$) δ 11.09 (s, 1H), 7.63 (d, J=8.4 Hz, 1H), 6.75 (d, J=2.1 Hz, 1H), 6.62 (dd, J=8.4, 2.1 Hz, 1H), 5.06 (dd, J=12.6, 5.4 Hz, 1H), 4.51 (t, J=5.1 Hz, 1H), 4.14 (t, J=8.1 Hz, 2H), 3.71-3.67 (m, 2H), 3.47-3.40 (m, 2H), 2.99-2.75 (m, 2H), 2.61-2.58 (m, 1H), 2.52-2.46 (m, 1H), 2.10-1.95 (m, 1H), 1.82-1.76 (m, 2H). MS (ESI) calc'd for ($C_{18}H_{19}N_3O_5$) [M+H]$^+$, 358.1; found 358.4.

Step 3: 2-(1-(2-(2,6-dioxopiperidin-3-yl)-1,3-dioxoisoindolin-5-yl)azetidin-3-yl)acetaldehyde LCMS $C_{18}H_{17}N_3O_5$ requires: 355, found: m/z=356 [M+H]$^+$.

Example 1I: Synthesis of (3R)-1-(2-(2,6-dioxopiperidin-3-yl)-1,3-dioxoisoindolin-5-yl)piperidine-3-carbaldehyde

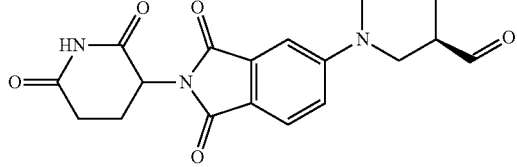

Step 2: Followed General Procedure B with (R)-piperidin-3-ylmethanol hydrochloride to afford 2-(2,6-dioxopiperidin-3-yl)-5-((R)-3-(hydroxymethyl)piperidin-1-yl)isoindoline-1,3-dione (916.3 mg, 45%) as a yellow solid. $^1$H NMR (400 MHz, DMSO-d$_6$/D$_2$O) δ 7.62 (d, J=8.4 Hz, 1H), 7.22 (d, J=2.4 Hz, 1H), 7.16 (dd, J=8.4, 2.4 Hz, 1H), 4.99 (dd, J=12.8, 5.2 Hz, 1H), 3.98-3.76 (m, 2H), 3.42-3.22 (m, 2H), 3.08-2.90 (m, 1H), 2.89-2.71 (m, 2H), 2.61-2.43 (m, 2H), 2.02-1.99 (m, 1H), 1.73-1.69 (m, 3H), 1.49-1.40 (m, 1H), 1.26-1.18 (m, 1H). MS (ESI) calc'd for ($C_{19}H_{21}N_3O_5$) [M+H]$^+$, 372.1; found 372.1.

Step 3: (3R)-1-(2-(2,6-dioxopiperidin-3-yl)-1,3-dioxoisoindolin-5-yl)piperidine-3-carbaldehyde LCMS $C_{19}H_{19}N_3O_5$ requires: 369, found: m/z=370 [M+H]$^+$.

Example 1E: Synthesis of (3S)-1-(2-(2,6-dioxopiperidin-3-yl)-1,3-dioxoisoindolin-5-yl)piperidine-3-carbaldehyde

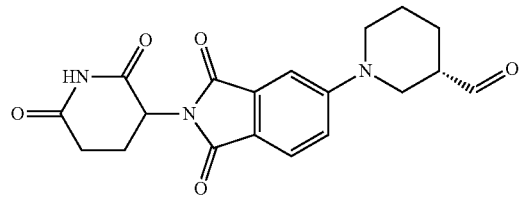 [SMILES: O=C[C@H]1CCCN(c2ccc3c(c2)C(=O)N(C2CCC(=O)NC2=O)C3=O)C1]

Step 2: Followed General Procedure B with (S)-piperidin-3-ylmethanol hydrochloride to afford 2-(2,6-dioxopiperidin-3-yl)-5-((S)-3-(hydroxymethyl)piperidin-1-yl)isoindoline-1,3-dione (493.1 mg, 73%) as a yellow solid. $^1$H NMR (300 MHz, DMSO-d$_6$/D$_2$O) δ 7.65 (d, J=8.4 Hz, 1H), 7.26 (d, J=2.1 Hz, 1H), 7.19 (dd, J=8.4, 2.1 Hz, 1H), 5.04 (dd, J=12.9, 5.4 Hz, 1H), 4.00-3.90 (m, 2H), 3.38-3.32 (m, 2H), 3.13-2.71 (m, 3H), 2.67-2.44 (m, 2H), 2.03-1.98 (m, 1H), 1.76-1.67 (m, 3H), 1.57-1.38 (m, 1H), 1.34-1.10 (m, 1H). MS (ESI) calc'd for ($C_{19}H_{21}N_3O_5$) [M+H]$^+$, 372.1; found 372.1.

Step 3: (3S)-1-(2-(2,6-dioxopiperidin-3-yl)-1,3-dioxoisoindolin-5-yl)piperidine-3-carbaldehyde LCMS $C_{19}H_{19}N_3O_5$ requires: 369, found: m/z=370 [M+H]$^+$.

Example 1F: Synthesis of (3R)-1-(2-(2,6-dioxopiperidin-3-yl)-1,3-dioxoisoindolin-5-yl)pyrrolidine-3-carbaldehyde

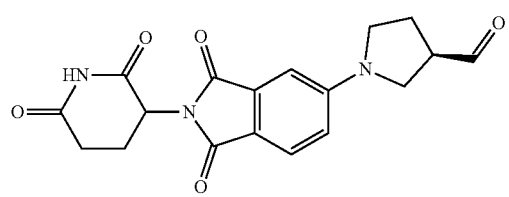 [SMILES: O=C[C@@H]1CCN(c2ccc3c(c2)C(=O)N(C2CCC(=O)NC2=O)C3=O)C1]

Step 2: Followed General Procedure B with (R)-pyrrolidin-3-ylmethanol to afford 2-(2,6-dioxopiperidin-3-yl)-5-((R)-3-(hydroxymethyl)pyrrolidin-1-yl)isoindoline-1,3-dione (480.6 mg, 74%) as a yellow solid. $^1$H NMR (300 MHz, DMSO-d$_6$) δ 11.08 (s, 1H), 7.64 (d, J=8.4 Hz, 1H), 6.89 (d, J=2.1 Hz, 1H), 6.80 (dd, J=8.4, 2.1 Hz, 1H), 5.06 (dd, J=12.9, 5.4 Hz, 1H), 4.78 (s, 1H), 3.65-3.36 (m, 5H), 3.22-3.17 (m, 1H), 2.95-2.83 (m, 1H), 2.67-2.44 (m, 3H), 2.11-1.89 (m, 2H), 1.87-1.78 (m, 1H). MS (ESI) calc'd for ($C_{18}H_{19}N_3O_5$) [M+H]$^+$, 358.1; found 358.1.

Step 3: (3R)-1-(2-(2,6-dioxopiperidin-3-yl)-1,3-dioxoisoindolin-5-yl)pyrrolidine-3-carbaldehyde LCMS $C_{18}H_{17}N_3O_5$ requires: 355, found: m/z=356 [M+H]$^+$.

Example 1G: Synthesis of (3S)-1-(2-(2,6-dioxopiperidin-3-yl)-1,3-dioxoisoindolin-5-yl)pyrrolidine-3-carbaldehyde

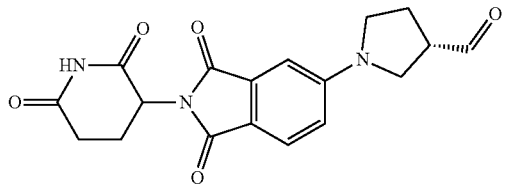 [SMILES: O=C[C@H]1CCN(c2ccc3c(c2)C(=O)N(C2CCC(=O)NC2=O)C3=O)C1]

Step 2: Followed General Procedure B with (S)-pyrrolidin-3-ylmethanol to afford 2-(2,6-dioxopiperidin-3-yl)-5-((S)-3-(hydroxymethyl)pyrrolidin-1-yl)isoindoline-1,3-dione (643.1 mg, 33%) as a yellow solid. $^1$H NMR (300 MHz, DMSO-$d_6$) δ 11.08 (s, 1H), 7.64 (d, J=8.4 Hz, 1H), 6.89 (d, J=2.1 Hz, 1H), 6.80 (dd, J=8.4, 2.1 Hz, 1H), 5.06 (dd, J=12.9, 5.4 Hz, 1H), 4.78 (t, J=5.4 Hz, 1H), 3.59-3.41 (m, 5H), 3.22-3.17 (m, 1H), 2.95-2.83 (m, 1H), 2.67-2.44 (m, 3H), 2.12-1.88 (m, 2H), 1.87-1.76 (m, 1H). MS (ESI) calc'd for ($C_{18}H_{19}N_3O_5$) [M+H]$^+$, 358.1; found 358.1.

Step 3: (3S)-1-(2-(2,6-dioxopiperidin-3-yl)-1,3-dioxoisoindolin-5-yl)pyrrolidine-3-carbaldehyde LCMS $C_{18}H_{17}N_3O_5$ requires: 355, found: m/z=356 [M+H]$^+$.

Example 1H: Synthesis of 2-(2,6-dioxopiperidin-3-yl)-5-((1R,5S,6r)-6-(hydroxymethyl)-3-aza-bicyclo[3.1.0]hexan-3-yl)isoindoline-1,3-dione

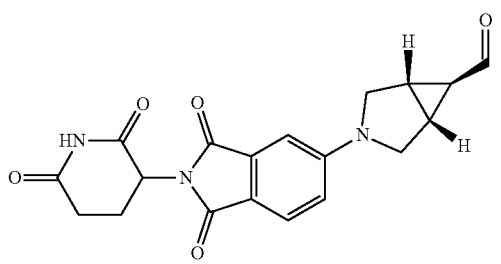 [SMILES: O=C[C@@H]1[C@H]2CN(c3ccc4c(c3)C(=O)N(C3CCC(=O)NC3=O)C4=O)C[C@@H]12]

Step 2: Followed General Procedure B with ((1R,5S,6r)-3-azabicyclo[3.1.0]hexan-6-yl)methanol to afford 2-(2,6-dioxopiperidin-3-yl)-5-((1R,5S,6r)-6-(hydroxymethyl)-3-azabicyclo[3.1.0]hexan-3-yl)isoindoline-1,3-dione (315.8 mg, 21%) as a yellow solid. $^1$H NMR (300 MHz, DMSO-$d_6$) δ 11.08 (s, 1H), 7.63 (d, J=8.4 Hz, 1H), 6.92 (d, J=2.1 Hz, 1H), 6.82 (dd, J=8.4, 2.1 Hz, 1H), 5.06 (dd, J=12.6, 5.4 Hz, 1H), 4.59 (t, J=5.4 Hz, 1H), 3.64-3.60 (m, 2H), 3.50-3.35 (m, 4H), 3.00-2.76 (m, 1H), 2.58-2.44 (m, 2H), 2.07-1.91 (m, 1H), 1.69 (s, 2H), 0.86-0.79 (m, 1H). MS (ESI) calc'd for ($C_{19}H_{19}N_3O_5$) [M+H]$^+$, 370.1; found 370.1.

Step 3: (1R,5S,6r)-3-(2-(2,6-dioxopiperidin-3-yl)-1,3-dioxoisoindolin-5-yl)-3-azabicyclo[3.1.0]hexane-6-carbaldehyde LCMS $C_{19}H_{17}N_3O_5$ requires: 367, found: m/z=368 [M+H]$^+$.

Example 2: Synthesis of 2-(4-(2-(2-(2,6-dioxopiperidin-3-yl)-1-oxoisoindolin-4-yl)ethyl)piperazin-1-yl)acetic acid

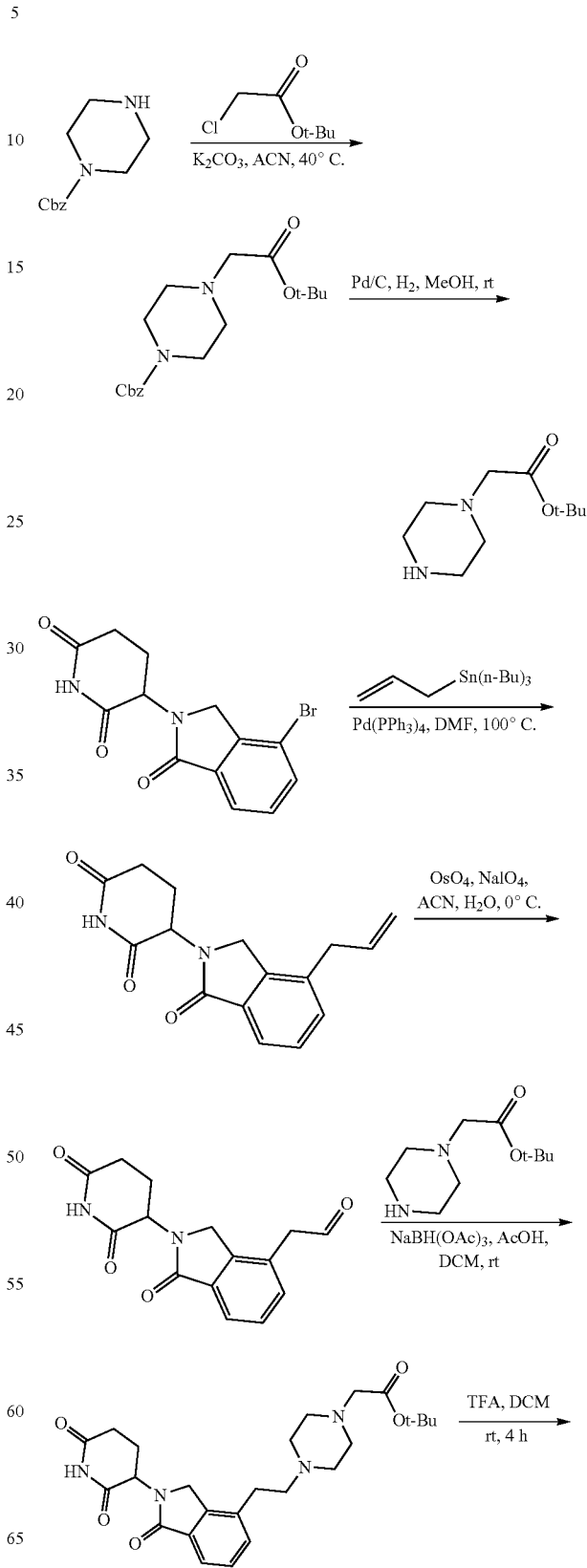

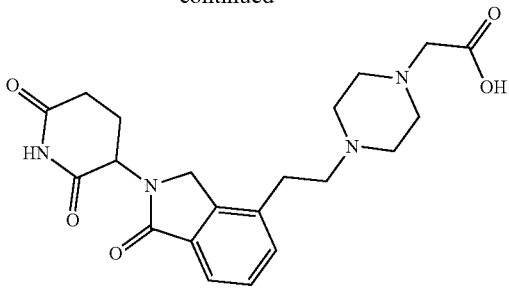

Step 1: Benzyl 4-(2-(tert-butoxy)-2-oxoethyl)piperazine-1-carboxylate.

To a solution of benzyl piperazine-1-carboxylate (10.0 g, 45.4 mmol) and $K_2CO_3$ (12.6 g, 90.8 mmol) in acetonitrile (150 mL) was added tert-butyl 2-chloroacetate (7.5 g, 49.9 mmol). The resulting solution was stirred at 40° C. for 16 h under nitrogen atmosphere. The solids were filtered out and the filtrate was concentrated under vacuum. The residue was purified by flash column chromatography with 0-50% ethyl acetate in petroleum ether to afford benzyl 4-(2-(tert-butoxy)-2-oxoethyl)piperazine-1-carboxylate (9.6 g, 63%) as a light yellow oil. MS (ESI) calculated for ($C_{18}H_{26}N_2O_4$) [M+H]+, 335.2; found, 335.3.

Step 2: Tert-Butyl 2-(piperazin-1-yl)acetate.

To a solution of benzyl 4-(2-(tert-butoxy)-2-oxoethyl)piperazine-1-carboxylate (9.6 g, 28.7 mmol) in methanol (100 mL) was added Pd/C (10%, 2.0 g) under nitrogen atmosphere. The mixture was stirred at room temperature for 16 h under hydrogen atmosphere (2 atm). The solids were filtered out and the filtrate was concentrated under vacuum to afford tert-butyl 2-(piperazin-1-yl)acetate (6.2 g, crude) as a light yellow oil, which was used in the next step without further purification. MS (ESI) calculated for ($C_{10}H_{20}N_2O_2$) [M+H]+, 201.2; found, 201.0.

Step 3: 3-(4-allyl-1-oxoisoindolin-2-yl)piperidine-2,6-dione.

A degassed mixture of 3-(4-bromo-1-oxo-2,3-dihydro-1H-isoindol-2-yl)piperidine-2,6-dione (10.0 g, 30.9 mmol), allyltributylstannane (15.4 g, 46.4 mmol) and Pd(PPh$_3$)$_4$ (3.6 g, 3.1 mmol) in DMF (80 mL) was stirred at 100° C. for 16 h under nitrogen atmosphere. When the reaction was completed by LCMS, the resulting mixture was diluted with water and extracted with ethyl acetate. The combined organic layer was washed with brine, dried over anhydrous $Na_2SO_4$, filtered and concentrated under vacuum. The residue was purified by flash column chromatography with 0~10% methanol in dichloromethane to afford 3-(4-allyl-1-oxoisoindolin-2-yl)piperidine-2,6-dione (7.0 g, 79%) as a white solid. MS (ESI) calculated for ($C_{16}H_{16}N_2O_3$) [M+H]+, 285.1; found, 285.2. $^1$H NMR (400 MHz, DMSO-d$_6$) δ 10.99 (s, 1H), 7.62-7.60 (m, 1H), 7.52-7.27 (m, 2H), 6.02-5.92 (m, 1H), 5.16-5.09 (m, 3H), 4.45 (d, J=17.2 Hz, 1H), 4.30 (d, J=17.2 Hz, 1H), 3.46-3.44 (m, 2H), 2.97-2.86 (m, 1H), 2.70-2.57 (m, 1H), 2.04-1.99 (m, 1H), 1.68-1.55 (m, 1H).

Step 4: 2-(2-(2,6-dioxopiperidin-3-yl)-1-oxoisoindolin-4-yl)acetaldehyde.

A mixture of 3-(4-allyl-1-oxoisoindolin-2-yl)piperidine-2,6-dione (7.0 g, 24.6 mmol), $OsO_4$ (625 mg, 2.5 mmol) and $NaIO_4$ (10.5 g, 49.2 mmol) in MeCN (60 mL) and $H_2O$ (20 mL) was stirred at 0° C. for 6 h. When the reaction was completed, the resulting mixture was diluted with water and extracted with ethyl acetate. The combined organic layer was washed with brine, dried over anhydrous $Na_2SO_4$, filtered and concentrated under vacuum to afford 2-(2-(2,6-dioxopiperidin-3-yl)-1-oxoisoindolin-4-yl)acetaldehyde (4.0 g, crude) as a brown solid, which was used in the next step without further purification. MS (ESI) calculated for ($C_{15}H_{14}N_2O_4$) [M+H]+, 287.1; found, 287.2.

Step 5: Tert-Butyl 2-(4-(2-(2-(2,6-dioxopiperidin-3-yl)-1-oxoisoindolin-4-yl)ethyl)piperazin-1-yl)acetate.

A mixture of 2-[2-(2,6-dioxopiperidin-3-yl)-1-oxo-2,3-dihydro-1H-isoindol-4-yl]acetaldehyde (4.0 g, 13.9 mmol), tert-butyl 2-(piperazin-1-yl)acetate (3.4 g, 16.8 mmol), AcOH (1 mL) and NaBH(OAc)$_3$ (5.9 g, 27.9 mmol) in dichloromethane (50 mL) was stirred at room temperature for 16 h. The resulting mixture was diluted with water and extracted with ethyl acetate. The combined organic layer was washed with brine, dried over anhydrous $Na_2SO_4$, filtered and concentrated under vacuum. The crude residue was purified by reverse phase flash column chromatography with 10-50% acetonitrile in water to afford tert-butyl 2-(4-(2-(2-(2,6-dioxopiperidin-3-yl)-1-oxoisoindolin-4-yl)ethyl)piperazin-1-yl)acetate (2.5 g, 22% over two steps) as a light brown syrup. MS (ESI) calculated for ($C_{25}H_{34}N_4O_5$) [M+H]+, 471.2; found, 471.0.

Step 6: 2-(4-(2-(2-(2,6-dioxopiperidin-3-yl)-1-oxoisoindolin-4-yl)ethyl)piperazin-1-yl)acetic acid TFA salt.

To a solution of tert-butyl 2-(4-(2-(2-(2,6-dioxopiperidin-3-yl)-1-oxoisoindolin-4-yl)ethyl)piperazin-1-yl)acetate (2.5 g, 5.3 mmol) in dichloromethane (20 mL) was added trifluoroacetic acid (20 mL). The resulting mixture was stirred at room temperature for 16 h before concentrated under vacuum. The residue was purified by reverse phase flash column chromatography with 5~30% acetonitrile in water to afford 2-(4-(2-(2-(2,6-dioxopiperidin-3-yl)-1-oxoisoindolin-4-yl)ethyl)piperazin-1-yl)acetic acid (1.7214 g, 78%) as a light brown solid. MS (ESI) calculated for ($C_{21}H_{26}N_4O_5$) [M+H]+, 415.2; found, 415.4. $^1$H NMR (300 MHz, DMSO-d$_6$) δ 11.08 (s, 1H), 7.66-7.62 (m, 1H), 7.54-7.47 (m, 2H), 5.14-5.08 (m, 1H), 4.54-4.48 (m, 1H), 4.40-4.31 (m, 1H), 3.76 (s, 2H), 3.60-3.10 (m, 10H), 3.10-2.78 (m, 3H), 2.68-2.54 (m, 1H), 2.40-2.31 (m, 1H), 2.10-1.94 (m, 1H).

Example 3: Synthesis of 5-[(3R)-3-(3-methyl-2-oxoimidazolidin-1-yl)piperidin-1-yl]-3-{[4-(piperazin-1-yl)phenyl]amino}pyrazine-2-carboxamide Step 1: 2-(2,6-dioxopiperidin-3-yl)-5-[(2S)-2-(hydroxymethyl)pyrrolidin-1-yl]isoindole-1,3-dione.

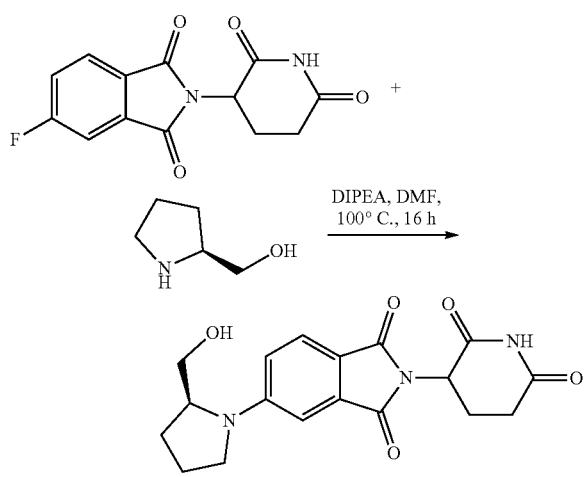

A mixture of 2-(2,6-dioxopiperidin-3-yl)-5-fluoroisoindole-1,3-dione (373 mg, 1.35 mmol), DMF (8 mL), ethylbis(propan-2-yl)amine (0.94 mL, 5.40 mmol) and prolinol (137 mg, 1.35 mmol) was allowed to stir at 90° C. for 16 h. CH₂Cl₂ and H₂O were added. The organic layer was dried with MgSO₄, filtered, concentrated and purified by MPLC (0-10% MeOH in CH₂Cl₂) to afford 2-(2,6-dioxopiperidin-3-yl)-5-[(2S)-2-(hydroxymethyl)pyrrolidin-1-yl]isoindole-1,3-dione (386.00 mg, 80.0%).

Step 2: (2S)-1-[2-(2,6-dioxopiperidin-3-yl)-1-oxo-3H-isoindol-5-yl]pyrrolidine-2-carbaldehyde isoindol-2-yl}piperidine-2,6-dione (222 mg, 0.65 mmol) and CH₂Cl₂ (10 mL). The mixture was allowed to stir at rt for 1 h. The mixture was purified by MPLC (10-100% EtOAc in hexanes) to afford (2S)-1-[2-(2,6-dioxopiperidin-3-yl)-1-oxo-3H-isoindol-5-yl]pyrrolidine-2-carbaldehyde (67 mg, 30%).

Example 4: Synthesis of 5-((R)-3-(3-methyl-2-oxo-imidazolidin-1-yl)piperidin-1-yl)-3-((4-(octahydro-2,7-naphthyridin-2(1H)-yl)phenyl)amino)pyrazine-2-carboxamide

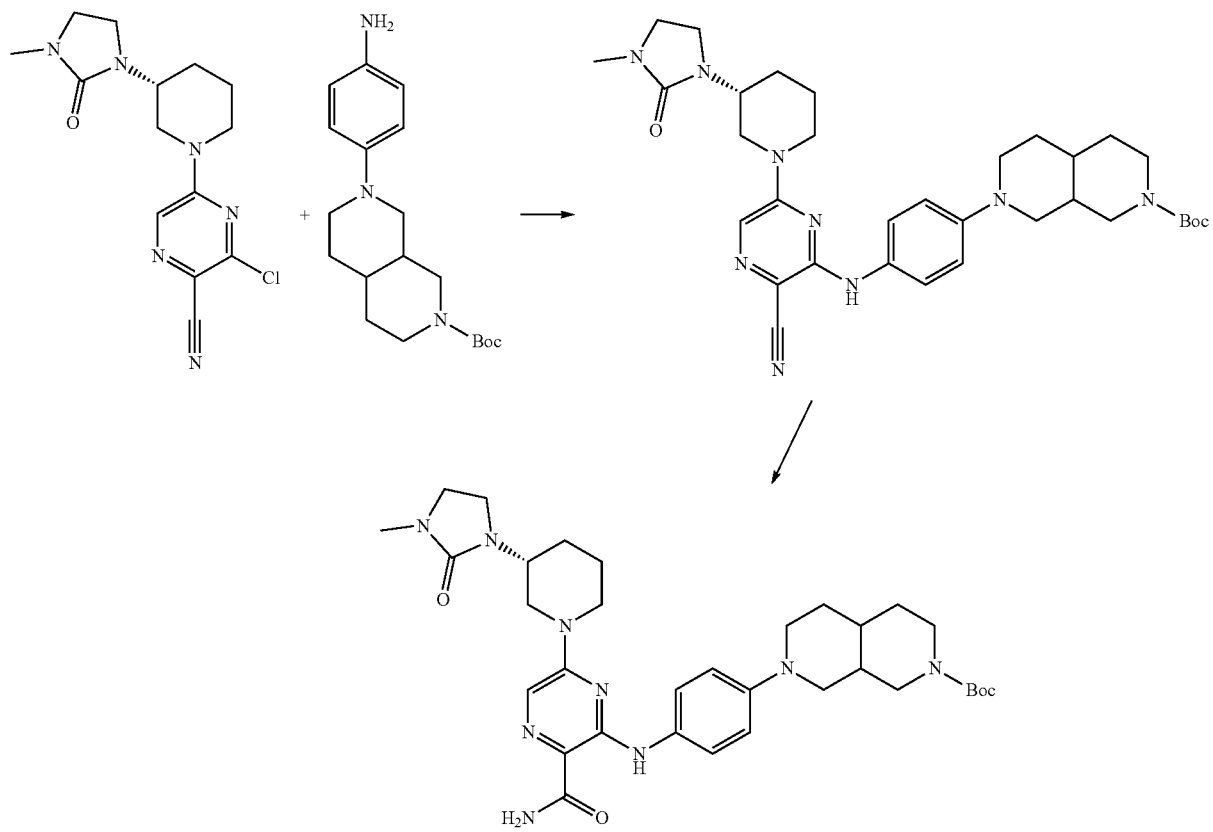

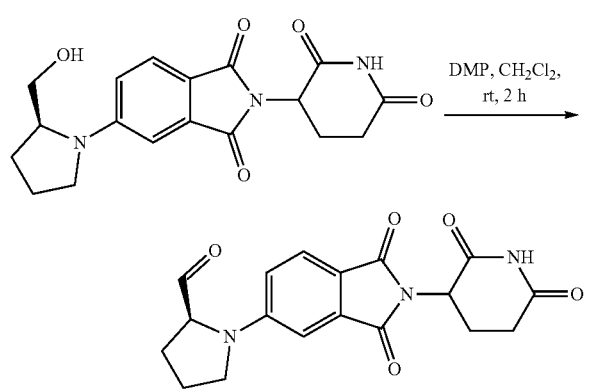

1,1-bis(acetyloxy)-3-oxo-1lambda5,2-benziodaoxol-1-yl acetate (548 mg, 1.29 mmol) was added to a mixture of 3-{5-[(2S)-2-(hydroxymethyl)pyrrolidin-1-yl]-1-oxo-3H-

Step 1: Under argon, Pd(OAc)₂ (105 mg, 0.47 mmol) was added to a degassed dioxane (10.00 mL) solution containing cesium carbonate (1523.56 mg, 4.68 mmol), tert-butyl 7-(4-aminophenyl)-octahydro-2,7-naphthyridine-2-carboxylate (517 mg, 1.56 mmol), BINAP (291 mg, 0.47 mmol), and 3-chloro-5-[(3R)-3-(3-methyl-2-oxoimidazolidin-1-yl)piperidin-1-yl]pyrazine-2-carbonitrile (500 mg, 1.56 mmol). The mixture was then stirred at 100 deg. C. for 16 h. The mixture was then partition with water and ethyl acetate, dried over sodium sulfate, and concentrated. The resulting residue was then purified by reverse phase preparative HPLC (Waters 5 mM CSH C18 column, 50×50 mm), eluting with solvent with acetonitrile in water with 0.1% TFA, using a 10-95% gradient over 9 min. The desired fractions were combined and concentrated to give product. This material was dissolved in a MeOH/DMSO solution (2 mL) 10:1 with one NaOH pellet. After 2 min. a 30% aqueous hydrogen peroxide solution (0.5 mL) was added and the reaction continued stirring at room temp for 1 h. The reaction was quenched with the addition of ACN. After concentration the crude reaction mixture was then purified by reverse phase preparative HPLC (Waters 5 mM CSH C18 column, 50×50 mm), eluting with solvent with acetonitrile in water with 0.1% TFA, using a 10-95% gradient over 9 min. The desired fractions were combined and concentrated to give product. LCMS $C_{25}H_{34}N_6O_3$ requires 633, found: m/z=634 $[M+H]^+$.

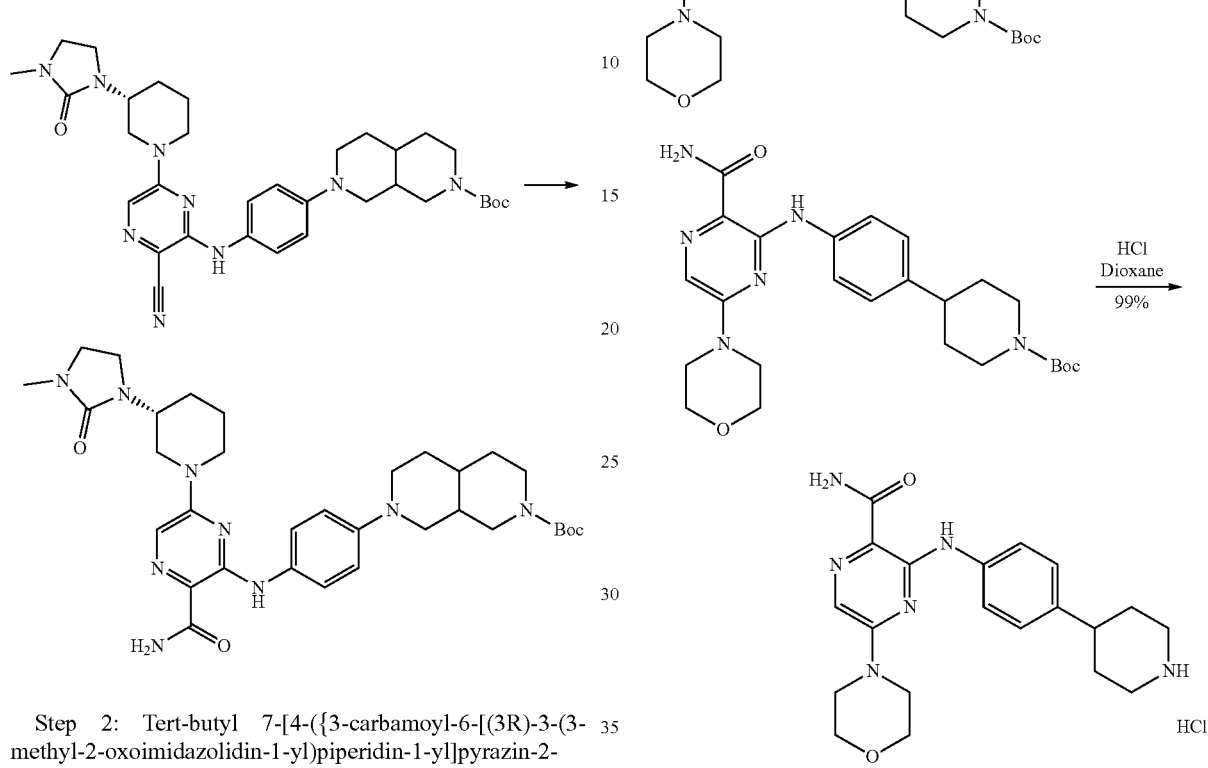

Step 2: Tert-butyl 7-[4-({3-carbamoyl-6-[(3R)-3-(3-methyl-2-oxoimidazolidin-1-yl)piperidin-1-yl]pyrazin-2-yl}amino)phenyl]-octahydro-2,7-naphthyridine-2-carboxylate (240 mg, 0.38 mmol) was dissolved in 1/1 DCM/TFA solution 2 mL and stirred at room temp for 1 h. The reaction was then concentrated. This material was used in the next step without further purification.

Example 5: Synthesis of 5-morpholino-3-[4-(4-piperidyl)anilino]pyrazine-2-carboxamide

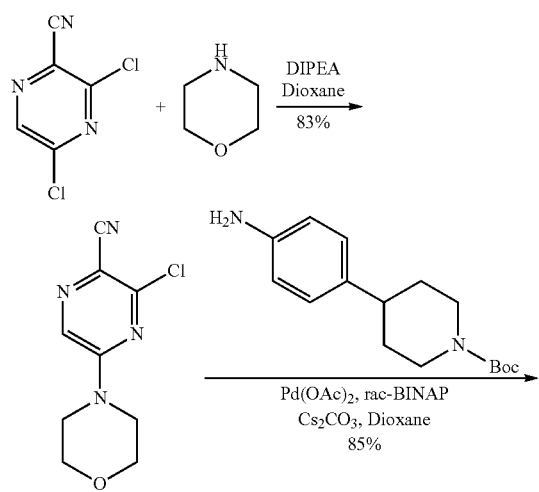

Step 1: 3-chloro-5-morpholino-pyrazine-2-carbonitrile.

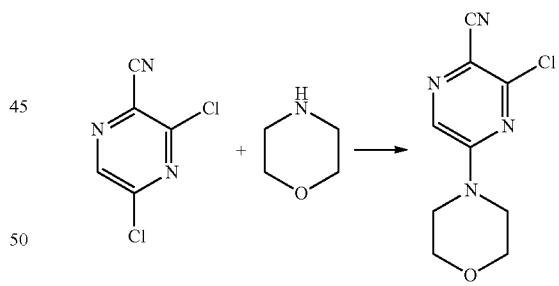

To a solution of morpholine (2.65 mL, 30.4 mmol) and 3,5-dichloropyrazine-2-carbonitrile 1 (6.2 g, 35.5 mmol) in anhydrous DMF (40.0 mL) at rt, was added DIPEA (6.4 mL, 36.5 mmol). The reaction solution was stirred at rt for 4 h. The mixture was diluted with water (100 mL) and EtOAc (100 mL). The layers were separated, and the aqueous layer was extracted with EtOAc (3×20 mL). The combined organic layers were washed with water (2×20 mL) and brine (3×20 mL), then dried ($Na_2SO_4$), filtered and concentrated under reduced pressure to afford title compound (5.7 g, 83%) as a solid. MS (ESI) $[M+H]^+$ 225.1.

Step 2: Tert-Butyl 4-[4-[(3-cyano-6-morpholino-pyrazin-2-yl)amino]phenyl]piperidine-1-carboxylate.

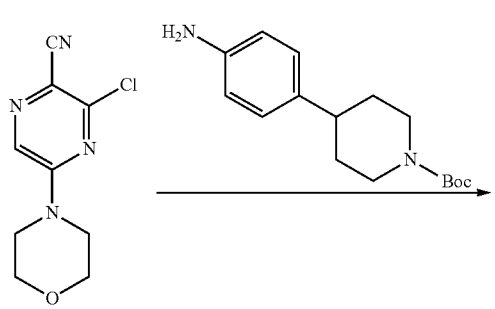

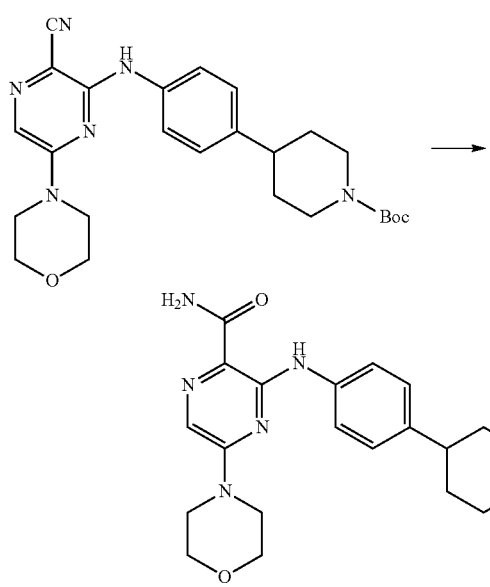

The mixture of 3-chloro-5-morpholino-pyrazine-2-carbonitrile (4.06 g, 18.1 mmol), tert-butyl 4-(4-aminophenyl)piperidine-1-carboxylate (5.0 g, 18.1 mmol), rac-BINAP (1.13 g, 1.81 mmol) and $Cs_2CO_3$ (17.7 g, 54.3 mmol) in anhydrous dioxane (60.0 mL) was degassed with $N_2$ for 10 min. $Pd(OAc)_2$ (406 mg, 1.81 mmol) was then added and the resulting mixture was heated at 80° C. for 16 h. The mixture was cooled to rt, the suspension was filtered on Celite and was washed with DCM (100 mL). The filtrate was concentrated under reduced pressure. The material was suspended in MeOH (50 mL) and sonicated for 2 min. The resulting solid filtered and dried to afford the title compound (7.1 g, 85%) as a solid. MS (ESI) [M-Boc+H]$^+$365.3.

Step 3: Tert-Butyl 4-[4-[(3-carbamoyl-6-morpholino-pyrazin-2-yl)amino]phenyl]piperidine-1-carboxylate.

To a solution of tert-butyl 4-[4-[(3-cyano-6-morpholino-pyrazin-2-yl)amino]phenyl]piperidine-1-carboxylate (7.1 g, 15.3 mmol) in MeOH (100.0 mL) and DMSO (10.0 mL) at rt, was added NaOH (4 M in water, 7.64 mL 30.6 mmol) followed by $H_2O_2$ (30% in water, 6.93 mL, 61.1 mmol). The reaction mixture was stirred at for 3.5 h. The mixture was diluted with acetonitrile (10 mL) and EtOAc (100 mL). The layers were separated, and the aqueous layer was extracted with EtOAc (3×50 mL). The combined organic layers were washed brine (2×30 mL), then dried ($Na_2SO_4$), filtered and concentrated under reduced pressure to afford the title compound as a solid (6.51 g, 88%). MS (ESI) [M-H]$^-$ 481.4.

Step 4: 5-morpholino-3-[4-(4-piperidyl)anilino]pyrazine-2-carboxamide hydrochloride.

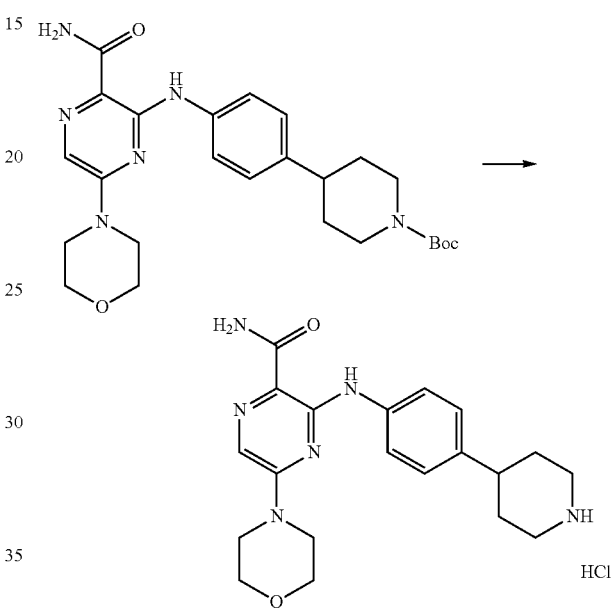

To a solution of tert-butyl 4-[4-[(3-carbamoyl-6-morpholino-pyrazin-2-yl)amino]phenyl]piperidine-1-carboxylate (6.51 g, 13.5 mmol) in anhydrous DCM (20.0 mL) at rt, was added HCl (35.0 mL, 140 mmol, 4 M in dioxane) and the reaction mixture was stirred at rt for 2 h. The resulting solid was filtered, washed with acetonitrile (100 mL) and DCM (100 mL), then dried under reduced pressure to afford title compound (5.6 g, 99%) as a yellow solid. $^1$H NMR (400 MHz, DMSO) δ 11.35 (s, 1H), 9.13-8.93 (m, 2H), 7.91-7.71 (m, 1H), 7.67 (s, 1H), 7.55 (d, J=8.6 Hz, 2H), 7.49-7.29 (m, 1H), 7.17 (d, J=8.6 Hz, 2H), 3.76-3.69 (m, 4H), 3.67-3.61 (m, 4H), 3.33 (d, J=12.7 Hz, 2H), 3.02-2.90 (m, 2H), 2.84-2.73 (m, 1H), 1.94-1.81 (m, 4H). MS (ESI) [M+H]$^+$ 383.2.

Example 6: 5-(4-methylpiperazin-1-yl)-3-[4-(4-piperidyl)anilino]pyrazine-2-carboxamide

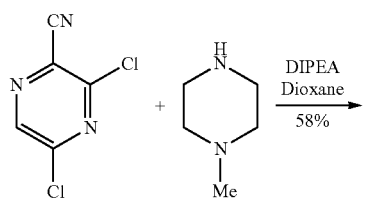

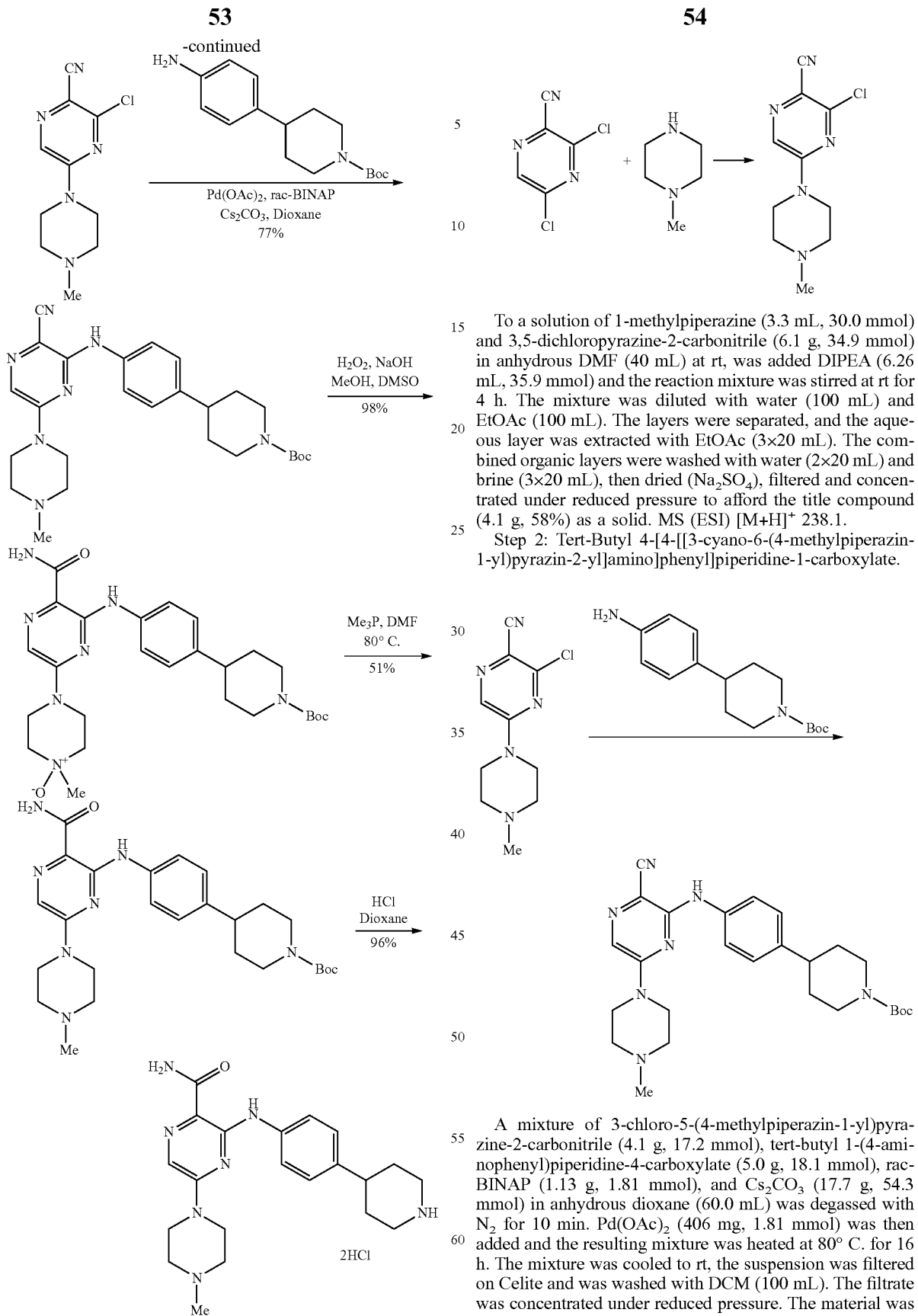

Step 1: 3-chloro-5-(4-methylpiperazin-1-yl)pyrazine-2-carbonitrile.

To a solution of 1-methylpiperazine (3.3 mL, 30.0 mmol) and 3,5-dichloropyrazine-2-carbonitrile (6.1 g, 34.9 mmol) in anhydrous DMF (40 mL) at rt, was added DIPEA (6.26 mL, 35.9 mmol) and the reaction mixture was stirred at rt for 4 h. The mixture was diluted with water (100 mL) and EtOAc (100 mL). The layers were separated, and the aqueous layer was extracted with EtOAc (3×20 mL). The combined organic layers were washed with water (2×20 mL) and brine (3×20 mL), then dried ($Na_2SO_4$), filtered and concentrated under reduced pressure to afford the title compound (4.1 g, 58%) as a solid. MS (ESI) $[M+H]^+$ 238.1.

Step 2: Tert-Butyl 4-[4-[[3-cyano-6-(4-methylpiperazin-1-yl)pyrazin-2-yl]amino]phenyl]piperidine-1-carboxylate.

A mixture of 3-chloro-5-(4-methylpiperazin-1-yl)pyrazine-2-carbonitrile (4.1 g, 17.2 mmol), tert-butyl 1-(4-aminophenyl)piperidine-4-carboxylate (5.0 g, 18.1 mmol), rac-BINAP (1.13 g, 1.81 mmol), and $Cs_2CO_3$ (17.7 g, 54.3 mmol) in anhydrous dioxane (60.0 mL) was degassed with $N_2$ for 10 min. $Pd(OAc)_2$ (406 mg, 1.81 mmol) was then added and the resulting mixture was heated at 80° C. for 16 h. The mixture was cooled to rt, the suspension was filtered on Celite and was washed with DCM (100 mL). The filtrate was concentrated under reduced pressure. The material was suspended in MeOH (50 mL) and sonicated for 2 min. The resulting solid filtered and dried under reduced pressure to afford the title compound (6.68 g, 77%) as a solid. MS (ESI) $[M-Boc+2H]^+$ 378.3.

Step 3: Tert-Butyl 4-[4-[[3-carbamoyl-6-(4-methyl-4-oxido-piperazin-4-ium-1-yl)pyrazin-2-yl]amino]phenyl]piperidine-1-carboxylate.

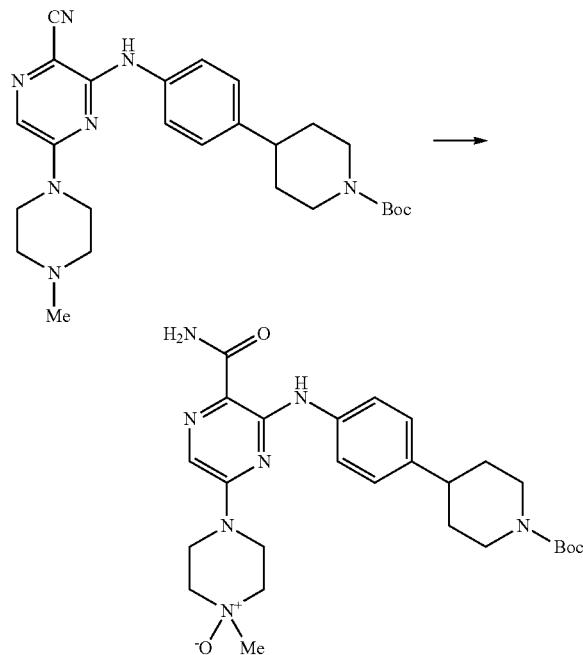

To a suspension of tert-butyl 4-[4-[[3-cyano-6-(4-methylpiperazin-1-yl)pyrazin-2-yl]amino]phenyl]piperidine-1-carboxylate (6.80 g, 14.2 mmol) in MeOH (100.0 mL) and DMSO (10.0 mL) at rt, was added aqueous NaOH (4 M in water, 7.1 mL 28.5 mmol), followed by $H_2O_2$ (30% in water, 6.5 mL, 57.3 mmol) at rt. The reaction mixture was stirred at for 3.5 h. The mixture was diluted with cold water (50 mL). The resulting solid was filtered and washed with water (50 mL) and cold MeOH (40 mL) to afford the title compound (7.10 g, 98%) as a solid. $^1$H NMR (400 MHz, DMSO) δ 11.30 (s, 1H), 7.82-7.73 (m, 1H), 7.67 (s, 1H), 7.51 (d, J=8.6 Hz, 2H), 7.41-7.31 (m, 1H), 7.18 (d, J=8.5 Hz, 2H), 4.13-3.98 (m, 2H), 3.73-3.58 (m, 4H), 2.90-2.71 (m, 2H), 2.69-2.57 (m, 1H), 2.46-2.35 (m, 4H), 2.22 (s, 3H), 1.79-1.67 (m, 2H), 1.52-1.43 (m, 2H), 1.42 (s, 9H). MS (ESI) [M−H]$^+$510.5.

Step 4: Tert-Butyl 4-[4-[[3-carbamoyl-6-(4-methylpiperazin-1-yl)pyrazin-2-yl]amino]phenyl]piperidine-1-carboxylate.

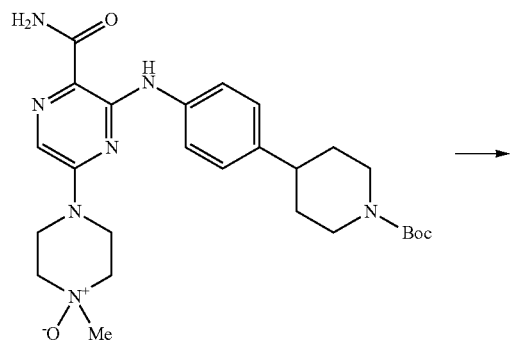

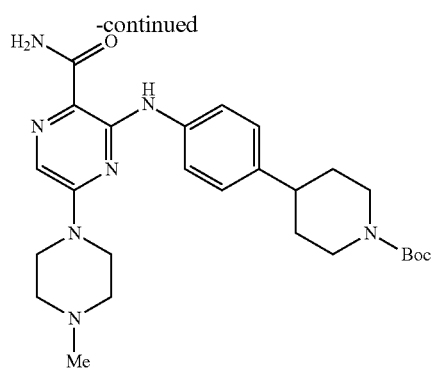

To solution of tert-butyl 4-[4-[[3-carbamoyl-6-(4-methyl-4-oxido-piperazin-4-ium-1-yl)pyrazin-2-yl]amino]phenyl]piperidine-1-carboxylate (4.50 g, 8.80 mmol) in anhydrous DMF (50.0 mL) at rt, was added trimethylphosphane (44.0 mL, 44.0 mmol, 1.0 M in THF) and the resulting mixture was heated at 80° C. for 4 h. The mixture was diluted with EtOAc (100 mL) and water (200 mL). The layers were separated, and the aqueous layer was extracted with EtOAc (3×50 mL). The combined organic layers were washed with brine (3×50 mL), then dried ($Na_2SO_4$), filtered and concentrated under reduced pressure to afford title compound (2.20 g, 51%) as a solid. MS (ESI) [M−H]$^-$ 494.5.

Step 5: 5-(4-methylpiperazin-1-yl)-3-[4-(4-piperidyl)anilino]pyrazine-2-carboxamide dihydrochloride.

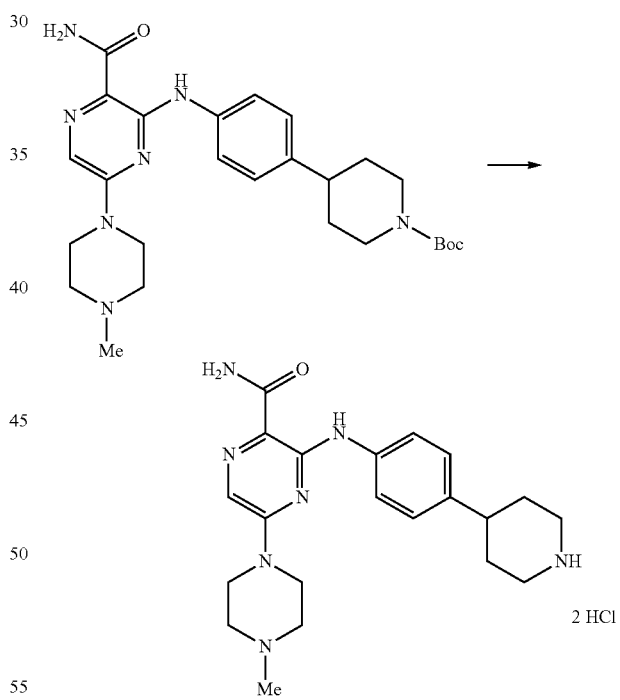

To a solution of tert-butyl 4-[4-[[3-carbamoyl-6-(4-methylpiperazin-1-yl)pyrazin-2-yl]amino]phenyl]piperidine-1-carboxylate (2.60 g, 5.25 mmol) in anhydrous DCM (40.0 mL) at rt, was added HCl (15.0 mL, 60.0 mmol, 4.0 M in dioxane) and the resulting suspension was stirred at rt for 1 h. The resulting solid was filtered, washed with DCM (100 mL) and dried under reduced pressure to afford the title compound (2.35 g, 96%) as a yellow-orange solid. $^1$H NMR (500 MHz, DMSO) δ 11.55-11.40 (m, 1H), 11.38 (s, 1H), 9.21-8.99 (m, 2H), 7.96-7.85 (m, 1H), 7.78 (s, 1H), 7.55 (d, J=8.4 Hz, 2H), 7.51-7.42 (m, 1H), 7.20 (d, J=8.4 Hz, 2H), 4.49 (d, J=14.3 Hz, 2H), 3.55-3.44 (m, 4H), 3.39-3.29 (m, 2H), 3.20-3.06 (m, 2H), 3.04-2.90 (m, 2H), 2.85-2.72 (m, 4H), 1.97-1.79 (m, 4H). MS (ESI) [M+H]+ 396.3.

Example 7: Synthesis of 3-((4-(piperidin-4-yl)phenyl)amino)-5-(pyrrolidin-1-yl)pyrazine 2-carboxamide

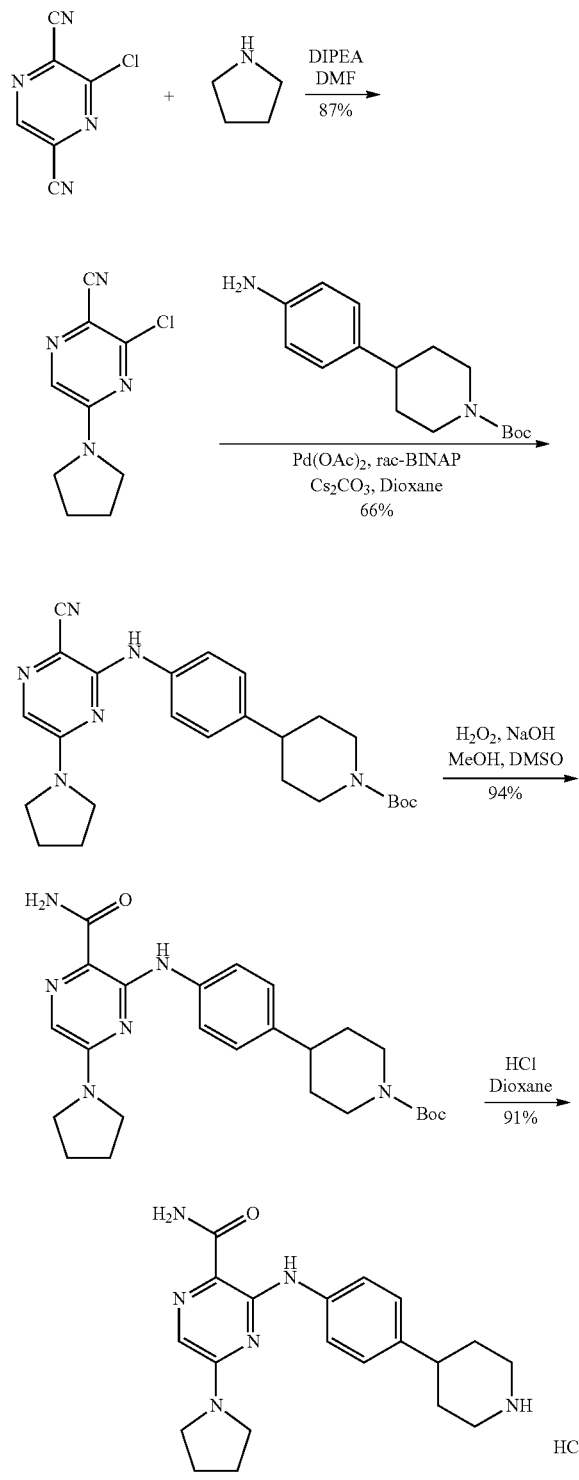

Step 1: 3-chloro-5-pyrrolidin-1-yl-pyrazine-2-carbonitrile.

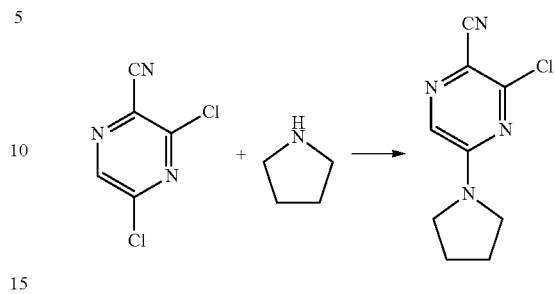

To a solution of pyrrolidine (1.52 mL, 18.2 mmol) and 3,5-dichloropyrazine-2-carbonitrile (3.17 g, 18.2 mmol) in anhydrous DMF (20.0 mL) at rt, was added DIPEA (3.81 mL, 21.9 mmol). The resulting solution was stirred at rt for 1 h. The mixture was diluted with water (100 mL) and the resulting solid was collected by filtration then dried under reduced pressure to afford title compound (3.3 g, 87%) as a solid. MS (ESI) [M+H]+ 209.1.

Step 2: Tert-Butyl 4-[4-[(3-cyano-6-pyrrolidin-1-yl-pyrazin-2-yl)amino]phenyl]piperidine-1-carboxylate.

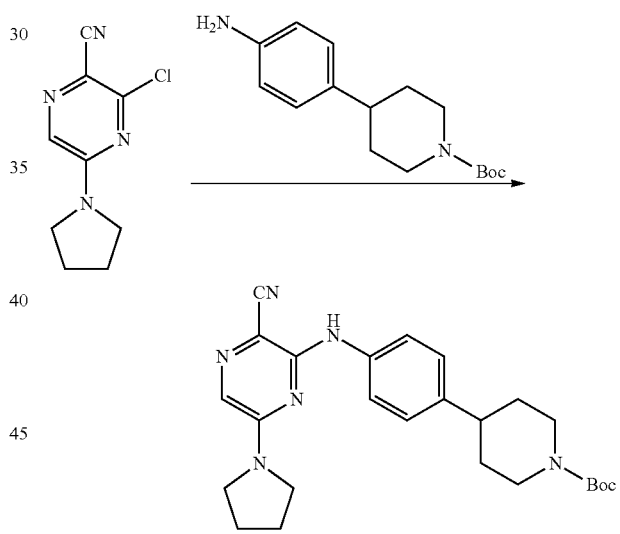

A mixture of 3-chloro-5-pyrrolidin-1-yl-pyrazine-2-carbonitrile (3.40 g, 16.3 mmol), tert-butyl 4-(4-aminophenyl)piperidine-1-carboxylate (4.50 g, 16.3 mmol), rac-BINAP (1.13 g, 1.81 mmol) and Cs$_2$CO$_3$ (15.9 g, 48.9 mmol) in anhydrous dioxane (60.0 mL) was degassed with N$_2$ for 10 min. Pd(OAc)$_2$ (406 mg, 1.81 mmol) was then added and the resulting mixture was heated at 80° C. for 16 h. The mixture was cooled to rt, the suspension was filtered on Celite and was washed with DCM (100 mL). The filtrate was concentrated reduced pressure. The material was suspended in MeOH (50 mL) and sonicated for 2 min. The resulting solid was filtered and dried under reduced pressure to afford the title compound (4.80 g, 66%) as a solid. $^1$H NMR (400 MHz, DMSO) δ 8.83 (s, 1H), 7.59 (d, J=8.7 Hz, 2H), 7.50 (s, 1H), 7.15 (d, J=8.6 Hz, 2H), 4.13-3.96 (m, 2H), 3.52-3.42 (m, 4H), 2.88-2.70 (m, 2H), 2.67-2.58 (m, 1H), 2.01-1.84 (m, 4H), 1.79-1.68 (m, 2H), 1.52-1.42 (m, 2H), 1.41 (s, 9H). MS (ESI) [M-Boc+2H]+ 349.3.

Step 3: Tert-Butyl 4-[4-[(3-carbamoyl-6-pyrrolidin-1-yl-pyrazin-2-yl)amino]phenyl]piperidine-1-carboxylate.

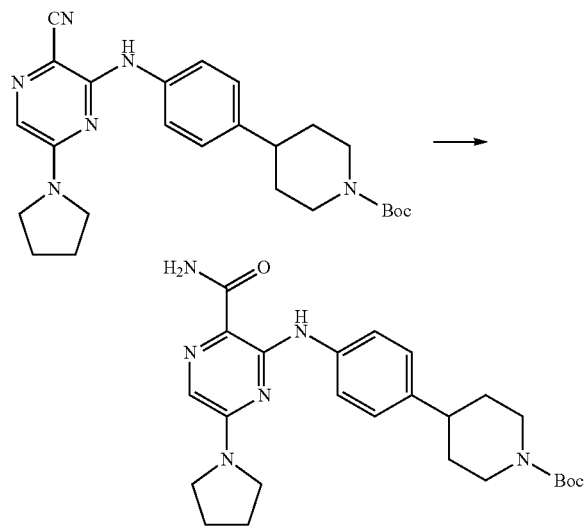

To a solution of tert-butyl 4-[4-[(3-cyano-6-pyrrolidin-1-yl-pyrazin-2-yl)amino]phenyl]piperidine-1-carboxylate (4.80 g, 10.7 mmol) in MeOH (100.0 mL) and DMSO (10.0 mL) at rt, was added NaOH (4 M in water, 5.35 mL 21.4 mmol) followed by $H_2O_2$ (30% in water, 4.85 mL, 42.8 mmol) at rt. The reaction mixture was stirred at for 18 h, and then water (100 mL) was added. The resulting solid was filtered and dried under reduced pressure to afford the title compound (4.70 g, 94%) as a solid. $^1$H NMR (500 MHz, DMSO) δ 11.40 (s, 1H), 7.75-7.71 (m, 1H), 7.64 (d, J=8.6 Hz, 2H), 7.35 (s, 1H), 7.31-7.25 (m, 1H), 7.18 (d, J=8.6 Hz, 2H), 4.15-4.01 (m, 2H), 3.59-3.49 (m, 4H), 2.95-2.70 (m, 2H), 2.67-2.59 (m, 1H), 2.04-1.93 (m, 4H), 1.79-1.72 (m, 2H), 1.51-1.44 (m, 2H), 1.42 (s, 9H).

Step 4: 3-[4-(4-piperidyl)anilino]-5-pyrrolidin-1-yl-pyrazine-2-carboxamide hydrochloride.

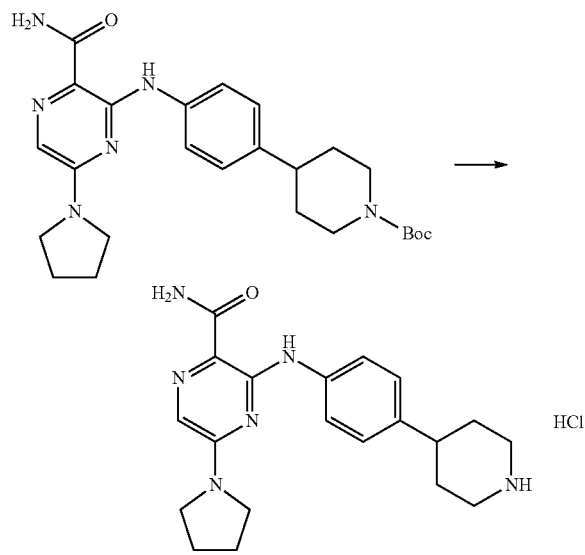

To a solution of tert-butyl 4-[4-[(3-carbamoyl-6-pyrrolidin-1-yl-pyrazin-2-yl)amino]phenyl]piperidine-1-carboxylate (4.80 g, 10.3 mmol) in DCM (75 mL) and MeOH (25 mL) at rt, was added HCl (20.0 mL, 80.0 mmol, 4.0 M in dioxane) and the resulting mixture was stirred at rt for 2 h. The suspension was filtered, washed with DCM and then dried under reduced pressure to afford title compound (3.78 g, 91%) as yellow-orange solid. $^1$H NMR (400 MHz, DMSO) δ 11.42 (s, 1H), 8.97-8.76 (m, 2H), 7.82-7.59 (m, 1H), 7.68 (d, J=8.5 Hz, 2H), 7.35 (s, 1H), 7.33-7.19 (m, 1H), 7.16 (d, J=8.5 Hz, 2H), 3.56-3.47 (m, 4H), 3.38-3.30 (m, 2H), 3.03-2.90 (m, 2H), 2.83-2.73 (m, 1H), 2.03-1.96 (m, 4H), 1.92-1.77 (m, 4H). MS (ESI) [M+H]$^+$ 367.2.

Example 8

General Procedure 1: Amide Coupling

A mixture of amine (0.03 mmol), acid (0.03 mmol), HATU (0.04 mmol), DIPEA (0.15 mmol), and DMF is allowed to stir at room temperature for 30 minutes. The mixture is purified by HPLC ($H_2O$/MeCN with 0.1% TFA) to afford the amide product.

General Procedure 2: Reductive Amination

A mixture of amine TFA salt (0.07 mmol), aldehyde (0.1 mmol), triethylamine (0.28 mmol), and DCE is allowed to stir at room temperature for 10 minutes. NaBH(OAc)$_3$ (0.14 mmol) was added and the mixture was allowed to stir at room temperature for 2 h. The mixture is filtered through celite, washed with $CH_2Cl_2$, concentrated, and purified by HPLC ($H_2O$/MeCN with 0.1% TFA) to afford the amine product.

General Procedure 3: Aryl Fluoride Displacement

A mixture of amine (0.22 mmol), aryl fluoride (0.22 mmol), DIPEA (0.88 mmol), and DMF (1 mL) is allowed to stir at 90° C. for 16 h. The mixture is purified by HPLC ($H_2O$/MeCN with 0.1% TFA) to afford the desired product.

Physical Data for Example Compounds of Table 1.

The $^1$H NMR spectra and mass spectrometry (LCMS) data were obtained for the example compounds reported in Table 1. These experimental data are provided in Table 2.

TABLE 2

Physical Data for the Example Compounds of Table 1.

| Compound No. | $^1$H NMR | Mass Spec (LCMS) |
|---|---|---|
| 32 | $^1$H NMR (500 MHz, DMSO-d$_6$) δ 11.20 (s, 1H), 11.07 (s, 1H), 7.76 (s, 1H), 7.67 (t, J = 4.3 Hz, 2H), 7.52 (d, J = 8.3 Hz, 2H), 7.32 (d, J = 21.4 Hz, 2H), 7.21 (t, J = 8.3 Hz, 3H), 5.06 (dd, J = 12.9, 5.4 Hz, 1H), 4.44-4.25 (m, 2H), 3.89 (s, 3H), 3.62 (d, J = 11.2 Hz, 1H), 3.10-2.81 (m, 6H), 2.73 (s, 3H), 2.69-2.57 (m, 2H), 2.41-2.26 (m, 1H), 2.22-1.45 (m, 19H), 1.26 (d, J = 17.1 Hz, 4H). | LCMS: $C_{44}H_{53}N_{11}O_6$ requires: 831, found: m/z = 832 [M + H]$^+$. |
| 87 | $^1$H NMR (500 MHz, DMSO-d$_6$) δ 11.19 (s, 1H), 11.08 (s, 1H), 7.76 (d, J = 2.8 Hz, 1H), 7.69-7.64 (m, 2H), 7.54-7.48 (m, 2H), 7.34 (d, J = 2.9 Hz, 1H), 7.18 (d, J = 8.2 Hz, 2H), 7.04 (d, J = 9.6 Hz, 1H), 6.89 (d, J = 8.7 Hz, 1H), 5.06 (dd, J = 12.8, 5.4 Hz, 1H), 4.34 (dd, J = 41.1, 12.8 Hz, 2H), 4.16 (s, 1H), 3.69-3.49 (m, 2H), 3.19 (s, 1H), 3.11-2.83 (m, 4H), 2.73 (s, 3H), 2.68-2.55 (m, 2H), 2.46-2.29 (m, 2H), 2.25-1.93 (m, 7H), 1.90-1.49 (m, 7H), 1.25 (s, 2H). | LCMS: $C_{43}H_{51}N_{11}O_6$ requires: 817, found: m/z = 818 [M + H]$^+$. |
| 89 | $^1$H NMR (500 MHz, DMSO-d$_6$) δ 11.45 (s, 1H), 11.07 (s, 1H), 8.09 (d,J = 9.1 Hz, 1H), 8.01 (d, J = 3.0 Hz, 1H), 7.77 (d, J = 2.8 Hz, 1H), 7.71 (s, 1H), 7.65 (d, J = 8.4 Hz, 1H), 7.40-7.33 (m, 2H), 6.92 (d, J = 2.2 Hz, 1H), 6.83 (dd, J = 8.6, 2.2 Hz, 1H), 5.03 (d, J = 11.0 Hz, 1H), 4.40 (d, J = 12.5 Hz, 1H), 4.31 (d, J = 13.3 Hz, 1H), 3.67-3.56 (m, 2H), 3.54-3.50 (m, 1H), 3.47-3.22 (m, 6H), 3.21-2.93 (m, 7H), 2.87 (t, J = 14.0 Hz, 1H), 2.75-2.32 (m, 12H), 2.20-2.13 (m, 1H), 2.04-1.97 (m, 1H), 1.90-1.73 (m, 3H), 1.65-1.49 (m, 2H). | LCMS: $C_{41}H_{49}N_{13}O_6$ requires 819, found: m/z = 820 [M + H]$^+$ |

TABLE 2-continued

Physical Data for the Example Compounds of Table 1.

| Compound No. | ¹H NMR | Mass Spec (LCMS) |
|---|---|---|
| 125 | ¹H NMR (500 MHz, Acetonitrile-d₃) δ 11.34 (s, 1H), 11.16 (s, 1H), 8.89 (s, 1H), 8.57 (s, 1H), 8.51 (d, J = 2.7 Hz, 1H), 7.87 (s, 1H), 7.76 (s, 1H), 7.69 (dd, J = 21.8, 8.3 Hz, 3H), 7.34 (d, J = 8.3 Hz, 2H), 6.98 (d, J = 2.2 Hz, 1H), 6.83 (dd, J = 8.5, 2.1 Hz, 1H), 6.62 (t, J = 2.1 Hz, 1H), 6.28 (s, 1H), 4.96 (dd, J = 12.0, 5.4 Hz, 1H), 3.90-3.65 (m, 3H), 3.65-3.53 (m, 1H), 3.47 (q, J = 8.7 Hz, 1H), 3.31 (t, J = 9.0 Hz, 3H), 3.12-2.83 (m, 4H), 2.83-2.62 (m, 3H), 2.53 (s, 1H). | LCMS: $C_{37}H_{38}N_{10}O_5$ requires: 702.8, found: m/z = 703.7 [M + H]⁺ |
| 126 | ¹H NMR (500 MHz, DMSO-d₆) δ 11.36 (d, J = 6.8 Hz, 1H), 11.09 (s, 1H), 9.08 (d, J = 10.7 Hz, 1H), 7.78 (d, J = 7.6 Hz, 2H), 7.71 (d, J = 8.4 Hz, 1H), 7.66 (d, J = 8.2 Hz, 2H), 7.36 (d, J = 11.7 Hz, 1H), 7.24 (d, J = 8.2 Hz, 2H), 6.97 (d, J = 2.1 Hz, 1H), 6.87 (dd, J = 8.6, 2.2 Hz, 1H), 5.08 (dd, J = 12.7, 5.5 Hz, 1H), 4.32 (s, 4H), 3.98 (s, 2H), 3.83-3.65 (m, 5H), 3.13 (t, J = 10.9 Hz, 3H), 2.88 (ddt, J = 24.4, 16.0, 12.6 Hz, 4H), 2.63-2.55 (m, 3H), 2.31 (dd, J = 12.3, 6.9 Hz, 1H), 2.04 (q, J = 9.5, 5.9 Hz, 3H), 1.92 (h, J = 7.9, 5.9 Hz, 4H), 1.58 (q, J = 7.4, 6.0 Hz, 2H). | LCMS: $C_{41}H_{47}N_9O_6$ requires: 761.9, found: m/z = 762.8 [M + H]⁺ |
| 128 | ¹H NMR (500 MHz, DMSO-d₆) δ 11.26 (s, 1H), 11.08 (s, 1H), 7.84-7.75 (m, 1H), 7.75-7.59 (m, 2H), 7.51 (d, J = 8.2 Hz, 2H), 7.40-7.31 (m, 1H), 7.19 (d, J = 8.2 Hz, 2H), 6.98-6.75 (m, 2H), 5.06 (dd, J = 12.9, 5.4 Hz, 1H), 4.41 (d, J = 12.8 Hz, 1H), 4.31 (t, J = 8.0 Hz, 3H), 3.61 (dt, J = 15.9, 8.2 Hz, 7H), 3.16 (d, J = 10.7 Hz, 6H), 3.02 (dt, J = 20.5, 10.8 Hz, 4H), 2.92-2.85 (m, 1H), 2.64 (d, J = 28.8 Hz, 3H), 2.40 (d, J = 7.5 Hz, 3H), 2.15 (d, J = 6.9 Hz, 1H), 2.14-1.97 (m, 4H), 1.83 (ddd, J = 43.1, 32.8, 8.9 Hz, 7H), 1.63 (dd, J = 30.3, 13.7 Hz, 4H). | LCMS: $C_{38}H_{37}N_1F_3O_5$ requires: 770.8, found: m/z = 771.8, [M + H]⁺ |
| 130 | ¹H NMR (500 MHz, DMSO-d₆) δ 11.18 (s, 1H), 10.84 (s, 1H), 8.69 (d, J = 8.3 Hz, 1H), 8.31 (s, 1H), 7.84 (d, J = 8.9 Hz, 1H), 7.75 (s, 1H), 7.66 (d, J = 7.9 Hz, 2H), 7.40 (d, J = 9.0 Hz, 1H), 7.32 (s, 1H), 7.19-7.13 (m, 2H), 5.75 (s, 1H), 4.74 (s, 1H), 4.35 (s, 1H), 4.28 (d, J = 13.1 Hz, 1H), 3.94 (d, J = 12.5 Hz, 1H), 3.62 (s, 1H), 3.27 (d, J = 7.7 Hz, 2H), 3.07-2.96 (m, 1H), 2.97-2.91 (m, 3H), 2.86 (t, J = 12.5 Hz, 2H), 2.81-2.74 (m, 1H), 2.72 (s, 3H), 2.42 (s, 1H), 2.18 (d, J = 5.8 Hz, 3H), 2.02-1.93 (m, 4H), 1.85-1.78 (m, 5H), 1.77-1.71 (m, 3H), 1.63-1.59 (m, 3H), 1.25-1.16 (m, 3H). | LCMS: $C_{42}H_{54}N_{12}O_5$ requires: 806, found: m/z = 807 [M + H]⁺ |
| 146 | ¹H NMR (500 MHz, CD₃CN) δ 11.09 (s, 1H), 9.86 (s, 1H), 8.88 (s, 1H), 7.64 (d, J = 8.4 Hz, 1H), 7.58 (d, J = 8.2 Hz, 2H), 7.54 (s, 1H), 7.40 (s, 1H), 7.18 (d, J = 8.2 Hz, 2H), 6.94 (d, J = 2.3 Hz, 1H), 6.79 (dd, J = 8.6, 2.3 Hz, 1H), 5.81 (s, 1H), 4.93 (dd, J = 12.2, 5.4 Hz, 1H), 4.40-4.34 (m, 1H), 4.29 (d, J = 13.6 Hz, 1H), 3.94 (tt, J = 10.3, 4.5 Hz, 1H), 3.72 (ddd, J = 33.4, 15.6, 9.9 Hz, 3H), 3.55 (td, J = 9.5, 8.6, 3.3 Hz, 1H), 3.48-3.34 (m, 3H), 3.29-3.18 (m, 3H), 3.02 (dt, J = 31.3, 12.1 Hz, 4H), 2.93-2.63 (m, 4H), 2.32 (td, J = 8.1, 3.4 Hz, 3H), 2.16-1.96 (m, 6H), 1.86 (qd, J = 12.9, 6.4 Hz, 4H), 1.71-1.61 (m, 1H). | LCMS: $C_{43}H_{50}N_{10}O_6$ requires: 802, found: m/z = 803 [M + H]⁺ |
| 148 | ¹H NMR (500 MHz, DMSO-d₆) δ 11.50 (s, 1H), 11.07 (s, 1H), 9.02 (s, 1H), 8.68 (s, 1H), 8.54 (s, 1H), 8.14 (d, J = 3.1 Hz, 1H), 8.09-8.03 (m, 2H), 7.77 (d, J = 8.1 Hz, 1H), 7.70 (d, J = 8.2 Hz, 1H), 7.31 (d, J = 8.3 Hz, 2H), 6.95 (s, 1H), 6.89-6.83 (m, 1H), 5.06 (dd, J = 12.7, 5.4 Hz, 1H), 3.76 (dd, J = 18.8, 9.5 Hz, 1H), 3.68 (d, J = 17.4 Hz, 2H), 3.58 (t, J = 9.6 Hz, 2H), 3.25 (dd, J = 10.3, 8.2 Hz, 1H), 3.15 (d, J = 13.2 Hz, 2H), 2.94-2.83 (m, 3H), 2.59 (d, J = 16.0 Hz, 1H), 2.39 (s, 1H), 2.29 (s, 2H), 2.09 (d, J = 13.1 Hz, 2H), 2.01 (dd, J = 12.5, 6.3 Hz, 1H), 1.89 (dt, J = 32.7, 11.1 Hz, 3H). | LCMS: $C_{37}H_{37}N_9O_5S$ requires: 719, found: m/z = 720 [M + H]⁺ |
| 149 | ¹H NMR (500 MHz, DMSO-d₆) δ 11.28 (s, 1H), 11.06 (s, 1H), 7.73 (d, J = 2.8 Hz, 1H), 7.66 (s, 1H), 7.64 (d, J = 8.4 Hz, 1H), 7.55-7.48 (m, 2H), 7.31 (d, J = 2.9 Hz, 1H), 7.20 (s, 1H), 7.18 (s, 1H), 6.90 (d, J = 2.2 Hz, 1H), 6.82 (dd, J = 8.6, 2.2 Hz, 1H), 5.05 (dd, J = 12.9, 5.4 Hz, 1H), 3.67 (t, J = 5.5 Hz, 4H), 3.56 (dd, J = 10.3, 7.2 Hz, 1H), 3.54-3.46 (m, 1H), 3.40 (dt, J = 10.3, 7.5 Hz, 1H), 3.15 (dd, J = 10.4, 6.8 Hz, 1H), 3.04 (d, J = 10.9 Hz, 1H), 2.97 (d, J = 11.0 Hz, 1H), 2.88 (ddd, J = 17.4, 14.1, 5.5 Hz, 1H), 2.67-2.57 (m, 2H), 2.59-2.51 (m, 1H), 2.50-2.40 (m, 1H), 2.37 (d, J = 7.6 Hz, 2H), 2.18-2.08 (m, 1H), 2.09-1.96 (m, 3H), 1.82-1.71 (m, 3H), 1.71-1.61 (m, 4H), 1.64-1.54 (m, 4H). | LCMS: $C_{39}H_{45}N_9O_5$ requires: 719, found: m/z = 720 [M + H]⁺ |
| 152 | ¹H NMR (500 MHz, Acetonitrile-d₃) δ 10.99 (s, 1H), 8.76 (s, 1H), 7.58-7.48 (m, 4H), 7.36 (d, J = 20.8 Hz, 1H), 7.19 (d, J = 8.1 Hz, 2H), 6.64 (d, J = 7.8 Hz, 2H), 5.76 (s, 1H), 5.08-4.88 (m, 2H), 4.42 (s, 1H), 4.35-4.11 (m, 3H), 3.69 (s, 1H), 3.59 (s, 1H), 3.52 (s, 0H), 3.48 (d, J = 8.2 Hz, 1H), 3.46-3.39 (m, 1H), 3.39-3.24 (m, 2H), 3.15-3.05 (m, 1H), 2.99 (dt, J = 24.0, 12.3 Hz, 3H), 2.87 (s, 1H), 2.77 (s, 3H), 2.72 (s, 0H), 2.71-2.58 (m, 2H), 2.48 (s, 1H), 2.40 (d, J = 7.8 Hz, 2H), 1.87 (s, 2H), 1.79 (d, J = 11.0 Hz, 1H), 1.69 (s, 8H), 1.27 (s, 2H), 1.15-1.04 (m, 0H), 0.84 (d, J = 6.6 Hz, 1H). | LCMS: $C_{43}H_{53}N_{11}O_5$ requires: 803, found: m/z = 804 [M + H]⁺ |
| 156 | ¹H NMR (500 MHz, DMSO-d₆) δ 11.20 (s, 1H), 11.07 (s, 1H), 7.77 (s, 1H), 7.67 (s, 1H), 7.51 (d, J = 8.3 Hz, 2H), 7.36-7.31 (m, 1H), 7.18 (d, J = 8.2 Hz, 2H), 6.94 (d, J = 8.6 Hz, 1H), 6.86-6.79 (m, 1H), 6.65 (dd, J = 8.7, 2.2 Hz, 1H), 5.30 (dd, J = 12.9, 5.4 Hz, 1H), 4.34 (dd, J = 39.6, 12.9 Hz, 2H), 3.67-3.54 (m, 4H), 3.33 (s, 2H), 3.12-2.84 (m, 6H), 2.77-2.58 (m, 7H), 2.29-2.14 (m, 2H), 2.05-1.92 (m, 3H), 1.88-1.49 (m, 14H), 1.33-1.23 (m, 3H). | LCMS: $C_{44}H_{56}N_{12}O_5$ requires 832, found: m/z = 833 [M + H]⁺. |
| 157 | ¹H NMR (500 MHz, Acetonitrile-d₃) δ 8.92 (s, 1H), 7.67-7.52 (m, 4H), 7.22 (d, J = 8.4 Hz, 2H), 7.10 (d, J = 7.2 Hz, 1H), 7.03 (d, J = 8.5 Hz, 1H), 5.04-4.93 (m, 1H), 4.76-4.63 (m, 1H), 4.41 (d, J = 12.9 Hz, 1H), 4.27 (d, J = 13.4 Hz, 1H), 4.22-4.09 (m, 2H), 4.07-3.91 (m, 1H), 3.71 (t, J = 10.8 Hz, 1H), 3.48-3.16 (m, 4H), 3.06 (dt, J = 33.2, 12.3 Hz, 1H), 2.91-2.70 (m, 6H), 2.19-2.07 (m, 1H), 1.93-1.40 (m, 8H). | LCMS: $C_{40}H_{45}N_{11}O_7$ requires: 791, found: m/z = 792 [M + H]⁺. |
| 158 | ¹H NMR (500 MHz, Acetonitrile-d₃) δ 9.07 (d, J = 22.0 Hz, 1H), 7.75 (t, J = 7.9 Hz, 1H), 7.58-7.44 (m, 4H), 7.31 (d, J = 8.5 Hz, 1H), 7.21 (d, J = 8.2 Hz, 2H), 5.21-4.92 (m, 3H), 4.59 (d, J = 13.3 Hz, 1H), 4.32-4.24 (m, 1H), 4.17 (d, J = 13.5 Hz, 1H), 3.94 (d, J = 13.6 Hz, 1H), 3.72 (tt, J = 10.0, 4.0 Hz, 1H), 3.48-3.29 (m, 4H), 3.29-3.01 (m, 3H), 2.20-2.07 (m, 1H), 2.02-1.43 (m, 9H). | LCMS: $C_{40}H_{44}N_{10}O_8$ requires: 792, found: m/z = 793 [M + H]⁺. |
| 160 | ¹H NMR (500 MHz, Acetonitrile-d₃) δ 11.17 (s, 1H), 8.89 (s, 1H), 7.66 (dd, J = 13.4, 8.3 Hz, 3H), 7.59 (d, J = 3.8 Hz, 1H), 7.41 (s, 1H), 7.24 (d, J = 8.1 Hz, 2H), 6.98 (d, J = 2.3 Hz, 1H), 6.83 (dd, J = 8.6, 2.2 Hz, 1H), 5.80 (s, 1H), 4.96 (dd, J = 12.1, 5.3 Hz, 1H), 4.47 (d, J = 12.3 Hz, 3H), 3.88-3.65 (m, 3H), 3.59 (t, J = 8.7 Hz, 1H), 3.52-3.18 (m, 5H), 3.10-2.62 (m, 8H), 1.38-1.16 (m, 2H). | LCMS: $C_{40}H_{47}N_9O_6$ requires: 749, found: m/z = 750 [M + H]⁺. |

TABLE 2-continued

Physical Data for the Example Compounds of Table 1.

| Compound No. | $^1$H NMR | Mass Spec (LCMS) |
|---|---|---|
| 161 | $^1$H NMR (500 MHz, Acetonitrile-d$_3$) δ 11.19 (s, 1H), 10.26 (s, 1H), 8.90 (s, 1H), 7.71-7.60 (m, 3H), 7.55 (s, 1H), 7.46 (s, 1H), 7.24 (d, J = 8.4 Hz, 2H), 6.97 (d, J = 2.3 Hz, 1H), 6.82 (dd, J = 8.5, 2.3 Hz, 1H), 5.87 (s, 1H), 4.96 (dd, J = 12.2, 5.4 Hz, 1H), 3.86-3.63 (m, 10H), 3.58 (td, J = 9.5, 8.4, 3.3 Hz, 1H), 3.47 (q, J = 9.2, 8.7 Hz, 1H), 3.34-3.17 (m, 3H), 3.11-2.62 (m, 6H), 2.20-2.00 (m, 4H). | LCMS: C$_{38}$H$_{43}$N$_9$O$_6$ requires: 721, found: m/z = 722 [M + H]$^+$. |
| 173 | $^1$H NMR (500 MHz, DMSO-d$_6$) δ 11.35 (s, 1H), 10.86 (s, 1H), 9.02 (s, 1H), 8.71 (d, J = 8.2 Hz, 1H), 8.36 (d, J = 2.6 Hz, 1H), 7.88 (d, J = 8.7 Hz, 1H), 7.76 (s, 1H), 7.73-7.55 (m, 3H), 7.46 (dd, J = 9.0, 2.6 Hz, 1H), 7.32 (d, J = 17.4 Hz, 1H), 7.20 (d, J = 8.1 Hz, 2H), 4.84-4.69 (m, 1H), 4.46 (d, J = 13.2 Hz, 1H), 4.25 (d, J = 13.4 Hz, 1H), 4.01 (d, J = 12.8 Hz, 3H), 3.45-3.24 (m, 4H), 3.22-3.02 (m, 5H), 2.93 (t, J = 12.4 Hz, 3H), 2.81 (qd, J = 14.0, 12.4, 4.6 Hz, 2H), 2.19 (qd, J = 15.0, 14.0, 5.3 Hz, 2H), 2.09-1.82 (m, 8H), 1.75 (dd, J = 38.7, 21.6 Hz, 3H), 1.61-1.42 (m, 1H), 1.34 (dt, J = 16.9, 10.8 Hz, 3H). | LCMS: C$_{39}$H$_{50}$N$_{10}$O$_5$ requires 738.9, found: m/z = 739.8 [M + H]$^+$ |
| 174 | $^1$H NMR (500 MHz, Acetonitrile-d$_3$) δ 11.13 (s, 1H), 10.49 (s, 1H), 8.89 (s, 1H), 7.67 (dd, J = 8.4, 3.7 Hz, 3H), 7.58 (s, 1H), 7.40 (s, 1H), 7.25 (d, J = 8.4 Hz, 2H), 6.98 (d, J = 2.3 Hz, 1H), 6.87-6.80 (m, 1H), 5.79 (s, 1H), 4.96 (dd, J = 12.1, 5.4 Hz, 1H), 4.58 (d, J = 13.0 Hz, 1H), 4.24 (d, J = 13.5 Hz, 1H), 3.90-3.64 (m, 4H), 3.64-3.41 (m, 6H), 3.34-3.21 (m, 4H), 3.14 (t, J = 12.7 Hz, 2H), 2.94 (d, J = 16.1 Hz, 5H), 2.89-2.67 (m, 8H), 1.79 (s, 5H), 1.59 (d, J = 12.4 Hz, 1H), 1.42-1.29 (m, 2H). | LCMS: C$_{40}$H$_{47}$N$_9$O$_6$ requires: 749.9, found: m/z = 750.9 [M + H]$^+$ |
| 175 | $^1$H NMR (500 MHz, DMSO-d$_6$) δ 11.33 (s, 1H), 11.08 (s, 1H), 7.93-7.81 (m, 1H), 7.74 (s, 1H), 7.66 (d, J = 8.4 Hz, 1H), 7.58 (d, J = 8.2 Hz, 2H), 7.46-7.34 (m, 1H), 7.21 (d, J = 8.2 Hz, 2H), 6.93 (d, J = 2.1 Hz, 1H), 6.84 (dd, J = 8.5, 2.1 Hz, 1H), 5.07 (dd, J = 13.0, 5.4 Hz, 1H), 4.94 (t, J = 5.3 Hz, 1H), 4.53 (d, J = 13.6 Hz, 1H), 4.20 (d, J = 14.0 Hz, 1H), 3.82 (dt, J = 11.0, 4.2 Hz, 1H), 3.59 (t, J = 8.8 Hz, 1H), 3.55-5.39 (m, 5H), 3.29-3.23 (m, 1H), 3.18 (dd, J = 9.9, 6.4 Hz, 1H), 3.07 (d, J = 10.6 Hz, 1H), 2.99 (d, J = 10.8 Hz, 1H), 2.90 (ddd, J = 17.4, 14.1, 5.6 Hz, 1H), 2.71-2.60 (m, 3H), 2.40 (d, J = 7.7 Hz, 3H), 2.25-2.14 (m, 3H), 2.08-1.98 (m, 3H), 1.86-1.60 (m, 5H). | LCMS: C$_{40}$H$_{45}$N$_9$O$_6$F$_2$ requires: 785.9, found: m/z = 786.8 [M + H]$^+$ |
| 176 | $^1$H NMR (500 MHz, DMSO-d$_6$) δ 11.47 (d, J = 10.1 Hz, 1H), 11.09 (s, 1H), 9.10 (s, 1H), 7.79 (s, 1H), 7.71 (d, J = 8.2 Hz, 3H), 7.36 (d, J = 23.8 Hz, 2H), 7.24 (d, J = 8.2 Hz, 2H), 6.98 (d, J = 2.1 Hz, 1H), 6.87 (dd, J = 8.5, 2.2 Hz, 1H), 5.08 (dd, J = 12.8, 5.5 Hz, 1H), 4.60 (dd, J = 35.6, 6.2 Hz, 4H), 3.83 (s, 2H), 3.78 (dd, J = 10.2, 7.3 Hz, 1H), 3.70 (t, J = 15.4 Hz, 3H), 3.65-3.53 (m, 5H), 3.15 (dd, J = 20.9, 10.6 Hz, 2H), 2.97-2.75 (m, 4H), 2.62 (d, J = 3.4 Hz, 2H), 2.31 (t, J = 7.3 Hz, 3H), 2.14-2.01 (m, 3H), 2.01-1.83 (m, 4H). | LCMS: C$_{40}$H$_{45}$N$_9$O$_6$ requires: 747.9, found: m/z = 748.8 [M + H]$^+$ |
| 193 | $^1$H NMR (500 MHz, Acetonitrile-d$_3$) δ 11.13 (s, 1H), 10.41 (s, 1H), 8.89 (s, 1H), 7.67 (dd, J = 8.4, 3.7 Hz, 4H), 7.58 (s, 1H), 7.50-7.36 (m, 1H), 7.25 (d, J = 8.2 Hz, 2H), 6.98 (d, J = 2.3 Hz, 1H), 6.82 (dd, J = 8.6, 2.3 Hz, 1H), 5.79 (s, 1H), 4.96 (dd, J = 12.1, 5.4 Hz, 1H), 4.58 (d, J = 13.4 Hz, 1H), 4.24 (d, J = 13.7 Hz, 1H), 3.85-3.65 (m, 4H), 3.58 (d, J = 8.1 Hz, 2H), 3.54-3.38 (m, 4H), 3.30 (t, J = 9.1 Hz, 2H), 3.14 (t, J = 12.0 Hz, 2H), 2.98 (d, J = 41.7 Hz, 5H), 2.90-2.68 (m, 8H), 1.80 (d, J = 19.1 Hz, 5H), 1.59 (d, J = 11.7 Hz, 2H), 1.48-1.27 (m, 2H). | LCMS: C$_{40}$H$_{47}$N$_9$O$_6$ requires: 749, found: m/z = 750 [M + H]$^+$. |
| 194 | $^1$H NMR (500 MHz, DMSO-d$_6$) δ 11.30 (s, 1H), 10.86 (s, 1H), 8.71 (d, J = 8.1 Hz, 1H), 8.36 (s, 1H), 7.88 (d, J = 8.7 Hz, 1H), 7.79 (s, 1H), 7.69 (s, 1H), 7.58 (d, J = 7.9 Hz, 2H), 7.46 (d, J = 8.8 Hz, 1H), 7.36 (s, 1H), 7.19 (d, J = 8.2 Hz, 2H), 4.75 (ddd, J = 13.1, 8.2, 5.4 Hz, 1H), 4.42-4.25 (m, 2H), 4.01 (d, J = 12.9 Hz, 2H), 3.65 (dd, J = 13.8, 7.9 Hz, 3H), 3.27 (t, J = 8.3 Hz, 3H), 3.17-2.87 (m, 6H), 2.86-2.70 (m, 5H), 2.27-2.10 (m, 2H), 2.11-1.69 (m, 12H), 1.68-1.47 (m, 2H), 1.30 (d, J = 52.1 Hz, 3H). | LCMS: C$_{42}$H$_{54}$N$_{12}$O$_5$ requires: 806, found: m/z = 807 [M + H]$^+$. |
| 195 | $^1$H NMR (500 MHz, DMSO-d$_6$) δ 11.19 (s, 1H), 10.85 (s, 1H), 8.71 (d, J = 8.2 Hz, 1H), 8.32 (d, J = 2.9 Hz, 1H), 7.85 (d, J = 8.8 Hz, 1H), 7.76 (s, 1H), 7.67 (s, 1H), 7.51 (d, J = 8.1 Hz, 2H), 7.42 (dd, J = 8.9, 2.9 Hz, 1H), 7.34 (s, 1H), 7.18 (d, J = 8.2 Hz, 2H), 4.75 (ddd, J = 13.2, 8.2, 5.4 Hz, 1H), 4.34 (ddd, J = 39.7, 12.8 Hz, 2H), 3.96 (d, J = 12.5 Hz, 2H), 3.62 (d, J = 11.0 Hz, 1H), 3.28 (dd, J = 14.4, 7.4 Hz, 5H), 3.11-2.76 (m, 4H), 2.73 (s, 3H), 2.19 (dd, J = 10.7, 5.3 Hz, 3H), 2.08-1.93 (m, 3H), 1.89-1.71 (m, 8H), 1.59 (d, J = 29.1 Hz, 4H), 1.23 (d, J = 14.3 Hz, 5H). | LCMS: C$_{42}$H$_{54}$N$_{12}$O$_5$ requires: 806, found: m/z = 807 [M + H]$^+$. |
| 196 | $^1$H NMR (500 MHz, acetonitrile-d$_3$) δ 11.17 (s, 1H), 8.91 (s, 1H), 7.65 (d, J = 8.2 Hz, 2H), 7.58 (s, 1H), 7.41 (s, 1H), 7.24 (d, J = 8.2 Hz, 2H), 6.84 (d, J = 8.6 Hz, 1H), 6.41 (s, 1H), 6.33 (d, J = 8.7 Hz, 1H), 5.79 (s, 1H), 5.14 (dd, J = 12.9, 5.3 Hz, 1H), 3.81-3.65 (m, 5H), 3.61 (t, J = 8.3 Hz, 1H), 3.49-3.39 (m, 2H), 3.38-3.31 (m, 4H), 3.27-3.20 (m, 2H), 3.20-3.12 (m, 1H), 3.10-2.96 (m, 2H), 2.95-2.80 (m, 3H), 2.80-2.67 (m, 2H), 2.54-2.01 (m, 6H), 1.92-1.80 (m, 1H), 1.78-1.70 (m, 2H), 1.70-1.65 (m, 4H). | LCMS: C$_{39}$H$_{48}$N$_{10}$O$_4$ requires 720, found: m/z = 721 [M + H]$^+$. |
| 197 | $^1$H NMR (500 MHz, acetonitrile-d$_3$) δ 11.18 (s, 1H), 9.77 (s, 1H), 8.91 (s, 1H), 7.65 (d, J = 8.2 Hz, 2H), 7.58 (s, 1H), 7.41 (s, 1H), 7.24 (d, J = 8.2 Hz, 2H), 6.85 (d, J = 8.5 Hz, 1H), 6.41 (s, 1H), 6.33 (d, J = 8.5 Hz, 1H), 5.80 (s, 1H), 5.15 (dd, J = 12.8, 5.4 Hz, 1H), 3.78-3.70 (m, 5H), 3.61 (t, J = 8.5 Hz, 1H), 3.49-3.39 (m, 2H), 3.38-3.31 (m, 4H), 3.28-3.20 (m, 2H), 3.20-3.13 (m, 1H), 3.12-2.96 (m, 2H), 2.92-2.84 (m, 3H), 2.80-2.71 (m, 2H), 2.57-2.03 (m, 6H), 1.92-1.79 (m, 1H), 1.80-1.71 (m, 2H), 1.71-1.65 (m, 4H). | LCMS: C$_{39}$H$_{48}$N$_{10}$O$_4$ requires 720, found: m/z = 721 [M + H]$^+$. |
| 198 | $^1$H NMR (500 MHz, acetonitrile-d$_3$) δ 11.14 (s, 1H), 8.99 (s, 1H), 8.93 (s, 1H), 7.66-7.56 (m, 3H), 7.43 (s, 1H), 7.23 (d, J = 8.2 Hz, 2H), 6.86 (d, J = 8.4 Hz, 1H), 6.45 (s, 1H), 6.37 (s, 1H), 5.84 (s, 1H), 5.15 (dd, J = 12.8, 5.4 Hz, 1H), 4.42 (d, J = 12.8 Hz, 1H), 4.31 (d, J = 13.7 Hz, 1H), 3.77-3.67 (m, 3H), 3.63-3.59 (m, 1H), 3.50-3.13 (m, 10H), 3.13-2.96 (m, 4H), 2.95-2.41 (m, 7H), 2.36-2.32 (m, 1H), 2.17-2.08 (m, 6H), 1.94-1.77 (m, 6H), 1.68-1.64 (m, 1H). | LCMS: C$_{43}$H$_{54}$N$_{12}$O$_5$ requires 818, found: m/z = 819 [M + H]$^+$. |
| 199 | $^1$H NMR (500 MHz, acetonitrile-d$_3$) δ 11.14 (s, 1H), 9.07 (s, 1H), 8.92 (s, 1H), 7.66-7.56 (m, 3H), 7.43 (s, 1H), 7.23 (d, J = 8.3 Hz, 2H), 6.85 (d, J = 8.4 Hz, 1H), 6.44 (s, 1H), 6.36 (s, 1H), 5.83 (s, 1H), 5.15 (dd, J = 12.8, 5.2 Hz, 1H), 4.42 (d, J = 12.4 Hz, 1H), 4.31 (d, J = 13.5 Hz, 1H), 3.77-3.67 (m, 3H), 3.62-3.56 (m, 1H), 3.50-3.12 (m, 10H), 3.13-2.96 (m, 4H), 2.95-2.68 (m, 6H), 2.69-2.19 (m, 6H), 2.18-2.09 (m, 5H), 1.97-1.85 (m, 5H), 1.70-1.64 (m, 1H). | LCMS: C$_{43}$H$_{54}$N$_{12}$O$_5$ requires 818, found: m/z = 819 [M + H]$^+$. |
| 204 | $^1$H NMR (500 MHz, DMSO-d$_6$) δ 11.07 (s, 1H), 10.72 (s, 1H), 8.57 (s, 2H), 7.75 (s, 1H), | LCMS: C$_{40}$H$_{48}$N$_{14}$O$_6$ |

TABLE 2-continued

Physical Data for the Example Compounds of Table 1.

| Compound No. | $^1$H NMR | Mass Spec (LCMS) |
|---|---|---|
| | 7.66 (d, J = 8.8 Hz, 2H), 7.34 (s, 1H), 6.92 (d, J = 2.1 Hz, 1H), 6.84 (dd, J = 8.4, 2.1 Hz, 1H), 5.06 (dd, J = 12.9, 5.4 Hz, 1H), 4.22 (dd, J = 37.3, 13.0 Hz, 2H), 3.79-3.40 (m, 9H), 3.28-3.05 (m, 16H), 2.97-2.82 (m, 2H), 2.67 (s, 4H), 2.24-1.95 (m, 2H), 1.78 (q, J = 5.6, 5.1 Hz, 5H), 1.52 (s, 2H), 1.25 (s, 4H). | requires: 820, found: m/z = 821 [M + H]$^+$. |

Biological Example 1

Cellular BTK Degradation Assay

BTK levels are determined using Cisbio Total-BTK HTRF (Homologous Time-Resolved Fluorescence) kit (63ADK064PEG) according to the manufacturer's protocol. Briefly, cells are incubated in 1× supplied lysis buffer for 30 minutes. In an opaque white low volume 96-well plate (Cisbio, 66PL96005), cell lysate is combined with two different specific BTK antibodies, one conjugated with Eu$^{3+}$-Cryptate FRET donor and one conjugated with d2 FRET acceptor. Assay controls include wells containing cell lysate with only the Eu$^{3+}$-Cryptate FRET donor antibody and wells containing both HTRF antibodies and lysis buffer without cells or control lysate provided by Cisbio. HTRF ratio is calculated as (acceptor signal at 665 nm/donor signal at 620 nm)×10$^4$. Background HTRF levels are determined from the control well containing the donor, but no acceptor, antibody. Background HTRF levels are subtracted from all samples. Readouts are reported as HTRF levels relative to HTRF levels of DMSO-treated cells. Four-parameter non-linear regressions were performed in GraphPad Prism 7.02 to obtain DC50 values.

Biological Example 2

Human Dosing of Compound 149

Compound 149 was administered to human patients in a Phase 1a/1b trial investigating safety and tolerability in relapsed and refractory B cell malignancies. Compound 149 was administered as a once daily oral dose first in an accelerated Phase 1a dose escalation starting at 100 mg on Day 1. The first dose levels are explored in a single patient cohort until a grade 2 adverse event has been observed. Thereafter, a traditional 3+3 escalation design is used. This 100 mg starting dose was predicted to provide similar exposure as that observed in non-human primate studies. Once a dose is selected based on all safety, efficacy, pharmacokinetic, and pharmacodynamic data available, the trial will expand in up to five expansion cohorts.

Seven patients were screened, one patient completed the first cohort, and five patients were enrolled in the second cohort. Four patients had chronic lymphocytic leukemia or small cell lymphocytic leukemia. One patient had mantle cell lymphoma. One patient had Waldenstrom's macroglobulinemia. All patients had at least two prior lines of therapy. All patients had failed ibrutinib therapy. Two patients had failed pirtobrutinib therapy. In the second cohort, one patient was removed from the study on Day 15. Two additional patients were then enrolled in the second cohort.

Plasma concentrations of compound 149 were measured and provided in FIG. 1. All patients showed rapid rise of concentrations and achieved steady state plasma concentrations by Day 8.

Figure 2:
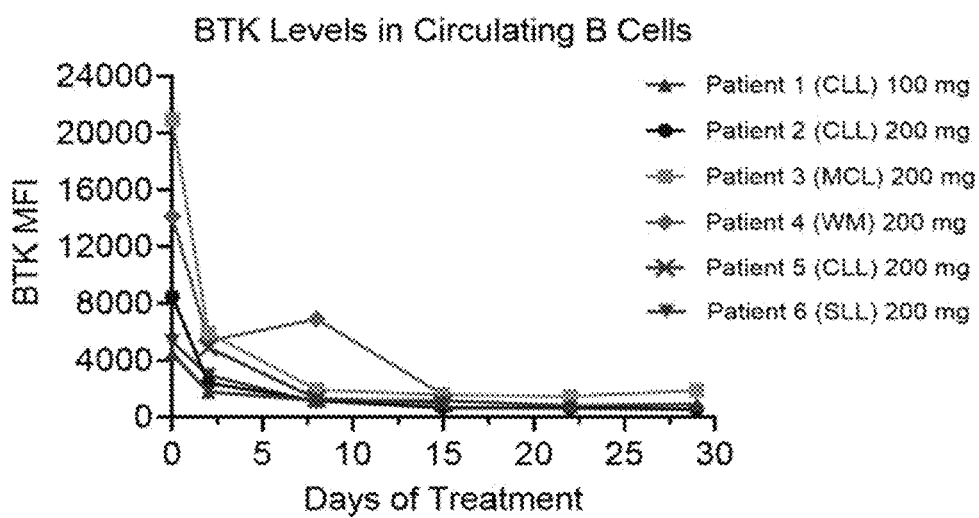
FIG. 2 provides BTK levels in patient circulating B cells following daily orally dosing at the indicated levels.

Plasma levels of Bruton's tyrosine kinase were measured by flow cytometry in circulating B cells, including disease cells and provided in FIG. 2. This mean fluorescence intensity directly correlates with the levels of BTK protein observed in a Western blot. Compound 149 dramatically decreases the level of BTK protein in all patients treated. The patient's BTK levels start at different levels yet, the treatment results in the same level of degradation by Day 15, which is the first measurement after steady state concentration is achieved.

Figure 3:
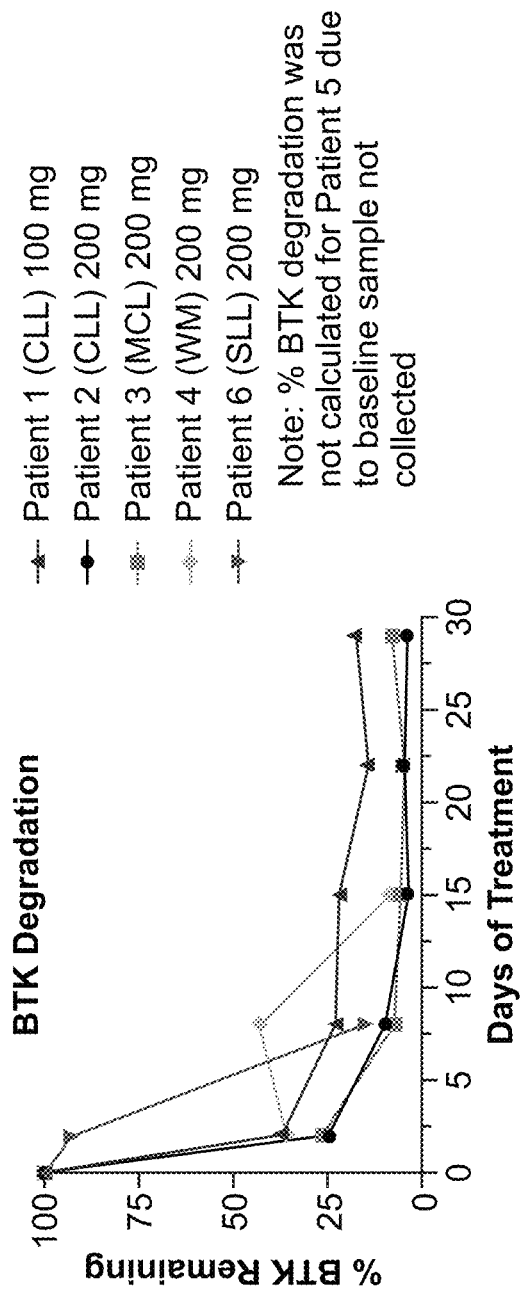
FIG. 3 provides percent BTK levels in patient circulating B cells normalized to baseline levels following daily orally dosing at the indicated levels.

BTK levels are normalized in each patient to 100% and provided in FIG. 3. The 100 mg patient achieved greater than 80% BTK degradation at steady state. All patients at the 200 mg dose level achieved greater than 90% degradation at steady state.

The data is summarized in Table 3 below which provides the average percent BTK degradation during the last 2 weeks of the first cycle (namely Days 15, 22, and 29). In Cohort 2 (200 mg), well above 90% of BTK degradation was achieved during the steady state.

In humans, compound 149 is well-tolerated with no dose limiting toxicities at 100 mg and 200 mg per dose. Greater than 90% BTK degradation was observed in all patients at 200 mg per dose.

TABLE 3

| | | | BTK Degradation | | | | | | |
|---|---|---|---|---|---|---|---|---|---|
| Dose | Patient | Baseline | Day 2 | Day 8 | Day 15 | Day 22 | Day 29 | Avg. Steady State* | Day 56 |
| 100 mg | 1 (CLL) | 0 | 62.8 | 76.9 | 78.0 | 85.5 | 82.0 | 81.8 | 81.4 |
| 200 mg | 2 (CLL) | 0 | 75.1 | 90.5 | 96.1 | 95.4 | 96.1 | 95.9 | 96.0 |
| | 3 (MCL) | 0 | 74.0 | 92.7 | 94.6 | 95.4 | 92.3 | 94.1 | 94.7 |
| | 4 (WM) | 0 | 63.6 | 56.8 | 91.5 | | | 91.5 | |
| | 5 (CLL) | N/A | | | | | | | |
| | 6 (SLL) | 0 | 6.9 | 85.1 | | | | | |

Biological Example 3

Oral Dosing of Compound 149

This trial was conducted at 12 centers, including Memorial Sloan Kettering Cancer Center, MD Anderson Cancer Center, City of Hope (Duarte, California), National Institutes of Health Clinical Center, Sarah Cannon Research Institute, Colorado Blood Cancer Institute, Florida Cancer Specialists, Tennessee Oncology, University of California (San Francisco), University of California (Irvine), OSU Wexner Medical Center, and Swedish Cancer Institute (Seattle).

Patients were treated at four different dosage levels of Compound 149: dose level 1 (100 mg), dose level 2 (200 mg), dose level 3 (300 mg), and dose level 4 (400 mg). The objective of the study was to assess safety and tolerability, to identify maximum tolerated dose, and to evaluate PK/PD.

Patients evaluated in this study were treated for diseases or disorders selected from the group consisting of: chronic lymphocytic leukemia (CLL) with BTK C481 mutation (n 20); CLL without BTK C481 mutation (n~20); mantle cell lymphoma (MCL), marginal zone lymphoma (MZL), Waldenstrom's macroglobulinemia (WM) (n~20); follicular lymphoma (FL) (n~20); and diffuse large B cell lymphoma (DLBCL) (n~20). Tables 4 and 5 below summarize patient characteristics. Heavily pretreated patient population, including double-refractory CLL patients.

TABLE 4

| Characteristics | Overall Population (N = 21)** | CLL (N = 13) | Non-CLL (N = 7) |
|---|---|---|---|
| Median Age, years (range) | 76.0 (61-92) | 76 (65-86) | 77 (67-92) |
| Female, n (%) | 7 (33.3%) | 7 (53.8%) | 0 |
| Male, n (%) | 14 (66.7%) | 6 (46.2%) | 7 (100%) |
| Prior Therapy*, median (range) | 4.5 (1-8) | 6.0 (2-8) | 2.0 (1-5) |
| BTK inhibitor, n (%) | 16 (76.2%) | 12 (92.3%) | 4 (57.1%) |
| BCL2 inhibitor, n (%) | 7 (33.3%) | 53.8%) | 0 |

TABLE 5

| Type of Disease | Cohort 1 | Cohort 2 | Cohort 3 | Total |
|---|---|---|---|---|
| Chronic lymphocytic leukemia | 8 (66.7%) | 3 (50%) | 2 (66.7%) | 13 (61.9%) |
| mantle cell lymphoma | 1 (8.3%) | 1 (16.7%) | 1 (33.3%) | 3 (14.3%) |
| diffuse large B cell lymphoma | 2 (16.7%) | 1 (16.7%) | 0 (0%) | 3 (14.3%) |
| Waldenstrom's macroglobulinemia | 0 (0%) | 1 (16.7%) | 0 (0%) | 1 (4.8%) |
| TBD*** | 1 (8.3%) | 0 (0%) | 0 (0%) | 1 (4.8%) |

Figure 4:
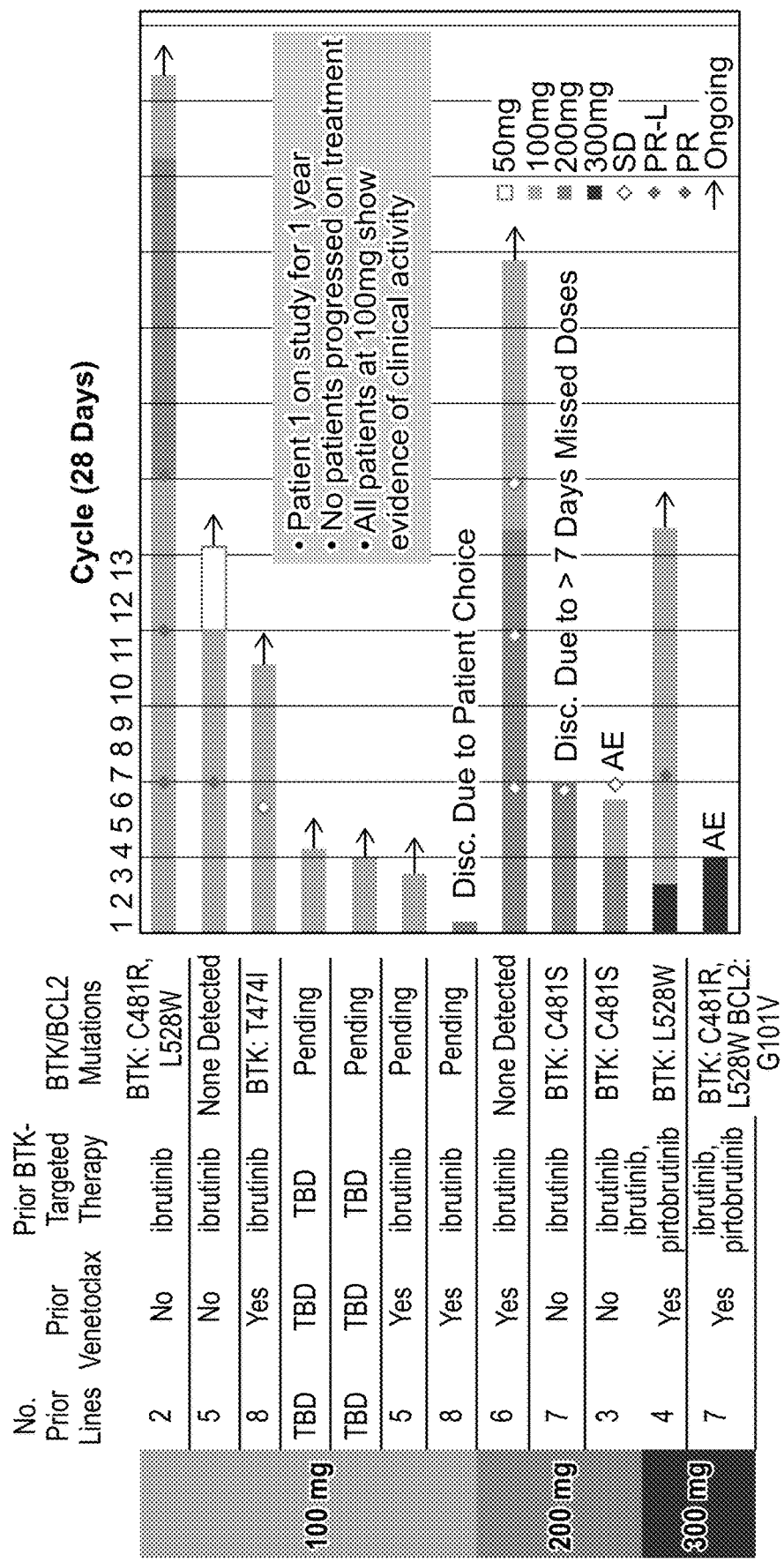
FIG. 4 shows Compound 149's durable benefit in CLL patients with a median of six prior treatments.
Figure 5:
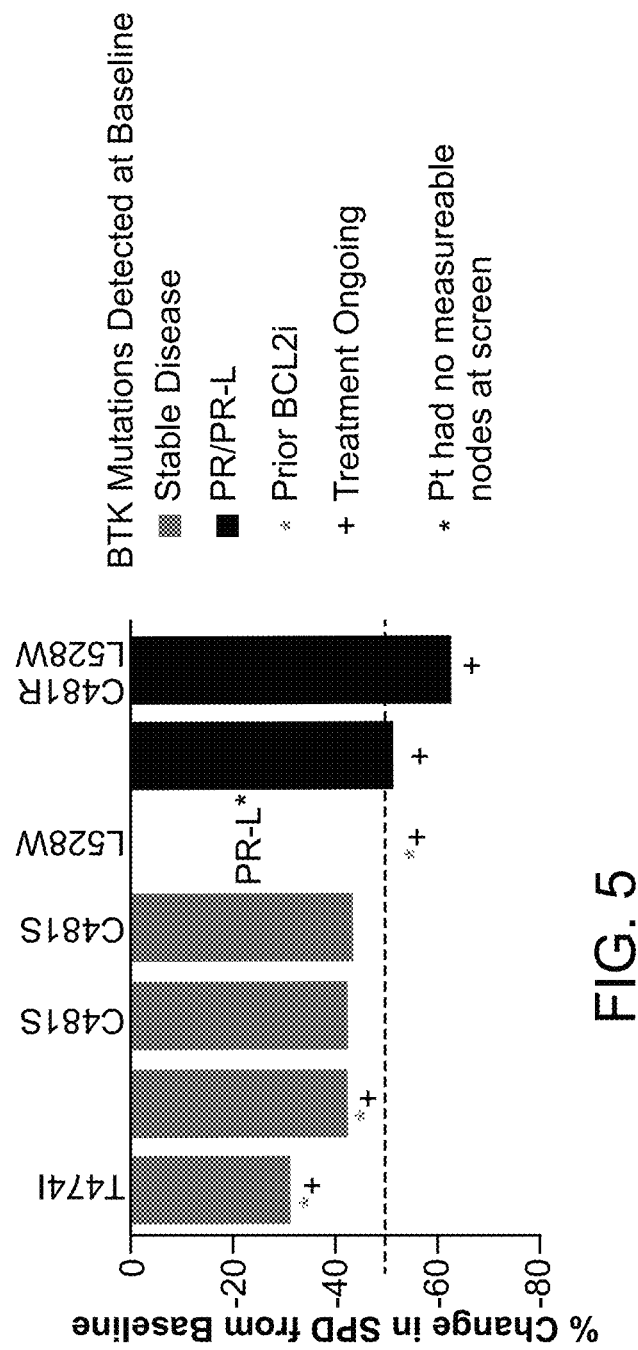
FIG. 5 shows Compound 149 in Phase 1a: Positive initial findings in CLL support expansion at 100 mg.
Figure 6:
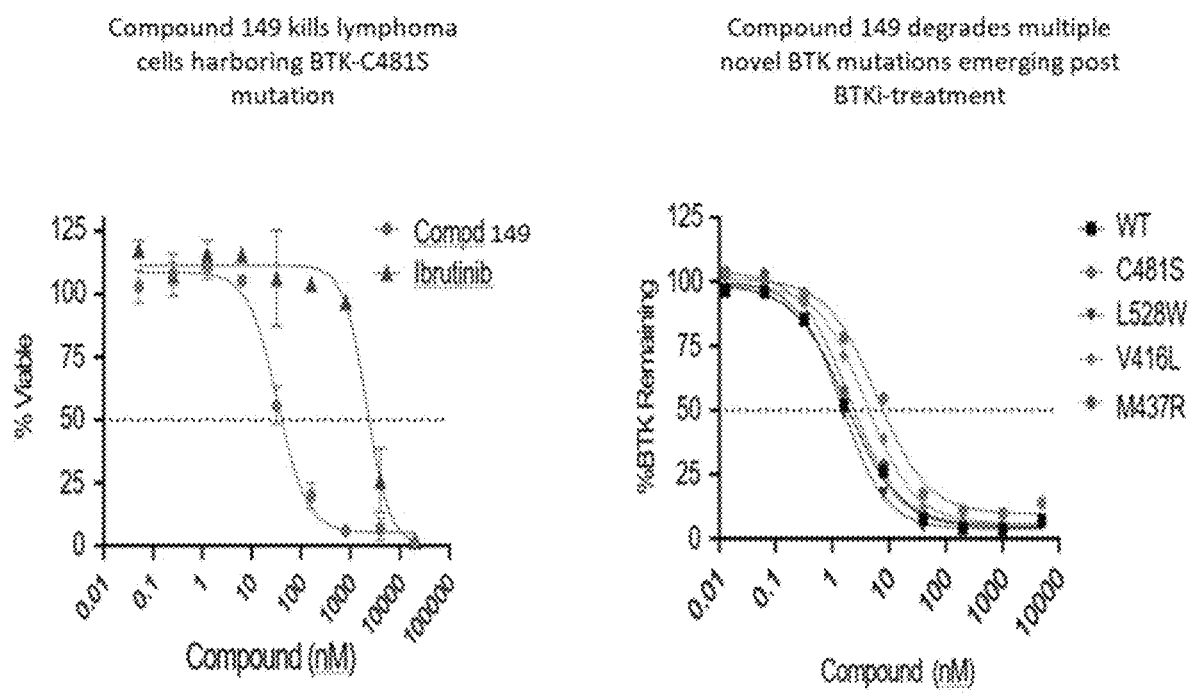
FIG. 6 provides the effect of Compound 149 as a degrader to resolve inhibitor resistance in lymphoma cells harboring BTK-C481S mutation and multiple novel BTK mutations emerging post BTKi-treatment.

*Prior therapies were not entered into the database for all enrolled patients at the time of Data Cut. Some data pending/ongoing.
**One patient's disease type wasn't identified in the EDC at the time of extract, but disease type was coded based on source data
***One subject was screened into the study, but the indication and cohort weren't entered in the EDC at the time of data extract Efficacy Evaluations All the patients with CLL with prior therapy dosed with 100 mg of Compound 149 showed clinical activity (see, FIG. 4). As shown in FIG. 5, data from all evaluable CLL patients showed nodal reductions and/or lymphocytosis observed in all patients treated, responses in patients with resistance mutations to covalent and non-covalent BTK inhibitors, and responses from double-refractory patient who had prior BCL2 inhibitor therapy. Data shown in FIG. 6 confirms that Compound 149 is a potent BTK degrader to solve inhibitor resistance observed with prior therapy. Compound 149 kills lymphoma cells harboring BTK-C481S mutation and degrades multiple novel BTK mutations emerging post BTKi-treatment.

Safety Observations

Safety population included 19 subjects, and data is summarize in Table 6 below. Two subjects were assigned to the 100 mg cohort but treatment was not entered in the electronic data capture (EDC) at time of extract. Dose limiting toxicity was observed at 300 mg in a CLL patient; a cognitive AE was believed to be related to immunomodulatory activity. Two AEs of lower grade atrial fibrillation were observed at 100 mg in a patient with MCL, and at 200 mg in a patient with CLL.

TABLE 6

Safety Observations By Dose of Compound 149: All Patients, Grade ≥ 3

| Adverse Event Preferred Term, Grade ≥ 3 | 100 mg (N = 10) n (%) | 200 mg (N = 6) n (%) | 300 mg (N = 3) n (%) |
|---|---|---|---|
| Neutropenia | 1 (10%) | 3 (50%) | 2 (66.7%) |
| Hypertension | 0 (0%) | 1 (16.7%) | 0 (0%) |
| Dyspnea | 0 (0%) | 1 (16.7%) | 0 (0%) |
| Anemia | 1 (10%) | 1 (16.7%) | 0 (0%) |
| Pain in extremity | 0 (0%) | 0 (0%) | 1 (33.3%) |
| *Clostridium difficile* colitis | 0 (0%) | 1 (16.7%) | 0 (0%) |
| *Clostridium difficile* infection | 0 (0%) | 1 (16.7%) | 0 (0%) |
| Cognitive disorder | 0 (0%) | 0 (0%) | 1 (33.3%) |
| Upper resp. tract infection | 0 (0%) | 1 (16.7%) | 0 (0%) |

Biological Example 4

Flow Cytometry Assay for BTK Degradation

Following informed consent, peripheral blood was obtained from all patients for baseline and post Compound 149 therapy assessment of BTK and Ikaros degradation. Patient blood (5 mL) was drawn and immediately fixed in a 5 mL CytoChex™ BCT tube and stored at ambient temperature until assessment via flow cytometry. Blood samples were analyzed within 3 days post sample collection at Precision for Medicine. Additional blood was also drawn into 8 mL BD Vacutainer® CPT™ Cell Preparation Tube with Sodium Citrate. Peripheral blood mononuclear cells (PBMCs) were processed, and viability frozen according to manufacturer's protocol.

For flow staining, 1 mL blood was treated with 1×BD PharmLyse to facilitate red blood cell lysing. Remaining leukocytes were washed with staining buffer (SB) containing Dulbecco's Phosphate Buffered Saline (DPBS) without Calcium or Magnesium, 1% bovine serum albumin (BSA), 10 mM HEPES, 1 mM EDTA, and 0.01% sodium azide. Cell pellet was stained with fluorophore-conjugated cell surface markers antibodies against CD45, CD3, CD4, CD8, CD14, CD16, CD19 and CD56 prepared in BD Brilliant Stain buffer for 25 minutes at room temperature.

Following cell surface staining, cells were washed twice with SB and then fixed and permeabilized for one hour at room temperature with eBioscience FoxP3/Transcription Factor Staining Buffer set according to the manufacturer's instructions. Washed cells were then stained with unconjugated BTK antibody made in 1× Permeabilization buffer) for 30 minutes. This was followed by another 30-minute incubation with anti-rabbit Alexa488 secondary antibody also prepared in 1× Permeabilization buffer for BTK detection. After incubation, the cells were washed twice with 1× Permeabilization Buffer and then resuspended in SB. Control samples containing fluorescence minus two markers (FM2) were used for background controls and were stained for all surface markers in the panel excluding BTK. The FM2 does not include the antibody to detect BTK.

The samples were transferred to BD TruCount tubes before acquisition on a BD LSR Fortessa using predetermined BD FACS Diva software (v8.0) application settings. Data analysis was performed using FlowJo software (v10).

Single lymphocytes were gated for B cells (CD19+ CD3−), and the geometric mean fluorescence intensity (MFI) of BTK was calculated. The MFI of B cells in FM2 control was used to quantify background staining. Percent BTK degradation was calculated using the following equation:

% Degradation 100−[100*(BTK $MFI_x$)/(BTK $MFI_y$)]

% Remaining 100*(BTK $MFI_x$)/(BTK $MFI_y$)

BTK $MFI_x$=BTK MFI at time point of interest
BTK $MFI_y$=BTK MFI at pre-dose

List of Materials used for flow cytometry are shown in Table 7 below.

TABLE 7

| Material | Vendor | Vendor Catalog # | Vendor Lot # | RM/PN# | Lot |
|---|---|---|---|---|---|
| 1 × BD PharmLyse | N/A | N/A | 0119703 | PN2236 | 1-03278 |
| FcBlock | Invitrogen | 14-9161-73 | 2161225 | RM3158 | 20-1147 |
| Brilliant Stain Buffer | BD Biosciences | 566349 | 38709 | RM3478 | 20-0477 |
| Staining Buffer, 1% BSA | N/A | N/A | N/A | PN2214 | 1-03263 |
| BD FACSDiva CS&T Beads | BD Biosciences | 655051 | 9042577 | RM3246 | 19-0491 |
| Compensation Beads | Life Technologies | 01-2222-42 | 2268280 | RM3157 | 20-1556 |
| FoxP3 Stain kit | eBioscience | 00-5523-00 | 2178652 | RM3501 | 20-0729 |
| Water | Quality Biological | 351-029-131 | 723901 | RM0924 | 20-1588 |
| BD TruCount ™ Tubes | BD Biosciences | 340334 | 20-1749 | RM3217 | 20-1749 |
| CD19 | BioLegend | 363018 | B313190 | RM3158 | 20-1732 |
| CD56 | BD Biosciences | 563041 | 23877 | RM3158 | 20-1642 |
| CD14 | BioLegend | 301836 | B318037 | RM3158 | 20-1730 |
| CD16 | BioLegend | 360734 | B299811 | RM3158 | 20-1595 |
| BTK unconjugated | CST | 8547S | 13 | RM3158 | 20-1662 |
| Anti-rabbit Alexa488 | BioLegend | 406416 | B294808 | RM3158 | 20-1693 |
| CD8 | BD Biosciences | 560662 | 9331325 | RM3158 | 20-1640 |
| CD4 | BD Biosciences | 560644 | 86585 | RM3158 | 20-1641 |
| CD3 | BD Biosciences | 557943 | 9185576 | RM3158 | 20-1452 |
| CD45 | BD Biosciences | 563792 | 121733 | RM3158 | 20-1639 |

Results

Once a Day Oral Compound 149 Treatment Induced Rapid and Sustained BTK Degradation Inpatients Pharmacodynamic assessment of BTK degradation was performed using a validated 10-color flow cytometry assay. Serial peripheral blood was collected from consented patients upon receiving Compound 149 treatment. Peripheral blood from patients were processed and BTK degradation was assessed using a validated 10-color flow panel. B cells (CD19+CD3−) were gated and BTK MFI were measured. B cell BTK MFI from no antibody control FM2 sample was used to subtract background from each sample. % BTK remaining was calculated relative to Baseline as described in the Methods section.

Figure 7:
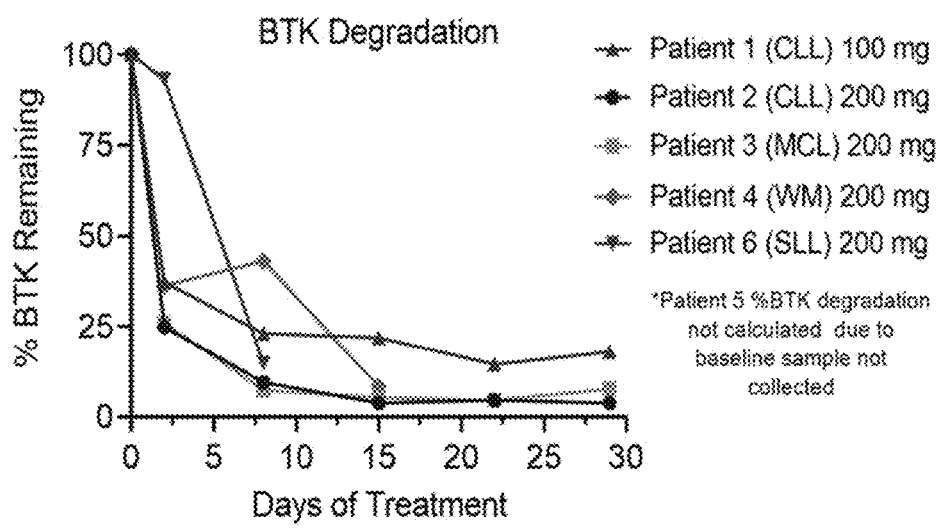
FIG. 7 shows flow cytometry assessment of BTK levels in patients.

In all patients receiving once daily oral regimen of Compound 149, a time-dependent decrease of BTK levels as measured by flow cytometry using BTK MFI in CD19+CD3− B cells were observed (see, FIG. 7). In patients 1, 2, 3, and 4, 62.8-75.1% BTK degradation was observed at 24 hours after receiving the initial dose of Compound 149. Maximum BTK degradation was achieved at steady state Cycle 1 Day 15 where an average of 90.1% BTK degradation (Table 8) was observed in all patients. This level of degradation was sustained through Cycle 1 Day 29 prior to starting Cycle 2.

TABLE 8

BTK degradation in patients

% BTK Degraded

| Dose | Baseline | Day 2 | Day 8 | Day 15 | Day 22 | Day 29 |
|---|---|---|---|---|---|---|
| Patient 1 (100 mg) | 0 | 62.8 | 76.9 | 78.0 | 85.5 | 82.0 |
| Patient 2 (200 mg) | 0 | 75.1 | 90.5 | 96.1 | 95.4 | 96.1 |
| Patient 3 (200 mg) | 0 | 74.0 | 92.7 | 94.6 | 95.4 | 92.3 |
| Patient 4 (200 mg) | 0 | 63.6 | 56.8 | 91.5 | Discontinued due to *PD | |
| Patient 6 (200 mg) | 0 | 6.9 | 85.1 | Samples collected but unavailable during data release | | |
| Average | 0 | 56.5 | 80.4 | 90.1 | 92.1 | 90.1 |

*PD: Progressive disease

Biological Example 5

Oral Dosing of Compound 149

A heavily pre-treated patient with non-GCB (ABC subtype) DLBCL was enrolled in Compound 149 phase 1 dose-escalation. The patient was treated at a single dosage level of Compound 149: dose level 1 (300 mg) for a period of 5 months and ongoing. The objective of the study was to assess safety and tolerability, to identify maximum tolerated dose, and to evaluate PK/PD.

Table 9 as given below describes the baseline demographic and disease characteristics of the patient:

TABLE 9

| Patient | Baseline demographic and disease characteristics |
|---|---|
| Age | 84 |
| Relevant medical history | Aortic regurgitation, diastolic dysfunction, aspergillosis sinus infection |
| Cancer Diagnosis | 1988: Waldenstrom's macroglobulinemia (WM) |
| | 2015: Diffuse large B-Cell lymphoma (DLBCL) ABC subtype |
| Prior treatments for DLBCL | 2015: Rituximab + CHOP followed by focal axillary irradiation |
| | 2017: Rituximab + ICE |
| | 2018: Rituximab, mogamulizumab (anti-CCR4), and magrolimab (anti-CD47) |
| | 2019: Rituximab, ibrutinib, and lenalidomide (RIL) |
| Disease features at study entry | Stage IV, MYD88 mutated and CXCR4 mutated |
| Time on study | Ongoing, Cycle #6 (5 months) |

Response

Figure 8:
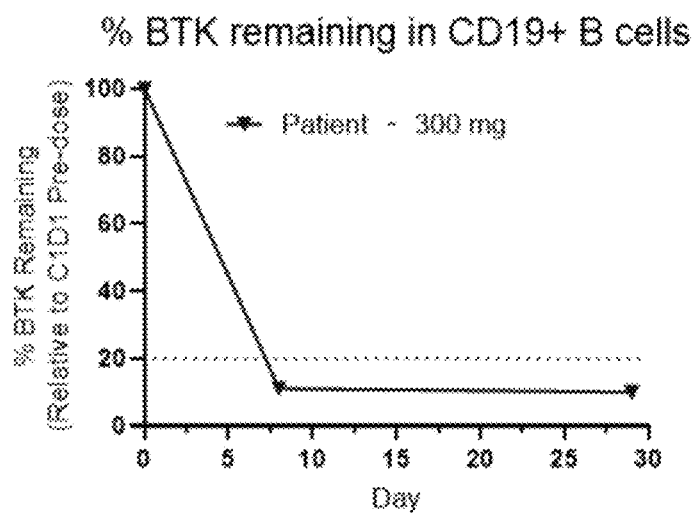
FIG. 8 shows the effect of Compound 149 through a flow cytometry assessment of BTK levels in a patient.
Figure 9:
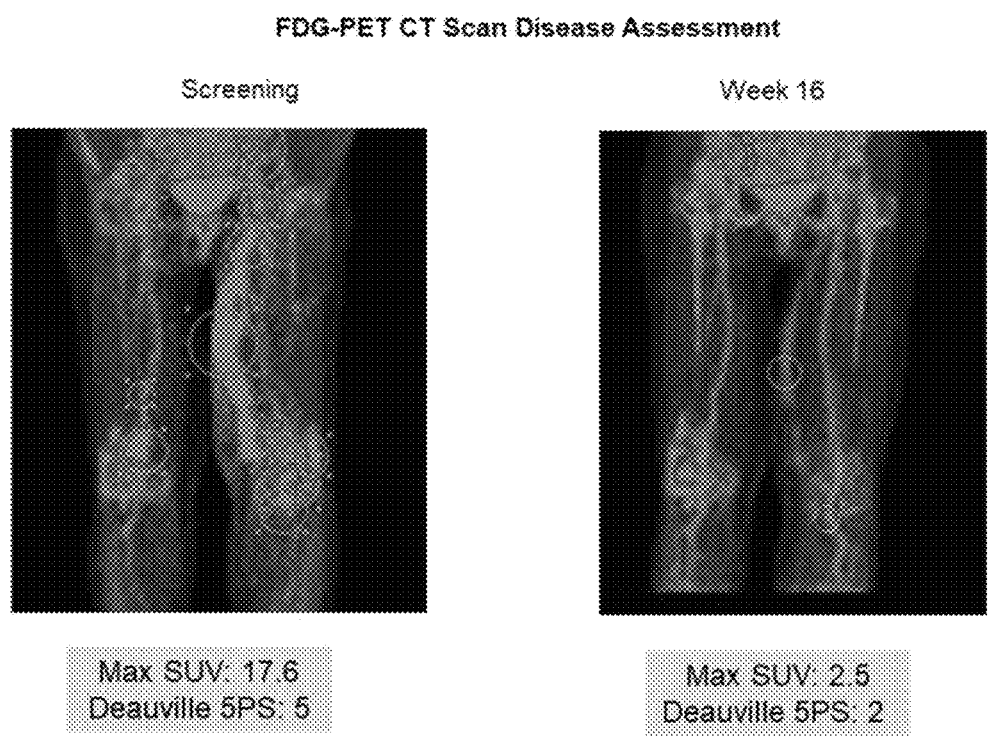
FIG. 9 shows a FDG-PET CT Scan disease assessment at different time points.

The patient's response was checked at 8 weeks and 16 weeks. Per Lugano criteria, there was a complete response at 8 weeks, which was then confirmed at the subsequent 16-week assessment. As shown in FIG. 8, a time-dependent decrease of BTK levels as measured by flow cytometry using BTK MFI in CD19+B cells was observed. Gradual BTK degradation was observed until day 8 day of receiving the 300 mg dose of Compound 149, wherein the maximum BTK degradation was achieved on the 8th day. Consistent with its design, Compound 149 also degraded Ikaros and Aiolos which is responsible for the compound's immunomodulatory activity. Further, this level of BTK degradation was sustained through day 29. In addition, as shown in FIG. 9, a complete confirmed response at the 16-week assessment was seen through the FDG-PET CT Scan Disease Assessment as compared to the screening image. In the 16-week assessment image, maximum standard uptake value (Max SUV) reduced from 17.6 at screening to 2.5 at the 16-week assessment time with the Deauville five-point scale (5PS; Barrington et al., 2010, Eur J Nucl Med Mol Imaging 37 (10): 1824-33) reducing from 5 to 2. Thus, this data confirms that compounds having a dual mechanism of action (BTK and immunomodulatory activity) provides clinical benefit to refractory patients with certain non-Hodgkin's lymphoma such as DLBCL. Further, it was noted that no dose limiting toxicity (DLT) or serious adverse event (SAE) was observed.

Other Embodiments

It is to be understood that the foregoing description is intended to illustrate and not limit the scope of this disclosure, which is defined by the scope of the appended claims. Other aspects, advantages, and modifications are within the scope of the following claims.

What is claimed is:

1. A method of treating cancer in a human subject in need thereof, comprising the step of orally administering to the human subject a daily oral dose of about 50 mg to about 500 mg of a compound of formula I selected from:

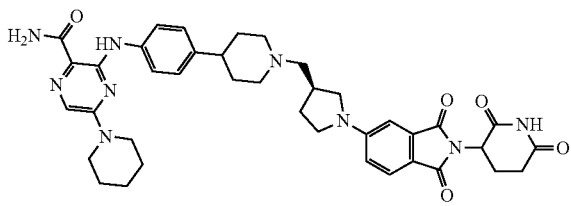

and

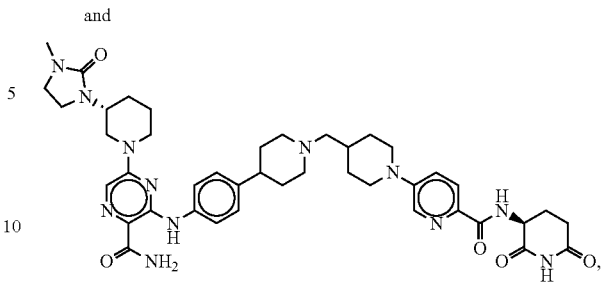

or a pharmaceutically acceptable salt thereof,
wherein the cancer is a B cell malignancy.

2. The method of claim 1, wherein the cancer is selected from the group consisting of chronic lymphocytic leukemia, mantle cell lymphoma, marginal zone lymphoma, Waldenstrom's macroglobulinemia, follicular lymphoma, diffuse large B cell lymphoma, small cell lymphocytic leukemia, primary central nervous system lymphoma, and combinations thereof.

3. The method of claim 1, wherein the human subject has a C481 mutant Bruton's tyrosine kinase, or a C481S mutant Bruton's tyrosine kinase.

4. The method of claim 1, wherein the subject has a C481 mutant Bruton's tyrosine kinase and the cancer is chronic lymphocytic leukemia (CLL).

5. The method of claim 1, wherein the subject has a C481S mutant Bruton's tyrosine kinase and the cancer is chronic lymphocytic leukemia (CLL).

6. The method of claim 1, wherein the cancer is resistant to ibrutinib, acalabrutinib, pirtobrutinib, or any combination thereof.

7. The method of claim 1, wherein the human subject has had prior treatment with ibrutinib, acalabrutinib, pirtobrutinib, or any combination thereof.

8. The method of claim 1, wherein the cancer is chronic lymphocytic leukemia.

9. The method of claim 1, wherein the cancer is chronic lymphocytic leukemia; and wherein the compound of formula I is:

| Compound Number | Structure |
| --- | --- |
| 149 | 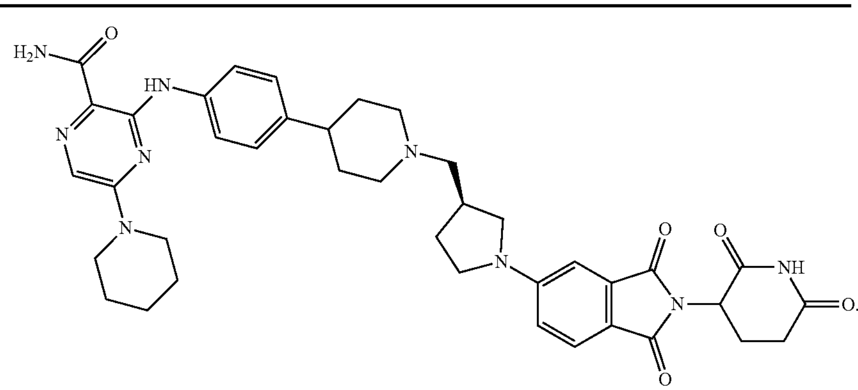 |

10. The method of claim 1, wherein the cancer is chronic lymphocytic leukemia; and wherein the compound of formula I is:
| Compound Number | Structure |
|---|---|
| 195 | 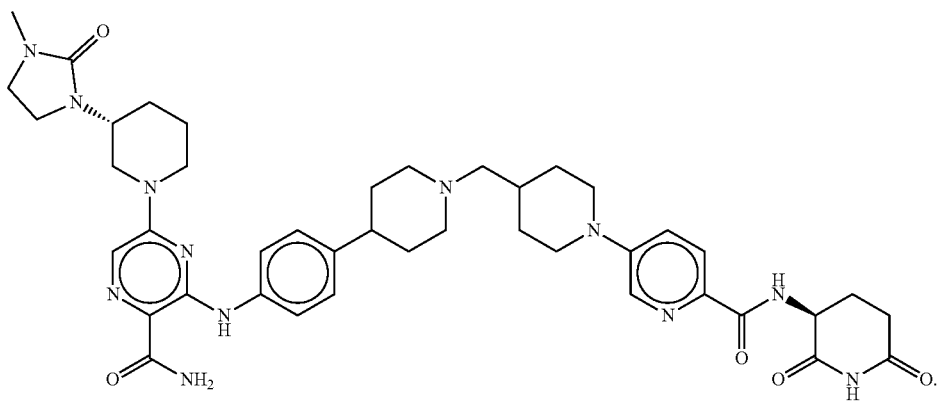 |
11. The method of claim 1, wherein the compound of formula I is administered to the human subject at a daily dose of about 300 mg; and wherein the compound of formula I is:
| Compound Number | Structure |
|---|---|
| 149 | 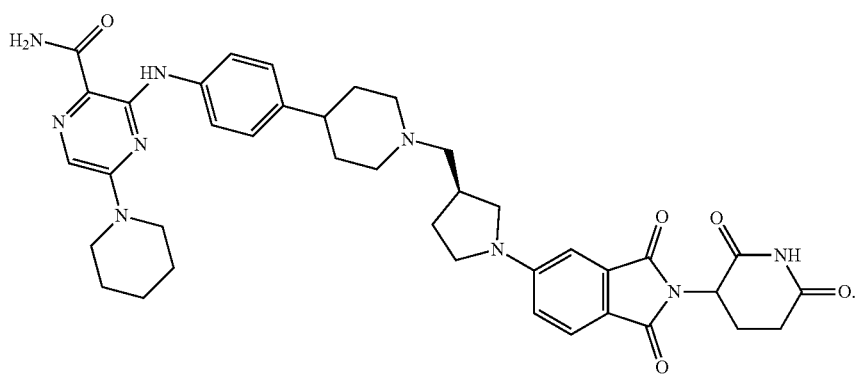 [SMILES: NC(=O)c1ncc(N2CCCCC2)nc1Nc1ccc(C2CCN(C[C@@H]3CCN(c4ccc5c(c4)C(=O)N(C4CCC(=O)NC4=O)C5=O)C3)CC2)cc1] |

12. The method of claim 1, wherein the cancer is chronic lymphocytic leukemia; wherein the compound of formula I is administered to the human subject at a daily dose of about 100 mg; and wherein the compound of formula I is:

| Compound Number | Structure |
|---|---|
| 149 | 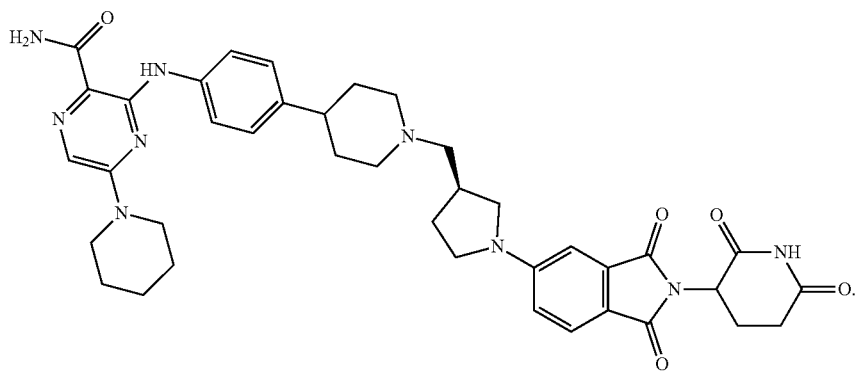 [SMILES: NC(=O)c1ncc(N2CCCCC2)nc1Nc1ccc(C2CCN(C[C@@H]3CCN(c4ccc5c(c4)C(=O)N(C4CCC(=O)NC4=O)C5=O)C3)CC2)cc1] |

13. The method of claim 1, wherein the compound of formula I is administered to the human subject at a daily dose of about 100 mg; and wherein the compound of formula I is:

| Compound Number | Structure |
|---|---|
| 195 | 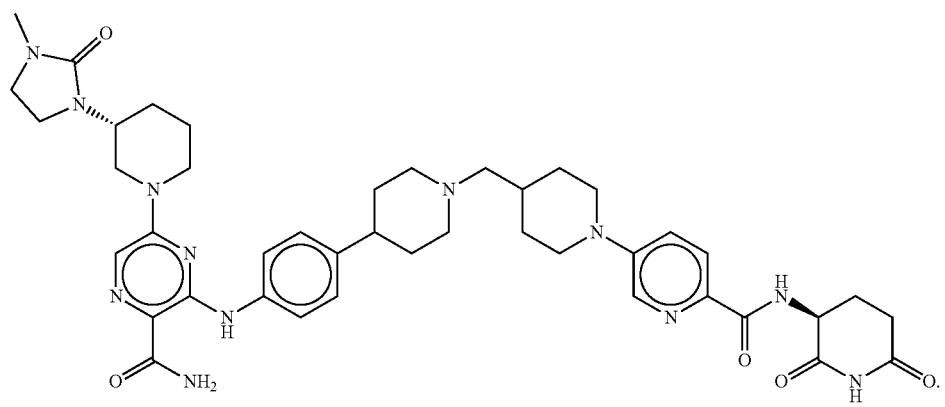 |

14. The method of claim 1, wherein the cancer is chronic lymphocytic leukemia; the compound of formula I is administered to the human subject at a daily dose of about 50 mg; and the compound of formula I is:

| Compound Number | Structure |
|---|---|
| 195 | *(chemical structure)* |

15. The method of claim 1, wherein the cancer is chronic lymphocytic leukemia; the compound of formula I is administered to the human subject at a daily dose of about 100 mg; and the compound of formula I is:

| Compound Number | Structure |
|---|---|
| 195 | *(chemical structure)* |

16. The method of claim 1, wherein the cancer is diffuse large B cell lymphoma, germinal center B-cell-like (GCB) DLBCL, non-GCB DLBCL, activated B-cell-like (ABC) DLBCL, follicular lymphoma (FL), marginal zone lymphoma (MZL), Waldenstrom's macroglobulinemia (WM), or mantle cell lymphoma (MCL).

17. The method of claim 1, wherein the compound of formula I is administered to the human subject in a form of intermittent dosing; and
    wherein the intermittent dosing form comprises an administration period and a break period.

18. The method of claim 17, wherein the intermittent dosing is repeated throughout the treatment.

19. The method of claim 17, wherein the administration period is 2 weeks; wherein the break period is 2 weeks; and further wherein the intermittent dosing is preceded by a loading dose for a period of 4 weeks.

20. The method of claim 17, wherein the administration period is 3 weeks; wherein the break period is 1 weeks; and further wherein the intermittent dosing is preceded by a loading dose for a period of 4 weeks.

21. The method of claim 1, wherein the compound of formula I is administered to the human subject in a form of intermittent dosing;
    wherein the intermittent dosing form comprises an administration period and a break period; and
    wherein the intermittent dosing is preceded by a loading dose.

22. The method of claim 21, wherein the intermittent dosing is repeated throughout the treatment.

23. The method of claim 21, wherein the administration period is 2 weeks; and wherein the break period is 2 weeks.

24. The method of claim 21, wherein the administration period is 3 weeks; and wherein the break period is 1 week.

25. The method of claim 1, wherein the human subject has had prior treatment with a Bruton's tyrosine kinase inhibitor.

26. A method of degrading Bruton's tyrosine kinase in a human subject in need thereof, comprising the step of orally administering to the human subject a daily oral dose of about 100 mg to about 500 mg of a compound of formula I
    is selected from hydrogen and substituted or unsubstituted heterocycle;

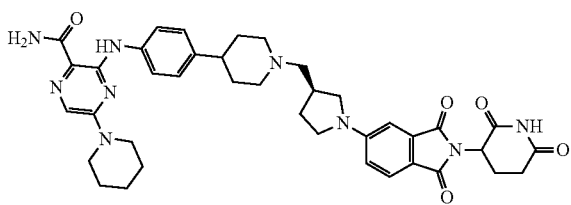

and

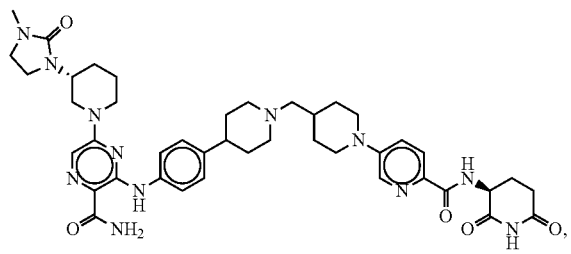

or a pharmaceutically acceptable salt thereof.

27. The method of claim 26 wherein the Bruton's tyrosine kinase is degraded by at least 85%, 90%, or 95% compared to baseline levels.

28. The method of claim 26, wherein the Bruton's tyrosine kinase is in splenocytes, plasma, peripheral blood mononuclear cells, or circulating B cells.

29. The method of claim 26, wherein the compound of formula I is administered to the human subject at a daily dose of about 100 mg, about 200 mg, about 300 mg, about 400 mg, or about 500 mg.

30. The method of claim 26, wherein the compound of formula I is administered in one, two, three, or four divided doses per day.

31. The method of claim 26, wherein the compound of formula I is administered daily for one, two, three, four, five, six, seven, eight, nine, ten, eleven, twelve, thirteen, fourteen, fifteen, or thirty or more days.

32. The method of claim 26, wherein the compound of formula I is administered cyclically.

33. The method of claim 26, wherein the compound of formula I is administered in a form of a pharmaceutical composition comprising the compound of formula I or pharmaceutically acceptable salt thereof and a pharmaceutically acceptable carrier, vehicle, or adjuvant.

34. The method of claim 26, wherein the human subject has had prior treatment with a Bruton's tyrosine kinase inhibitor.

\* \* \* \* \*